US008802727B2

(12) United States Patent
Parthasaradhi Reddy et al.

(10) Patent No.: US 8,802,727 B2
(45) Date of Patent: *Aug. 12, 2014

(54) PHARMACEUTICALLY ACCEPTABLE SALTS OF BETULINIC ACID DERIVATIVES

(75) Inventors: Bandi Parthasaradhi Reddy, Andhra Pradesh (IN); Vedula Manohar Sharma, Andhra Pradesh (IN); Kura Rathnakar Reddy, Andhra Pradesh (IN); Musku Madhanmohan Reddy, Andhra Pradesh (IN)

(73) Assignee: Hetero Research Foundation, Hetero Drugs Limited (IN)

( * ) Notice: Subject to any disclaimer, the term of this patent is extended or adjusted under 35 U.S.C. 154(b) by 148 days.

This patent is subject to a terminal disclaimer.

(21) Appl. No.: 12/987,228

(22) Filed: Jan. 10, 2011

(65) Prior Publication Data
US 2011/0218204 A1 Sep. 8, 2011

Related U.S. Application Data

(63) Continuation-in-part of application No. 12/829,483, filed on Jul. 2, 2010.

(60) Provisional application No. 61/251,933, filed on Oct. 15, 2009.

(30) Foreign Application Priority Data

Jul. 14, 2009 (IN) .......................... 1670/CHE/2009
Mar. 8, 2010 (IN) ............................ 587/CHE/2010

(51) Int. Cl.
*A61K 31/21* (2006.01)
*C07J 53/00* (2006.01)
*C07J 63/00* (2006.01)

(52) U.S. Cl.
CPC ................................... *C07J 63/008* (2013.01)
USPC .......................................... 514/510; 552/510

(58) Field of Classification Search
USPC ......................................... 552/510; 510/510
See application file for complete search history.

(56) References Cited

U.S. PATENT DOCUMENTS

| 6,670,345 | B1 | 12/2003 | Ramadoss et al. |
| 7,923,573 | B2 * | 4/2011 | Tamaki et al. ................... 560/61 |
| 2006/0205697 | A1 | 9/2006 | Robinson et al. |
| 2008/0207573 | A1 | 8/2008 | Yager et al. |
| 2011/0152229 | A1 | 6/2011 | Chen et al. |

FOREIGN PATENT DOCUMENTS

| WO | 0046235 | | 8/2000 |
| WO | 02091858 | A1 | 11/2002 |
| WO | 2005090380 | A1 | 9/2005 |
| WO | WO2005090380 | * | 9/2005 |
| WO | 2006105356 | A2 | 10/2006 |
| WO | 2007002411 | A1 | 1/2007 |
| WO | 2007141383 | A1 | 12/2007 |
| WO | 2007141390 | A1 | 12/2007 |
| WO | 2007141392 | A2 | 12/2007 |
| WO | 2008057420 | A2 | 5/2008 |
| WO | 2008091532 | A1 | 7/2008 |
| WO | 2008127364 | A2 | 10/2008 |
| WO | 2009082819 | A1 | 7/2009 |
| WO | 2009100532 | A1 | 8/2009 |
| WO | 2010132334 | A1 | 11/2010 |
| WO | 2011007230 | A2 | 1/2011 |
| WO | WO2011007230 | * | 1/2011 |

OTHER PUBLICATIONS

Antimonova, A.N. et al., Synthesis of Betulonic Acid Amides, Chemistry of Natural Compounds, 2008, vol. 44, No. 3, pp. 327-333.
Sun, i. et al., Anti-AIDS Agents, 34. Synthesis and Structure-Activity Relationships of Betulin Derivatives as Anti-HIV Agents, J. Med. Chem. 1998, vol. 41, pp. 4648-4657.
Zhu, YM, et al., Synthesis and Anti-HIV Activity Oleanolic Acid Derivatives, Bioorganic & Medicinal Chemistry Letters, 2001, vol. 11, pp. 3115-3118.
Hashimoto, F. et al., Anti-AIDS Agents—XVVIL. Synthesis and Anti-HIV Activity of Betulinic Acid and Dihydrobetulinic Acid Derivatives, Bioorganic & Medicinal Chemistry, 1997, vol. 5, No. 12, pp. 2133-2143.
Qian, K. et al., Anti-AIDS Agents 81. Design, Synthesis, and Structure—Activity Relationship Study of Betulinic Acid and Moronic Acid Derivatives as Potent HIV Maturation Inhibitors, J. Med. Chem., 2010, vol. 53, pp. 3133-3141.
International Search Report for PCT/IB2010/001677 dated Jul. 5, 2010 and Written Opinion.
Aguado et al., "Enantidivergent synthesis of cyclobutyl-(Z)-a,β-dehydro-a-amino acid derivatives from (-)-cis-pinononic acid", Tetrahedron: Asymmetry 14, 2003, pp. 217-223.
Aguilera et al., "Stereodivergent synthesis of the first bis(cyclobutane) y-dipeptides and mixed y-oligomers", Tetrahedron: Asymmetry 19, 2008, pp. 302-308.
Kanamoto et al., "Anti-Human Immunodeficiency Virus Activity of YK-FH312 (a Betulinic Acid Derivative), a Novel Compound Blocking Viral Maturation", Antimicrobial Agents and Chemotherapy, 2001, pp. 1225-1230.
Kashiwada et al., "Betulinic Acid and Dihydrobetulinic Acid Derivatives as Potent Anti-HIV Agents", J. Med. Chem. 1996, 39, pp. 1016-1017.
Li et al., "PA-457: A potent HIV inhibitor that disrupts core condensation by targeting a late step in Gag processing", Proc. Natl. Acad. Sci. 2003, pp. 13555-13560.
Moglioni et al., "Divergent Routes to Chiral Cyclobutane Synthons from (-)-a-Pinene and Their Use in the Steroselective Synthesis of Dehydro Amino Acids", J. Org. Chem. 2000, 65, pp. 3934-3940.
International Search Report and Written Opinion for International Application No. PCT/IB2010001677, International Application Filing Date Jul. 5, 2010, Date of Mailing Apr. 12, 2011, 23 pages.

(Continued)

*Primary Examiner* — Barbara P Badio
(74) *Attorney, Agent, or Firm* — Cantor Colburn LLP

(57) ABSTRACT

The present invention relates to certain novel salts of Betulinic acid derivatives, to process for preparing such compounds, to use the compounds in treating diseases or disorders mediated by HIV infection, to methods for their therapeutic use and to pharmaceutical compositions containing them.

24 Claims, 36 Drawing Sheets

(56) References Cited

OTHER PUBLICATIONS

International Search Report and Written Opinion for International Application No. PCT/IB2011/054183, International Application Filing Date Sep. 22, 2011, Date of Mailing Mar. 16, 2012, 14 pages.
Popik et al., "Human Immunodeficiency Virus Type 1 Uses Lipid Raft-Colocalized CD4 and Chemokine Receptors for Productive Entry into CD4+ T Cells", J. of Virology, 2002, pp. 4709-4722.
Sakalian et al., "3-O-(3',3'-Dimethysuccinyl) Betulinic Acid Inhibits Maturation of the Human Immunodeficiency Virus Type 1 Gag Precursor Assemble In Vitro", J. of Virology, 2006, pp. 5716-5722.
Zhou et al., "Small-Molecule Inhibition of Human Immunodeficiency Virus Type 1 Replication by Specific Targeting of the Final Step of Virion Maturation", J. of Virology, 2004, pp. 922-929.
Zhou et al., "Inhibition of HIV-1 Maturation via Drug Association with the Viral Gag Protein in Immature HIV-1 Particles", J. of Bio. Chem., 2005, vol. 280, No. 51, pp. 42149-42155.

\* cited by examiner

| S.No | d value (angstrom) | Intensity (rel) |
|---|---|---|
| 1. | 5.67 | Vs |
| 2. | 5.51 | s |
| 3. | 4.94 | s |
| 4. | 4.78 | Vs |
| 5. | 4.53 | m |
| 6. | 4.01 | w |
| 7. | 3.62 | w |
| 8. | 3.45 | w |
| 9. | 3.07 | w |
| 10. | 2.83 | w |
| 11. | 2.79 | w |
| 12. | 2.75 | w |
| 13. | 2.71 | w |
| 14. | 2.55 | w |

Vs = Very strong
s = strong
m = medium
w = weak

FIG. 1B

| S.No | d value (angstrom) | Intensity |
|---|---|---|
| 1. | 17.56 | m |
| 2. | 16.74 | m |
| 3. | 14.13 | s |
| 4. | 12.48 | w |
| 5. | 11.72 | w |
| 6. | 10.67 | m |
| 7. | 10.44 | m |
| 8. | 9.90 | w |
| 9. | 9.19 | m |
| 10. | 8.95 | m |
| 11. | 8.71 | m |
| 12. | 8.34 | m |
| 13. | 7.69 | s |
| 14. | 7.54 | m |
| 15. | 7.21 | m |
| 16. | 6.87 | s |
| 17. | 6.59 | Vs |
| 18. | 6.48 | s |
| 19. | 6.19 | m |
| 20. | 6.10 | m |
| 21. | 6.03 | m |
| 22. | 5.89 | m |
| 23. | 5.66 | m |
| 24. | 5.55 | m |
| 25. | 5.38 | s |
| 26. | 5.18 | m |
| 27. | 5.05 | m |
| 28. | 4.92 | m |
| 29. | 4.81 | m |
| 30. | 4.55 | m |
| 31. | 4.47 | m |
| 32. | 4.35 | m |
| 33. | 4.25 | w |

FIG. 2B

| | | |
|---|---|---|
| 34. | 4.16 | w |
| 35. | 4.02 | w |
| 36. | 3.97 | w |
| 37. | 3.94 | w |
| 38. | 3.81 | m |
| 39. | 3.76 | m |
| 40. | 3.69 | w |
| 41. | 3.56 | w |
| 42. | 3.44 | w |
| 43. | 3.31 | m |
| 44. | 3.16 | m |
| 45. | 3.08 | w |
| 46. | 3.01 | w |
| 47. | 2.97 | w |
| 48. | 2.87 | w |
| 49. | 2.84 | w |
| 50. | 2.82 | w |
| 51. | 2.74 | w |
| 52. | 2.67 | w |
| 53. | 2.61 | w |
| 54. | 2.55 | w |
| 55. | 2.51 | w |
| 56. | 2.49 | w |
| 57. | 2.40 | w |
| 58. | 2.37 | w |
| 59. | 2.29 | w |
| 60. | 2.26 | w |
| 61. | 2.21 | w |

FIG. 2C

| S.No | d value (angstrom) | Intensity |
|---|---|---|
| 1 | 19.62 | w |
| 2 | 17.16 | w |
| 3 | 16.64 | w |
| 4 | 13.37 | w |
| 5 | 11.62 | w |
| 6 | 10.84 | m |
| 7 | 10.34 | w |
| 8 | 9.77 | w |
| 9 | 9.45 | w |
| 10 | 9.12 | m |
| 11 | 8.89 | m |
| 12 | 8.62 | w |
| 13 | 8.27 | m |
| 14 | 7.62 | s |
| 15 | 7.44 | m |
| 16 | 7.17 | m |
| 17 | 6.82 | s |
| 18 | 6.55 | Vs |
| 19 | 6.41 | m |
| 20 | 6.20 | m |
| 21 | 6.09 | m |
| 22 | 5.83 | m |
| 23 | 5.63 | m |
| 24 | 5.51 | m |
| 25 | 5.33 | s |
| 26 | 5.16 | m |
| 27 | 5.02 | s |
| 28 | 4.87 | m |
| 29 | 4.77 | m |
| 30 | 4.61 | w |
| 31 | 4.52 | m |
| 32 | 4.43 | m |
| 33 | 4.31 | m |
| 34 | 4.22 | m |
| 35 | 4.15 | w |

FIG. 3B

| 36 | 3.99 | w |
| --- | --- | --- |
| 37 | 3.94 | w |
| 38 | 3.80 | w |
| 39 | 3.73 | w |
| 40 | 3.68 | w |
| 41 | 3.61 | w |
| 42 | 3.55 | w |
| 43 | 3.52 | w |
| 44 | 3.43 | w |
| 45 | 3.28 | m |
| 46 | 3.19 | w |
| 47 | 3.13 | m |
| 48 | 3.08 | w |
| 49 | 3.05 | w |
| 50 | 2.99 | w |
| 51 | 2.95 | w |
| 52 | 2.91 | w |
| 53 | 2.86 | w |
| 54 | 2.80 | w |
| 55 | 2.78 | w |
| 56 | 2.72 | w |
| 57 | 2.66 | w |
| 58 | 2.64 | w |
| 59 | 2.60 | w |
| 60 | 2.58 | w |
| 61 | 2.55 | w |
| 62 | 2.35 | w |
| 63 | 2.27 | w |
| 64 | 2.26 | w |

FIG. 3C

| S.No | d value (angstrom) | Intensity |
|---|---|---|
| 1 | 14.53 | w |
| 2 | 10.92 | w |
| 3 | 10.41 | w |
| 4 | 9.72 | w |
| 5 | 9.29 | m |
| 6 | 9.01 | w |
| 7 | 8.63 | w |
| 8 | 8.31 | w |
| 9 | 7.92 | w |
| 10 | 7.67 | w |
| 11 | 7.35 | m |
| 12 | 6.88 | m |
| 13 | 6.61 | Vs |
| 14 | 6.42 | s |
| 15 | 6.13 | s |
| 16 | 5.91 | w |
| 17 | 5.70 | w |
| 18 | 5.57 | m |
| 19 | 5.43 | m |
| 20 | 5.28 | w |
| 21 | 5.09 | m |
| 22 | 4.84 | m |
| 23 | 4.79 | m |
| 24 | 4.60 | m |
| 25 | 4.56 | m |
| 26 | 4.48 | m |
| 27 | 4.34 | w |
| 28 | 4.24 | w |
| 29 | 4.17 | w |
| 30 | 4.11 | w |
| 31 | 3.98 | w |
| 32 | 3.85 | w |

FIG. 4B

| | | |
|---|---|---|
| 33 | 3.81 | w |
| 34 | 3.75 | w |
| 35 | 3.69 | w |
| 36 | 3.65 | w |
| 37 | 3.54 | w |
| 38 | 3.42 | w |
| 39 | 3.37 | w |
| 40 | 3.30 | w |
| 41 | 3.15 | w |
| 42 | 3.09 | w |
| 43 | 3.06 | w |
| 44 | 3.01 | w |
| 45 | 2.95 | w |
| 46 | 2.80 | w |
| 47 | 2.74 | w |

FIG. 4C

| S.No | d value (angstrom) | Intensity |
|---|---|---|
| 1 | 11.74 | m |
| 2 | 10.49 | m |
| 3 | 9.08 | m |
| 4 | 8.26 | m |
| 5 | 7.65 | m |
| 6 | 6.86 | s |
| 7 | 6.59 | Vs |
| 8 | 6.08 | s |
| 9 | 5.87 | s |
| 10 | 5.54 | s |
| 11 | 5.35 | s |
| 12 | 5.04 | m |
| 13 | 4.92 | m |
| 14 | 4.79 | m |
| 15 | 4.54 | m |

FIG. 5B

| S.No | d value (angstrom) | Intensity |
|---|---|---|
| 1 | 13.45 | Vs |
| 2 | 11.88 | w |
| 3 | 10.65 | w |
| 4 | 9.91 | w |
| 5 | 9.08 | m |
| 6 | 8.45 | w |
| 7 | 7.75 | m |
| 8 | 6.94 | m |
| 9 | 6.69 | s |
| 10 | 6.56 | m |
| 11 | 6.21 | m |
| 12 | 6.09 | m |
| 13 | 6.03 | m |
| 14 | 5.95 | m |
| 15 | 5.87 | m |
| 16 | 5.62 | m |
| 17 | 5.56 | m |
| 18 | 5.47 | m |
| 19 | 5.41 | m |
| 20 | 5.24 | m |
| 21 | 5.12 | m |
| 22 | 4.93 | m |
| 23 | 4.78 | m |
| 24 | 4.73 | m |
| 25 | 4.61 | m |
| 26 | 4.53 | m |
| 27 | 4.45 | w |
| 28 | 4.35 | w |
| 29 | 4.26 | w |
| 30 | 4.01 | w |
| 31 | 3.85 | w |
| 32 | 3.62 | w |
| 33 | 3.55 | w |

FIG. 6B

| 34 | 3.52 | w |
| 35 | 3.48 | w |
| 36 | 3.44 | w |
| 37 | 3.33 | w |
| 38 | 3.18 | w |
| 39 | 3.16 | w |
| 40 | 3.12 | w |
| 41 | 3.09 | w |
| 42 | 3.06 | w |
| 43 | 2.97 | w |
| 44 | 2.95 | w |
| 45 | 2.86 | w |
| 46 | 2.78 | w |
| 47 | 2.71 | w |
| 48 | 2.66 | w |
| 49 | 2.62 | w |
| 50 | 2.60 | w |
| 51 | 2.54 | w |
| 52 | 2.50 | w |
| 53 | 2.46 | w |
| 54 | 2.40 | w |
| 55 | 2.30 | w |
| 56 | 2.22 | w |
| 57 | 2.14 | w |

FIG. 6C

| S.No | d value (angstrom) | Intensity |
|---|---|---|
| 1 | 27.39 | s |
| 2 | 20.56 | m |
| 3 | 18.01 | w |
| 4 | 13.71 | w |
| 5 | 12.83 | s |
| 6 | 11.77 | m |
| 7 | 11.40 | m |
| 8 | 10.98 | w |
| 9 | 10.26 | m |
| 10 | 9.89 | s |
| 11 | 9.14 | m |
| 12 | 8.43 | s |
| 13 | 7.91 | s |
| 14 | 7.52 | m |
| 15 | 7.29 | w |
| 16 | 6.83 | s |
| 17 | 6.63 | Vs |
| 18 | 6.57 | Vs |
| 19 | 6.42 | m |
| 20 | 6.15 | s |
| 21 | 5.94 | s |
| 22 | 5.58 | s |
| 23 | 5.39 | w |
| 24 | 5.27 | m |
| 25 | 5.08 | m |
| 26 | 4.90 | w |
| 27 | 4.76 | w |
| 28 | 4.58 | s |
| 29 | 4.49 | m |
| 30 | 4.38 | w |

FIG. 7B

| 31 | 4.21 | w |
| --- | --- | --- |
| 32 | 4.06 | m |
| 33 | 3.93 | m |
| 34 | 3.83 | w |
| 35 | 3.62 | w |
| 36 | 3.48 | w |
| 37 | 3.45 | w |
| 38 | 3.35 | w |
| 39 | 3.30 | w |
| 40 | 3.24 | w |
| 41 | 3.08 | w |
| 42 | 3.05 | w |
| 43 | 3.01 | w |
| 44 | 2.92 | w |
| 45 | 2.85 | w |
| 46 | 2.80 | w |
| 47 | 2.66 | w |
| 48 | 2.64 | w |
| 49 | 2.62 | w |
| 50 | 2.56 | w |
| 51 | 2.54 | w |
| 52 | 2.46 | w |
| 53 | 2.42 | w |
| 54 | 2.34 | w |
| 55 | 2.27 | w |
| 56 | 2.25 | w |
| 57 | 2.23 | w |
| 58 | 2.21 | w |
| 59 | 2.17 | w |
| 60 | 2.11 | w |
| 61 | 2.07 | w |

FIG. 7C

PHARMACEUTICALLY ACCEPTABLE SALTS OF BETULINIC ACID DERIVATIVES

FIELD OF THE INVENTION

The present invention relates to certain novel salts of Betulinic acid derivatives, to process for preparing such compounds, to use the compounds in treating diseases or disorders mediated by HIV infection, to methods for their therapeutic use and to pharmaceutical compositions containing them.

BACKGROUND OF THE INVENTION

Inhibition of virally encoded protease of the human immuno deficiency virus results in the production of immature, non-infectious virions. HIV protease specifically process gag and gag-pol viral poly proteins to yield the viral structural proteins, as well as the viral enzymes reverse transcriptase, integrase and protease. Betulinic acid derivatives were known as first of a new class of anti-retroviral agents that inhibit HIV-1 replication by disrupting virus maturation (Science 1983, 220, 868-871; N. Eng. J. Med. 1984, 311, 1292-1297). For example, Bevirimat as a compound with a novel mechanism of action (J. Nat. Prod. 199457(2):243-7; J. Med. Chem. 1996, 39(5), 1016). Further studies shown that bevirimat acts by disrupting gag processing (Proc. Natl. Acad. Sci. USA 2003, 100(23):13555-60; Antimicrob. Agents. Chemother. 2001, 45 (4), 1225-30; J. Virol., 2004, 78(2): 922-9; J. Biol. Chem. 2005, 280 (51): 42149-55; J. Virol. 2006, 80 (12): 5716-22) and to be a first-in-class maturation inhibitor with a potent activity against HIV-1. Due to this novel mechanism of action, some of these derivatives did show potent activity against HIV-1 strains that are resistant to currently approved classes of anti-retroviral agent.

Our co-pending PCT application PCT/IB2010/001677 filed on 5 Jul. 2010 discloses certain compounds of betulinic acid derivatives and is herein incorporated by reference. These compounds are highly active against HIV strains of different subtypes. Even though, said application discloses generically pharmaceutically acceptable salts of said compounds, specific pharmaceutically acceptable salts of compounds of present invention are not disclosed in PCT/IB2010/001677. Further, no information is provided, in relation to crystalline forms of disclosed compounds, particularly salts thereof Compounds disclosed in PCT/IB2010/001677 are free acids. Therefore there is need for preparing pharmaceutically acceptable salts of these compounds which have physical and chemical properties suitable for using pharmaceutical formulations.

Further, in the manufacturing of drug compositions, it is important that a reliable, reproducible and constant plasma concentration profile of drug is provided following administration to patients. Chemical stability, salt state stability and shelf life of the active ingredients are also very important factors. The drug substances and compositions containing it should preferably capable of being effectively stored over appreciable periods of time without exhibiting a significant change in the active components physiochemical characteristics like chemical composition, density, hygroscopicity and solubility. Moreover it is also important to be able to provide drug in a form which is as chemically pure as possible. If possible, it is desirable to enhance biological properties like bioavailability by improving dissolution properties. One among the numerous pharmaceutical approaches to achieve the above said properties is preparing pharmaceutically acceptable salts.

SUMMARY OF THE INVENTION

The present invention relates to certain novel salts of formula (I):

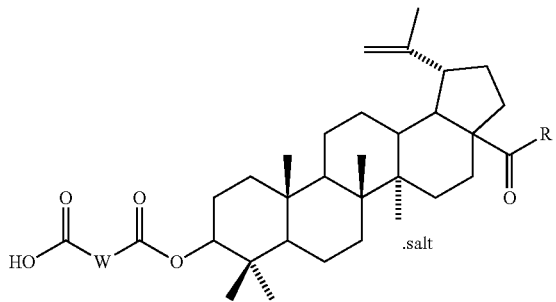

Formula (I)

Wherein,
R can be OH,

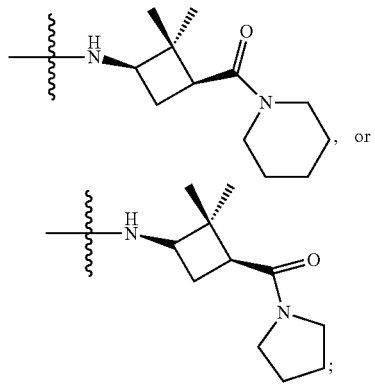

, or

;

W can be

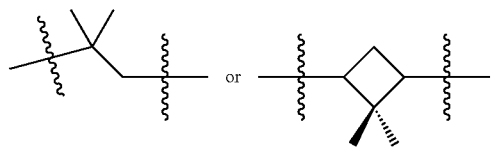

Salt can be an arginine, amino guanidine, choline, dicyclohexylamine, diethanolamine, dimethyl piperazine, lithium, lysine, magnesium, N-methyl glucamine, N-octyl glucamine, piperazine, phenyl glycine methyl ester, phenyl glycinol, potassium, sodium, Tris(hydroxymethyl)aminomethane, or calcium.

It should be understood that formula (I) structurally encompasses all stereoisomers, including enantiomers, diastereomers, racemates, and mixtures thereof, which may be contemplated from the chemical structure of the genus described herein.

Also contemplated are prodrugs of the compounds of the formula (I).

According to one embodiment, there is provided a compound of formula (I), wherein R is OH.

According to one embodiment, there is provided a compound of formula (I), wherein R is

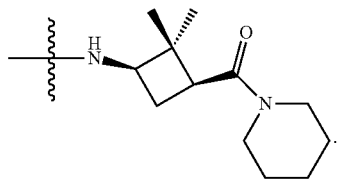

According to one embodiment, there is provided a compound of formula (I), wherein R is

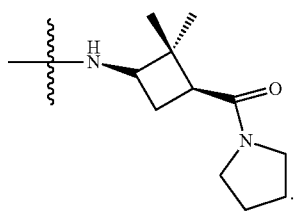

According to one embodiment, there is provided a compound of formula (I), wherein W is

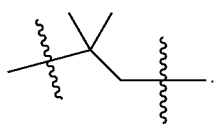 [SMILES: *CC(*)(C)C]

According to one embodiment, there is provided a compound of formula (I), wherein W is

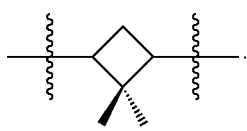

According to one embodiment, there is provided a compound of formula (I), wherein a salt is arginine.

According to one embodiment, there is provided a compound of formula (I), wherein a salt is amino guanidine.

According to one embodiment, there is provided a compound of formula (I), wherein a salt is calcium.

According to one embodiment, there is provided a compound of formula (I), wherein a salt is choline.

According to one embodiment, there is provided a compound of formula (I), wherein a salt is dicyclohexylamine.

According to one embodiment, there is provided a compound of formula (I), wherein a salt is diethanolamine.

According to one embodiment, there is provided a compound of formula (I), wherein a salt is 2,6-dimethyl piperazine According to one embodiment, there is provided a compound of formula (I), wherein a salt is lithium.

According to one embodiment, there is provided a compound of formula (I), wherein a salt is lysine.

According to one embodiment, there is provided a compound of formula (I), wherein a salt is magnesium.

According to one embodiment, there is provided a compound of formula (I), wherein a salt is N-methyl glucamine.

According to one embodiment, there is provided a compound of formula (I), wherein a salt is N-octyl glucamine.

According to one embodiment, there is provided a compound of formula (I), wherein a salt is piperazine.

According to one embodiment, there is provided a compound of formula (I), wherein a salt is phenyl glycine methyl ester.

According to one embodiment, there is provided a compound of formula (I), wherein a salt is phenyl glycinol.

According to one embodiment, there is provided a compound of formula (I), wherein a salt is potassium.

According to one embodiment, there is provided a compound of formula (I), wherein a salt is sodium.

According to one embodiment, there is provided a compound of formula (I), wherein a salt is Tris(hydroxymethyl) amino methane.

According to one embodiment, there is provided a compound of formula (I), wherein the Arginine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid is characterized by an x-ray powder diffraction pattern substantially in accordance with that shown in FIG. 1 and a differential scanning calorimetry thermogram substantially in accordance with that shown in FIG. 8.

According to one embodiment, there is provided a compound of formula (I), wherein the Amino guanidine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid is characterized by an x-ray powder diffraction pattern substantially in accordance with that shown in FIG. 2 and a differential scanning calorimetry thermogram substantially in accordance with that shown in FIG. 9.

According to one embodiment, there is provided a compound of formula (I), wherein the Calcium salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid is characterized by an x-ray powder diffraction pattern substantially in accordance with that shown in FIG. 3 and a differential scanning calorimetry thermogram substantially in accordance with that shown in FIG. 10.

According to one embodiment, there is provided a compound of formula (I), wherein the Choline salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)-icosahydro-1H-cyclopenta[a]chrysen-9-yloxy)-2,2-dimethyl-4-oxobutanoic acid is characterized by an x-ray powder diffraction pattern substantially in accordance with that shown in FIG. 4 and a differential scanning calorimetry thermogram substantially in accordance with that shown in FIG. 11.

According to one embodiment, there is provided a compound of formula (I), wherein the Dicyclohexylamine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid is characterized by a differential scanning calorimetry thermogram substantially in accordance with that shown in FIG. 12.

According to one embodiment, there is provided a compound of formula (I), wherein the Diethanolamine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid is characterized by a differential scanning calorimetry thermogram substantially in accordance with that shown in FIG. 13.

According to one embodiment, there is provided a compound of formula (I), wherein the 2,6-dimethyl Piperazine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid is characterized by a differential scanning calorimetry thermogram substantially in accordance with that shown in FIG. 14.

According to one embodiment, there is provided a compound of formula (I), wherein the Lithium salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid is characterized by a differential scanning calorimetry thermogram substantially in accordance with that shown in FIG. 15.

According to one embodiment, there is provided a compound of formula (I), wherein the Magnesium salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid is characterized by a differential scanning calorimetry thermogram substantially in accordance with that shown in FIG. 16.

According to one embodiment, there is provided a compound of formula (I), wherein the N-methyl Glucamine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid is characterized by an x-ray powder diffraction pattern substantially in accordance with that shown in FIG. 5 and a differential scanning calorimetry thermogram substantially in accordance with that shown in FIG. 17.

According to one embodiment, there is provided a compound of formula (I), wherein the N-octyl Glucamine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid is characterized by a differential scanning calorimetry thermogram substantially in accordance with that shown in FIG. 18.

According to one embodiment, there is provided a compound of formula (I), wherein the Piperazine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid is characterized by an x-ray powder diffraction pattern substantially in accordance with that shown in FIG. 6 and a differential scanning calorimetry thermogram substantially in accordance with that shown in FIG. 19.

According to one embodiment, there is provided a compound of formula (I), wherein the Phenyl glycine methyl ester salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid is characterized by a differential scanning calorimetry thermogram substantially in accordance with that shown in FIG. 21.

According to one embodiment, there is provided a compound of formula (I), wherein the Phenyl glycinol salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid is characterized by a differential scanning calorimetry thermogram substantially in accordance with that shown in FIG. 20.

According to one embodiment, there is provided a compound of formula (I), wherein the Potassium salt of 4-((1R,3aR,5aR,5bR,9S,11aR)-3a-((1R,3 S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid is characterized by a differential scanning calorimetry thermogram substantially in accordance with that shown in FIG. 22.

According to one embodiment, there is provided a compound of formula (I), wherein the Sodium salt of 4-((1R,3aR,5aR,5bR,9 S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid is characterized by an x-ray powder diffraction pattern substantially in accordance with that shown in FIG. 7 and a differential scanning calorimetry thermogram substantially in accordance with that shown in FIG. 23.

According to one embodiment, there is provided a compound of formula (I), wherein the Tris(hydroxymethyl)amino methane salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid is characterized by a differential scanning calorimetry thermogram substantially in accordance with that shown in FIG. 24.

Below are the representative salts, which are illustrative in nature only and are not intended to limit to the scope of the invention (Nomenclature has been generated from Chem. Draw Ultra 11.0 version):

Arginine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid (Compound 1), Amino guanidine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid (Compound 2), Calcium salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid (Compound 3), Choline salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)

icosahydro-1H-cyclopenta[a]chrysen-9-yloxy)-2,2-dimethyl-4-oxobutanoic acid (Compound 4), Dicyclohexylamine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid (Compound 5), Diethanolamine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid (Compound 6), 2,6-dimethyl Piperazine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid (Compound 7), Lithium salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid (Compound 8), Lysine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid (Compound 9), Magnesium salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid (Compound 10), N-methyl Glucamine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid (Compound 11), N-octyl Glucamine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid (Compound 12), Piperazine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid (Compound 13), Phenyl glycine methyl ester salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid (Compound 14), Phenyl glycinol salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid (Compound 15), Potassium salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid (Compound 16), Sodium salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid (Compound 17), Tris(hydroxymethyl)amino methane salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid (Compound 18), Sodium salt of 4-((1R,3aS,5aS,7aR,9S,11aR,11bS,13aR)-3a-((1S,3S)-2,2-dimethyl-3-(pyrrolidine-1-carbonyl)cyclobutylcarbamoyl)-5a,8,8,11a,13a-pentamethyl-1-(prop-1-en-2-yl)icosahydro-1H-cyclopenta[a]chrysen-9-yloxy)-2,2-dimethyl-4-oxobutanoic acid (Compound 19), Potassium salt of 4-((1R,3aS,5aS,7aR,9S,11aR,11bS,13aR)-3a-((1S,3S)-2,2-dimethyl-3-(pyrrolidine-1-carbonyl)cyclobutylcarbamoyl)-5a,8,8,11a,13a-pentamethyl-1-(prop-1-en-2-yl)icosahydro-1H-cyclopenta[a]chrysen-9-yloxy)-2,2-dimethyl-4-oxobutanoic acid (Compound 20), N-methyl Glucamine salt of 4-((1R,3aS,5aS,7aR,9S,11aR,11bS,13aR)-3a-((1S,3S)-2,2-dimethyl-3-(pyrrolidine-1-carbonyl)cyclobutylcarbamoyl)-5a,8,8,11a,13a-pentamethyl-1-(prop-1-en-2-yl)icosahydro-1H-cyclopenta[a]chrysen-9-yloxy)-2,2-dimethyl-4-oxobutanoic acid (Compound 21), Arginine salt of (1R,5bS,9S,11aR)-9-((1R,3S)-3-carboxy-2,2-dimethylcyclobutanecarbonyloxy)-5b,8,8,11a-tetramethyl-1-(prop-1-en-2-yl)icosahydro-1H-cyclopenta[a]chrysene-3a-carboxylic acid (Compound 22), Choline hydroxide salt of (1R,5bS,9S,11aR)-9-((1R,3S)-3-carboxy-2,2-dimethylcyclobutanecarbonyloxy)-5b,8,8,11a-tetramethyl-1-(prop-1-en-2-yl)icosahydro-1H-cyclopenta[a]chrysene-3a-carboxylic acid (Compound 23), Diethanolamine salt of (1R,5bS,9S,11aR)-9-((1R,3S)-3-carboxy-2,2-dimethylcyclobutanecarbonyloxy)-5b,8,8,11a-tetramethyl-1-(prop-1-en-2-yl)icosahydro-1H-cyclopenta[a]chrysene-3a-carboxylic acid (Compound 24), Bis-N-methyl glucamine salt of (1R,5bS,9S,11aR)-9-((1R,3S)-3-carboxy-2,2-dimethylcyclobutanecarbonyloxy)-5b,8,8,11a-tetramethyl-1-(prop-1-en-2-yl)icosahydro-1H-cyclopenta[a]chrysene-3a-carboxylic acid (Compound 25), Dipotassium salt of (1R,5bS,9S,11aR)-9-((1R,3S)-3-carboxy-2,2-dimethylcyclobutanecarbonyloxy)-5b,8,8,11a-tetramethyl-1-(prop-1-en-2-yl)icosahydro-1H-cyclopenta[a]chrysene-3a-carboxylic acid (Compound 26), Disodium salt of (1R,5bS,9S,11aR)-9-((1R,3S)-3-carboxy-2,2-dimethylcyclobutanecarbonyloxy)-5b,8,8,11a-tetramethyl-1-(prop-1-en-2-yl)icosahydro-1H-cyclopenta[a]chrysene-3a-carboxylic acid (Compound 27), or pharmaceutically acceptable solvates, including hydrates and prodrugs of compounds are also contemplated.

The present invention also provides a pharmaceutical composition that includes at least one compound of described herein and at least one pharmaceutically acceptable excipient (such as a pharmaceutically acceptable carrier or diluent). Preferably, the pharmaceutical composition comprises a therapeutically effective amount of at least one compound described herein. The compound(s) present in the composition may be associated with a pharmaceutically acceptable excipient (such as a carrier or a diluent) or may be diluted by a carrier, or enclosed within a carrier which may be in the form of a capsule, sachet, paper, or other container.

The compounds and pharmaceutical compositions described herein are useful in the treatment of diseases, conditions and/or disorders mediated by viral infections.

The present invention further provides a method of treating a disease, condition and/or disorder mediated by viral infections in a subject in need thereof by administering to the subject one or more compounds described herein in the amount effective to cause that infection.

Also provided herein are processes for preparing compounds described herein.

Certain compounds of the invention have advantage that they may be prepared in salt form. According to another aspect of the invention, there is provided a compound of the invention, in substantially crystalline form.

The degree of crystallinity or percentage of crystallinity may be determined by the skilled person using X-ray diffraction or by using techniques such as solid state NMR, FTIR, Raman spectroscopy, Differential scanning calorimetry.

The invention provides a method for preventing, ameliorating or treating a HIV mediated disease, disorder or syndrome in a subject in need thereof comprising administering to the subject a therapeutically effective amount of a compound of the invention. The invention further provides a method, wherein the HIV mediated disease, disorder or syndrome is like AIDS, AIDS related complex, or a syndrome characterized by symptoms such as persistent generalized lymphadenopathy, fever and weight loss, or a retroviral infection genetically related to AIDS.

Anti HIV inhibitory potential of the compounds of present invention may be demonstrated by any one or more methodologies known in the art, such as by using the assays described in Mosmann T, December 1983, *Journal of immunological methods*, 65 (1-2), 55-63 and *SPC Cole, cancer chemotherapy and Pharmacology*, 1986, 17, 259-263.

BRIEF DESCRIPTION OF THE DRAWINGS

FIG. 1: (FIG. 1B) Table of d-values.

FIG. 2: (FIG. 2B, FIG. 2C) Table of d-values.

FIG. 3: (FIG. 3B, FIG. 3C) Table of d-values.

FIG. 4: (FIG. 4B, FIG. 4C) Table of d-values.

FIG. 5: (FIG. 5B) Table of d-values.

FIG. 6: (FIG. 6B, FIG. 6C) Table of d-values.

FIG. 7: (FIG. 7B, FIG. 7C) Table of d-values.

DETAILED DESCRIPTION OF THE INVENTION

Figure 1A:
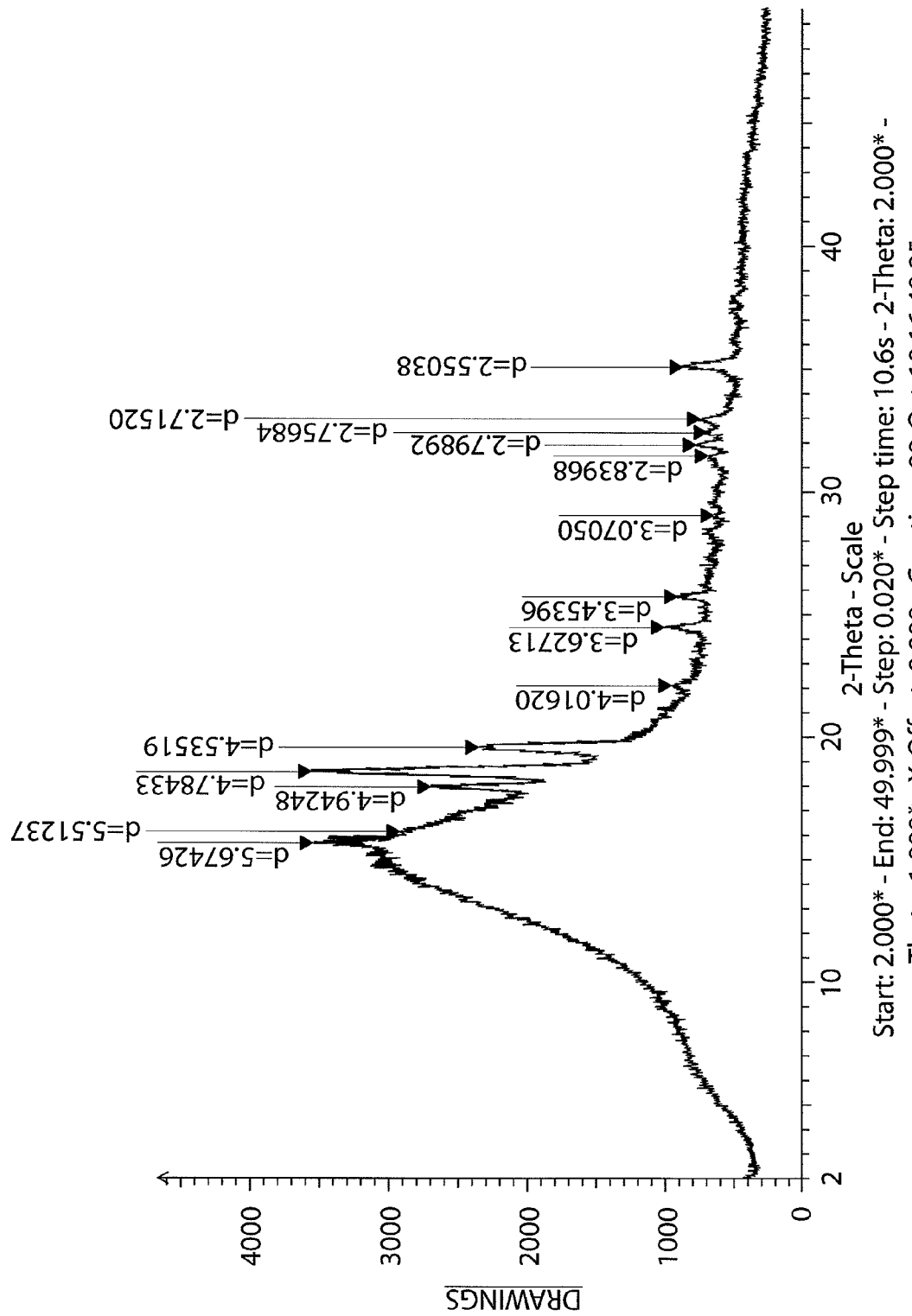
(FIG. 1A) XRPD Arginine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid.

The present invention relates to novel salts of formula (I) and a composition for inhibiting Human Immunodeficiency Virus (HIV) and process for making the compounds.

The Following Definitions Apply to the Terms as Used Herein

The term "prodrug" means a compound that is transformed in vivo to yield a compound of Formula (I) or a hydrate or solvate of the compound. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

The term "treating" or "treatment" of a state, disease, disorder or condition includes:

(1) preventing or delaying the appearance of clinical symptoms of the state, disease, disorder or condition developing in a subject that may be afflicted with or predisposed to the state, disease, disorder or condition but does not yet experience or display clinical or subclinical symptoms of the state, disease, disorder or condition;

(2) inhibiting the state, disease, disorder or condition, i.e., arresting or reducing the development of the state, disease, disorder or condition or at least one clinical or subclinical symptom thereof; or (3) relieving the state, disease, disorder or condition, i.e., causing regression of the state, disease, disorder or condition or at least one of its clinical or subclinical symptoms.

The benefit to a subject receiving treatment is either statistically significant or at least perceptible to the subject or to the physician.

The term "subject" includes mammals (especially humans) and other animals, such as domestic animals (e.g., household pets including cats and dogs) and non-domestic animals (such as wildlife).

A "therapeutically effective amount" means, for example, the amount of a compound that, when administered to a subject for treating a state, disease, disorder or condition, is sufficient to effect such treatment. The "therapeutically effective amount" will vary depending on the compound, the state, disease, disorder or condition and its severity and the age, weight, physical condition and responsiveness of the subject receiving treatment.

Certain salt compounds of this invention are capable of existing in stereoisomeric forms (e.g. diastereomers and enantiomers). With respect to the overall compounds described by the Formula (I), the invention extends to these stereoisomeric forms and to mixtures thereof. To the extent prior art teaches synthesis or separation of particular stereoisomers, the different stereoisomeric forms of the invention may be separated from one another by the method known in the art, or a given isomer may be obtained by stereospecific or asymmetric synthesis. Tautomeric forms and mixtures of compounds described herein are also contemplated.

The present invention describes compounds in substantially pure form. "Substantially pure" as used herein is intended to mean at least 30-99, to 100% pure.

For x-ray diffraction, the present invention is intended to encompass compounds yielding diffractograms that are "substantially in accordance" with those presently shown. A diffractogram "substantially in accordance" would be one that comprises 4, 5, 6, 7, 8, 9, 10, 12, 14, 16, 18, 20, 22, 24, 26, 28, 30, 32, 34, 36, 38, 40 or more of the peaks (i. e, 26 values) within experimental error.

Preferably, it would contain ten or more of the peaks. More preferably, it would contain fourteen or more of the peaks.

Even more preferably, it would contain thirty or more of the peaks. Alternatively, "substantially in accordance" is intended to mean a diffractogram having 20, 25, 30, 35, 40, 45, 50, 55, 60, 65, 70, 75, 80, 85, 90, 95% or more of the same peaks within experimental error. The relative intensities of the peaks may vary, depending upon the sample preparation technique, the sample mounting procedure and the particular instrument employed. Moreover, instrument variation and other factors may affect the 26 values. Therefore, peak assignments inherently include experimental error and may vary by plus or minus 0.2.

For differential scanning calorimetry (DSC), it is known that the temperatures observed will depend upon the rate of temperature change as well as sample preparation technique and the particular instrument employed. Thus, the values shown in the thermograms may vary by plus or minus 4° C. A thermogram "substantially in accordance" would be one whose peaks vary by plus or minus 4° C.

Pharmaceutical Compositions

The pharmaceutical compositions provided in the invention include at least one compound described herein and at least one pharmaceutically acceptable excipient (such as a pharmaceutically acceptable carrier or diluent). Preferably, the contemplated pharmaceutical compositions include a compound(s) described herein in an amount sufficient to treat viral infection in a subject.

The subjects contemplated include, for example, a living cell and a mammal, including human beings. The compound of the present invention may be associated with a pharmaceutically acceptable excipient (such as a carrier or a diluent) or be diluted by a carrier.

Examples of suitable carriers include, but are not limited to, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone.

The carrier or diluent may include a sustained release material, such as, for example, glyceryl monostearate or glyceryl distearate, alone or mixed with a wax.

The pharmaceutical composition may also include one or more pharmaceutically acceptable auxiliary agents, wetting agents, emulsifying agents, suspending agents, preserving agents, salts for influencing osmotic pressure, buffers, sweetening agents, flavoring agents, colorants, or any combination of the foregoing. The pharmaceutical composition of the invention may be formulated so as to provide quick, sustained, or delayed release of the active ingredient after administration to the subject by employing procedures known in the art.

The pharmaceutical compositions described herein may be prepared, e.g., as described in *Remington: The Science and Practice of Pharmacy*, 20$^{th}$ Ed., 2003 (Lippincott Williams & Wilkins).

The pharmaceutical compositions may be, for example, capsules, tablets, aerosols, solutions, suspensions or products for topical application.

The route of administration may be any route which effectively transports the active compound to the appropriate or desired site of action. Suitable routes of administration include, but are not limited to, oral, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment). The oral route is preferred.

Solid oral formulations include, but are not limited to, tablets, capsules (soft or hard gelatin), dragees (containing the active ingredient in powder or pellet form), troches and lozenges. Tablets, dragees, or capsules having talc and/or a carbohydrate carrier or binder or the like are particularly suitable for oral application. Preferable carriers for tablets, dragees, or capsules include lactose, cornstarch, and/or potato starch. A syrup or elixir can be used in cases where a sweetened vehicle can be employed.

A typical tablet that may be prepared by conventional tabletting techniques may contain: (1) Core: Active compound (as free compound or salt thereof), colloidal silicon dioxide (AEROSIL®), microcrystalline cellulose (AVICEL®), modified cellulose gum (AC-DI-SOL®), and magnesium stearate; (2) Coating: HPMC, Mywacett 9-40 T and acylated monoglyceride.

Liquid formulations include, but are not limited to, syrups, emulsions, soft gelatin and sterile injectable liquids, such as aqueous or non-aqueous liquid suspensions or solutions.

For parenteral application, particularly suitable are injectable solutions or suspensions, preferably aqueous solutions with the active compound dissolved in polyhydroxylated castor oil.

Methods of Treatment

The present invention provides compounds and pharmaceutical formulations thereof that are useful in the treatment of diseases, conditions and/or disorders mediated by viral infections. The connection between therapeutic effect and antiviral is illustrated. For example, PCT publication Nos. WO 01//07646, WO 01/65957, or WO 03/037908; US publication Nos. U.S. Pat. No. 4,598,095 or US 2002/0068757; EP publication Nos. EP0989862 or EP 0724650; *Bioorganic & Medicinal Chemistry Letters*, 16, (6), 1712-1715, 2006; and references cited therein, all of which are incorporated herein by reference in their entirety and for the purpose stated.

The present patent application further provides a method of treating a disease, condition and/or disorder mediated by viral infections in a subject in need thereof by administering to the subject a therapeutically effective amount of a compound or a pharmaceutical composition of the present invention.

Diseases, conditions, and/or disorders that are mediated by viral infections are believed to include, but are not limited to, HIV infection, HBV, HCV, a retroviral infection genetically related to HIV, AIDS, or respiratory disorders (including adult respiratory distress syndrome (ARDS).

The compounds of the present invention can also obtain synergistic effects in the prevention or treatment of the above diseases when used suitably in combination with existing drugs. The administered dose may be decreased in comparison with administration of either drug alone, and in addition adverse effects of co-administered drugs can be avoided or reduced.

Methods of Preparation

The compounds described herein may be prepared by techniques known in the art. In addition, the compounds described herein may be prepared by following the reaction sequence as depicted in Scheme-1. The compounds of Formula G can be prepared by the procedure as described in our co-pending PCT application PCT/IB2010/001677 filed on 5 Jul. 2010. Further, in the following scheme, where specific reagents, solvents, coupling agents, etc., are mentioned, it is understood that other reagents, solvents, coupling agents etc., known in the art may also be used and are therefore included within the present invention. Variations in reaction conditions, for example, temperature and/or duration of the reaction, which may be used as known in the art, are also within the scope of the present invention. All the stereo isomers of the salt compounds in this scheme, unless otherwise specified, are also encompassed within the scope of this invention.

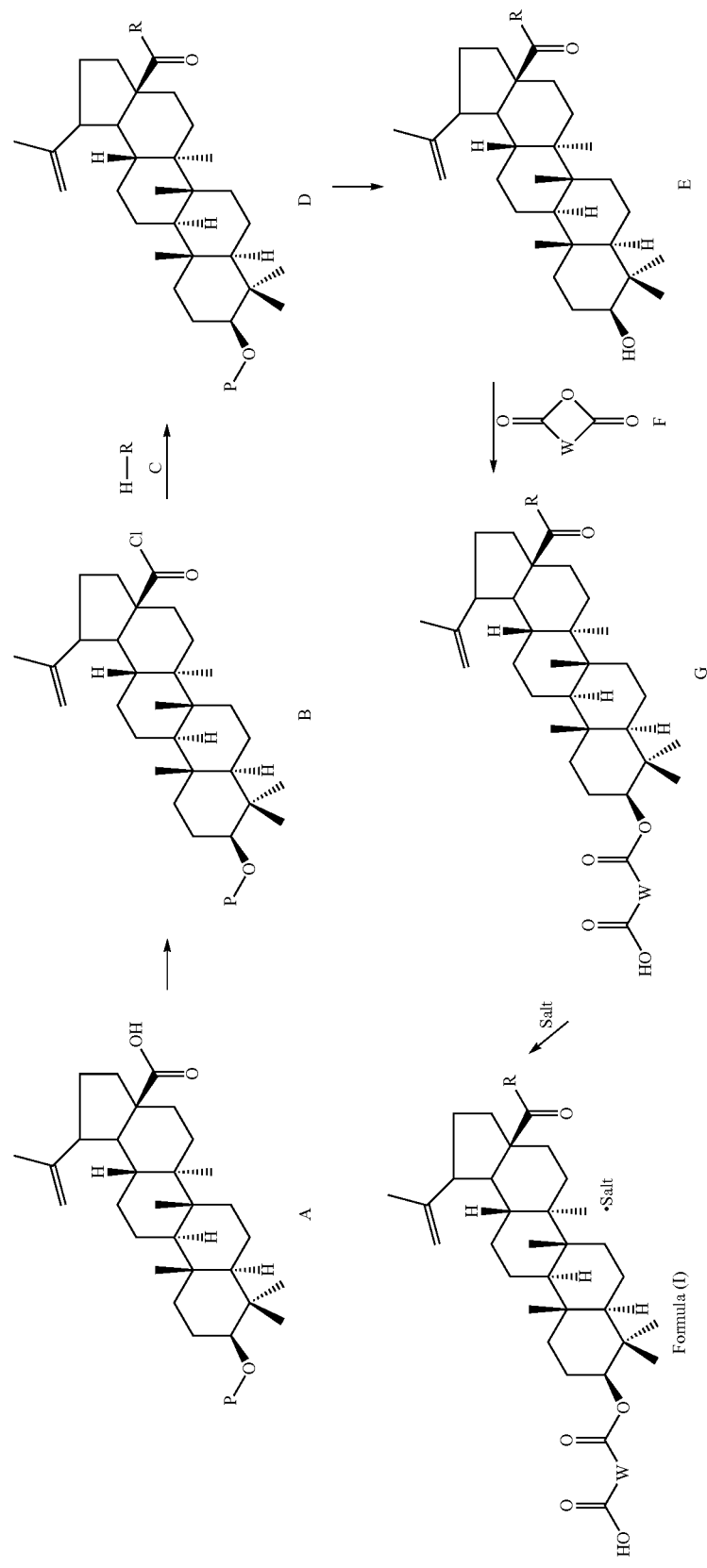
Scheme-1

The compounds of Formula (I) can be prepared by the procedure as shown in Scheme 1. The C-3 hydroxy-protected compounds of formula A can be converted to C-28 carboxylic halide of the C-3 oxy-protected compounds of formula B in presence of halogenating agents such as thionyl chloride, oxalyl chloride, phosphorous bromide, phosphorous oxy bromide or the like can be performed in an inert solvent like benzene or DCM or the like without added solvent. C-28 carboxylic halide of the C-3 oxy-protected compounds of formula B can be reacted with the amine compounds of formula C in the presence of triethyl amine or the like in an inert solvents such as DCM or the like to give the O-protected compounds of formula D. The O-protected compounds of formula D can be hydrolyzed to give the hydroxyl compounds of formula E by hydrolyzing with a base like metal hydroxide, metal carbonates or bicarbonates and the like in a protic solvent like alcohol or a combination of solvents for example, MeOH:THF or the like. The 3-hydroxy compounds of formula E can be reacted with acid of formula F or partially protected diacids or mixed anhydrides, acid halides to give the compound of formula G in the presence a base like triethyl amine, 4-Dimethylaminopyridine, diisopropyl ethyl mine or pyridine or the like in the solvents such as for example, DCM, toluene, THF, pyridine or the like. Compounds of formula (I) can be prepared by dissolving compound of formula G in an inert solvent at temperature in the range of 0-80° C. and then adding the appropriate base either neat or as a solution and isolating the solid salt. The salt may be isolated by cooling the reaction solution and optionally seeding the solution with the desired product and/or concentrating the solution. Optionally the product may be isolated by adding an anti-solvent to a solution of the product in an inert solvent. The solid may be collected by methods known in the art. For example, filtration or centrifugation.

Experimental

The present invention is further illustrated by the following examples, which are not to be construed in any way as imposing limitations upon the scope of this disclosure, but rather are intended to be illustrative only. On the contrary, it is to be clearly understood that resort may be had to various other embodiments, modifications, and equivalents thereof which, after reading the description herein, may suggest themselves to one of ordinary skill in the art without departing from the spirit of the present invention. Thus, the skilled artisan will appreciate how the experiments and Examples may be further implemented as disclosed by variously altering the following examples, substituents, reagents, or conditions.

EXAMPLES

Example 1

Preparation of arginine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid

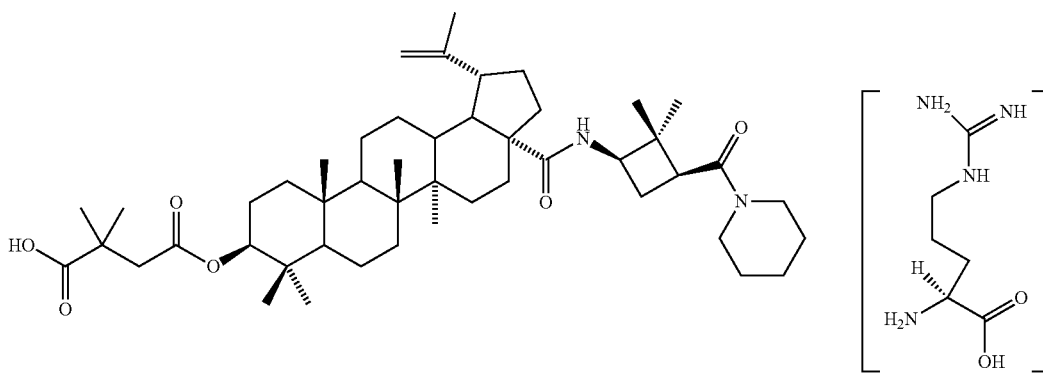

500 mg of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid was dissolved in 10 ml ethanol then 118 mg of solid Arginine was added which was dissolved in 1 ml of Deionised water and stirred until a clear solution was obtained. The reaction mixture was heated at 50-60° C. for 15-30 minutes and cooled to 30-40° C. The ethanol mixture was concentrated with a stream of nitrogen. Solid was formed which was filtered followed by vacuum dried for overnight IR [cm$^{-1}$]: 3373, 3179, 2947, 1638, 1529, 1472, 1402, 1365, 1252, 1193, 1136, 1148, 978, 881.

Example 2

Preparation of amino guanidine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid

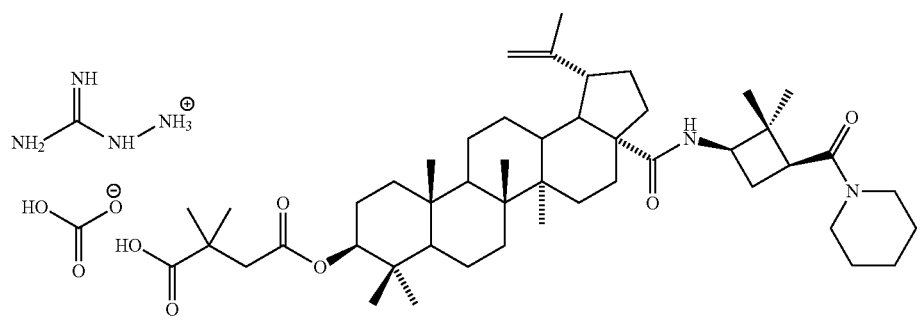

500 mg of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid was dissolved in 10 ml methanol then 87 mg of Amino guanidine bicarbonate salt was dissolved in methanol by heating at 80° C. The solution was stirred to obtain a clear mixture at 50-65° C. and stirred for 15 minutes then cooled to 40° C. The methanol mixture was concentrated with a stream of nitrogen gas to form solid. The obtained solid was charged with 10 ml diethyl ether and stirred for 30 minutes. Solvent was evaporated, filtered and dried by vacuum for overnight. IR[cm$^{-1}$]: 3436, 3360, 3327, 2945, 2867, 1679, 1631, 1533, 1472, 1445, 1400, 1369, 1219, 1147, 1022, 978, 881; $^1$H NMR (300 MHz, CD3OD): 0.82-0.96 (m, 18H), 1.24-1.67 (30H), 1.94-1.98 (m, 5H), 2.26-2.57 (m, 18H), 2.86-2.89 (m, 1H), 3.11 (m, 1H), 3.41-3.71 (m, 5H), 4.10-4.13 (m, 1H), 4.45-4.58 (m, 1H), 4.72 (s, 1H), 4.8 (s, 1H), 5.95-5.97 (d, 1H, J=9 Hz), 7.79 (brs, 1H).

Example 3

Preparation of calcium salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid 500 mg of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid was dissolved in 10 ml of methanol then 0.035 gm of CaCl$_2$ in 1 ml of distilled water was added and the mixture was stirred till it become clear at 50-60° C. and cooled it to 40° C. The methanol mixture was concentrated with a stream of nitrogen gas to form a clear solid and it was charged with 10 ml of diethyl ether then the mixture was stirred for 30 minutes. The solvent was evaporated, filtered and dried through vacuum for overnight. IR [cm$^{-1}$]: 3401, 2946, 1733, 1611, 1475, 1449, 1253, 1193, 1022, 978. $^1$H NMR (300 MHz, CDCl$_3$): δ 6.01 (d, 1H, J=8.4 Hz), 4.72 (s, 1H), 4.58 (s, 1H), 4.53-4.43 (m, 1H), 4.16-4.08 (m, 1H), 3.71-3.62 (m, 2H), 3.54-3.35 (m, 3H), 3.18-3.06 (m, 1H), 2.93-2.87 (m, 1H), 2.66 (d, 1H, J=15.9 Hz), 2.56 (d, 1H, J=15.9 Hz), 2.50-2.27 (m, 2H), 1.99-1.88 (m, 2H), 1.80-1.00 (m, 46H), 0.94, 0.92, 0.83 (s, 12H).

Example 4

Preparation of choline salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid

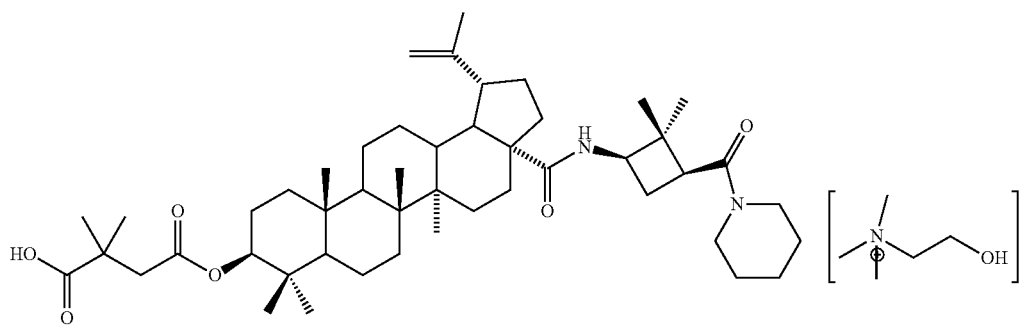

500 mg of 4-((1R,3aR,5aR,5bR,9S,11aR)-3a-41R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid was dissolved in 10 ml of ethanol then 82 mg or 0.2 ml of liquid Choline hydroxide in 10 ml of Deionised water was added and the solution was stirred until the mixture become clear at 50-60° C. for 15-30 minutes and cooled to 30-40° C. The ethanol mixture was concentrated with a stream of nitrogen to form solid. The solid was filtered and dried under vacuum by overnight. IR [cm$^{-1}$]: 3413, 2950, 1711, 1652, 1638, 1566, 1474, 1401, 1233, 1134, 1087, 956; $^1$H NMR (300 MHz, CD3OD): 0.970-1.0, (m, 12H), 1.01-1.18 (m, 6H), 1.20-1.89 (m, 38H), 2.05-2.18 (m, 4H), 2.45-2.48 (m, 1H), 2.515-2.540 (m, 4H), 2.66 (m, 2H), 2.99-3.05 (m, 3H), 3.467-3.526 (d, 8H), 3.59-3.68 (d, 1H), 3.97-4.02 (m, 5H), 4.09 (t, 1H), 4.42 (m, 1H), 4.57 (s, 1H), 4.69 (s, 1H), 7.56-7.59 (d, 1H, J=9 Hz).

Example 5

Preparation of dicyclohexylamine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid

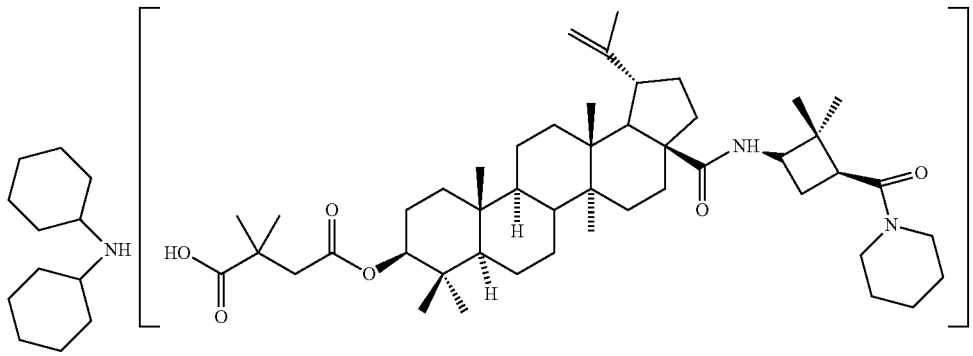

500 mg of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid was dissolved in 10 ml of methanol then 117 mg of liquid Dicyclohexylamine in 1 ml of Deionised water was added and stirred to obtain a clear mixture at 50-65° C. for 15 minutes and cool to 40° C. The methanol mixture was concentrated with a stream of nitrogen gas to form solid. The obtained solid was charged with 10 ml diethyl ether and stirred for 30 minutes. Solvent was evaporated, filtered and dried by vacuum for overnight. IR [cm$^{-1}$]: 3370, 2942, 2862, 2463, 1729, 1623, 1561, 1509, 1467, 1450, 1392, 1365, 1252, 1231, 1192, 1148, 1128, 1022, 978, 880, 766, 545;

Example 6

Preparation of diethanolamine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid

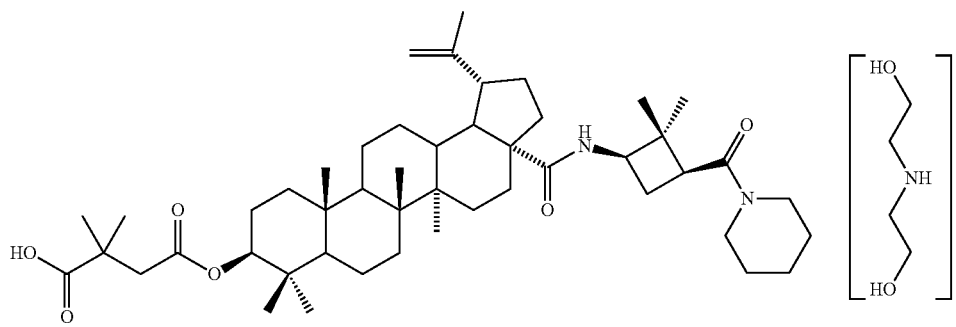

500 mg of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid was dissolved in 10 ml methanol then 72 mg or 0.1 ml of liquid Diethanolamine in 1 ml of Deionised water was added and the solution was stirred at 50-60° C. for 15-30 minutes and cooled to 30-40° C. After the mixture become clear, the methanol mixture was concentrated with a stream of nitrogen to obtain solid which was filtered and dried by vacuum for overnight. IR [cm$^{-1}$]: 3367, 2941, 2866, 2343, 2368, 1719, 1618, 1558, 1459, 1405, 1364, 1252, 1068, 881; $^1$H NMR (300 MHz, CD3OD): 0.86-1.01 (m, 24H), 1.13-1.68 (m, 36H), 1.84-1.89 (m, 6H), 2.05-2.09 (m, 2H), 2.45-2.99 (m, 7H), 3.06-3.47 (m, 5H), 4.09-4.1 (m, 2H), 4.1 (m, 1H), 4.12 (m, 1H), 4.57 (s, 1H), 4.69 (s, 1H), 7.56-7.59 (d, 1H, J=9 Hz).

Example 7

Preparation of 2,6-dimethyl piperazine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid

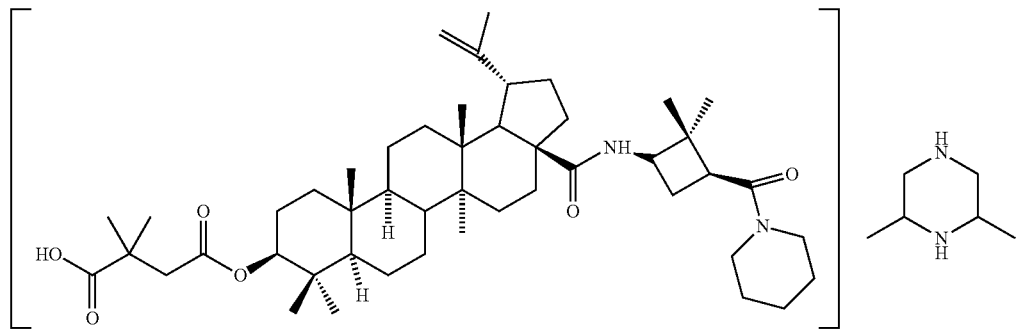

500 mg of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid was dissolved in 10 ml of methanol then 73.7 mg of 2,6-dimethyl Piperazine solid in 1 ml of Deionised water was added the solution was stirred to obtain a clear solution at 50-60° C. for 30 minutes and cooled to 40° C. The methanol solvent was concentrated with nitrogen gas to form a clear solid. The obtained solid was charged in 10 ml of diethyl ether and the solid was dissolved. Solvent was evaporated, filtered and dried under vacuum overnight. IR [cm$^{-1}$]: 3455, 3396, 2945, 2866, 1725, 1630, 1509, 1467, 1455, 1391, 1367, 1252, 1230, 1192, 1136, 979, 881; $^1$H NMR (300 MHz, CD3OD): 0.80-0.95 (m, 24H), 1.11-1.80 (m, 32H), 1.94-1.98 (m, 2H), 2.2-2.59 (m, 8H), 2.88-2.91 (m, 1H), 3.07-3.11 (m, 5H), 3.39-3.71 (m, 13H), 4.10-4.12 (m, 1H), 4.44-4.47 (m, 1H), 4.47 (s, 1H), 4.58 (s, 1H), 5.93-5.96 (d, 1H, J=9 Hz).

Example 8

Preparation of lithium salt of 4-((1R,3aR,5aR,5bR,9S,11aR)-3a-((1R,1S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid

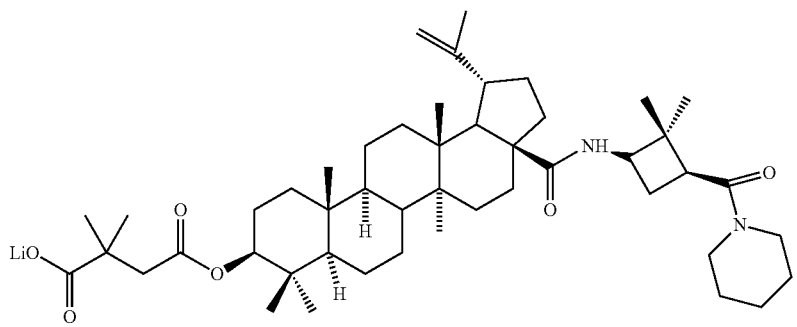

500 mg of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid was dissolved in 10 ml of methanol then 0.027 gm of solid Lithium hydroxide in 1 ml of Deionised water was added and the solution was stirred at 50-60° C. for 30 minutes and cooled to 30-40° C. The methanol mixture was concentrated with a stream of nitrogen gas. A clear solid was obtained which was charged and dissolved in 10 ml of diethyl ether. The solvent was evaporated and the obtained solid was filtered & dried under vacuum overnight. IR [cm$^{-1}$]: 3403, 2946, 2866, 1719, 1622, 1444, 1370, 1230, 1136, 1022, 979, 883; $^1$H NMR (300 MHz, CD3OD): 0.87-0.95 (m, 18H), 1.16-2.05 (m, 37H), 2.18-2.54 (m, 9H), 2.86-2.91 (m, 2H), 3.09-3.12 (m, 1H), 3.41-3.46 (m, 3H), 3.71-3.74 (m, 1H), 4.10-4.13 (m, 1H), 4.58-4.73 (m, 1H), 5.91 (s, 1H), 5.94 (d, 1H, J=9 Hz).

Example 9

Preparation of lysine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid

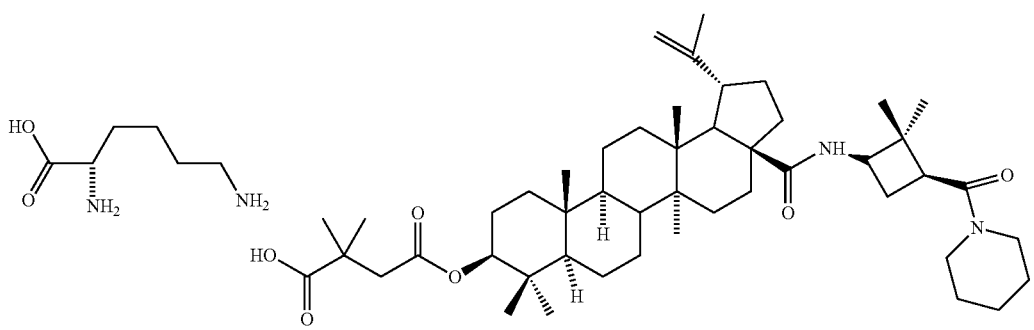

500 mg of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid was dissolved in 10 ml of methanol then 94.3 mg of L-lysine solid in 0.5 ml of Deionised water was added and the solution was stirred. A clear solution was formed after stirring for 10 minutes and charged with 10 ml methanol. The reaction mixture was heated to 50-60° C. for 30 minutes and cooled to 30-40° C. The methanol mixture was concentrated with a stream of nitrogen gas. A clear solid was obtained which was charged and dissolved in 10 ml of diethyl ether then the solvent was evaporated. The obtained solid was filtered & dried under vacuum for overnight. IR [cm$^{-1}$]: 3402, 2946, 2869, 1729, 1623, 1523, 1470, 1444, 1397, 1365, 1229, 1136, 1021, 879; $^1$H NMR (300 MHz, CD3OD): 0.84-0.95 (m, 23H), 1.12-1.67 (m, 38H), 1.89-1.96 (m, 14H), 2.17-2.22 (m, 1H), 2.23-2.59 (m, 2H), 2.89-3.11 (m, 2H), 3.12-3.23 (m, 1H), 3.41-3.47 (m, 3H), 3.71-3.80 (m, 1H), 4.10 (m, 1H), 4.46 (m, 1H), 4.57 (s, 1H), 4.72 (s, 1H), 6.04 (s, 1H).

Example 10

Preparation of magnesium salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid

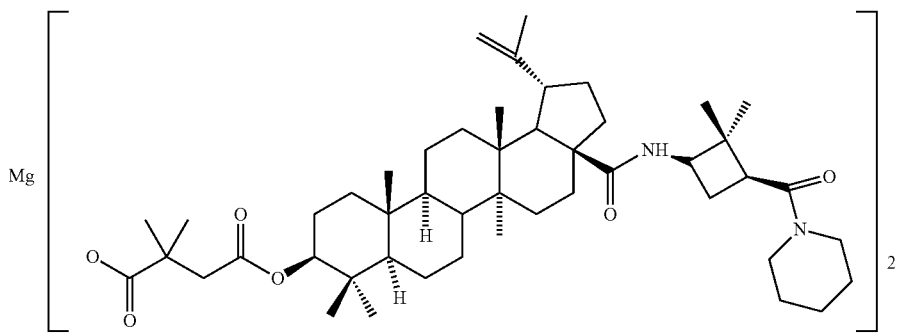

500 mg of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid was dissolved in 10 ml of methanol then 18 mg of magnesium hydroxide solid in 2 ml of Deionised water was added and the solution was stirred. A clear solution was formed after stirring for 30 minutes and charged with 10 ml methanol. The reaction mixture was heated to 50-60° C. for 30 minutes and cooled to 30-40° C. The methanol mixture was concentrated with a stream of nitrogen gas. A clear solid was obtained which was dissolved in 10 ml of diethyl ether and the solvent was evaporated. The obtained solid was filtered & dried under vacuum for overnight. IR [cm$^{-1}$]: 3419, 2945, 1729, 1622, 1445, 1252, 1229, 1022, 979, 882; $^1$H NMR (300 MHz, CDCl$_3$): δ 6.01 (d, 1H, J=8.4 Hz), 4.72 (s, 1H), 4.58 (s, 1H), 4.53-4.43 (m, 1H), 4.16-4.08 (m, 1H), 3.71-3.62 (m, 2H), 3.54-3.35 (m, 3H), 3.18-3.06 (m, 1H), 2.93-2.87 (m, 1H), 2.66 (d, 1H, J=15.9 Hz), 2.56 (d, 1H, J=15.9 Hz), 2.50-2.27 (m, 2H), 1.99-1.88 (m, 2H), 1.80-1.00 (m, 46H), 0.94, 0.92, 0.83 (s, 12H).

Example 11

Preparation of N-methyl glucamine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid

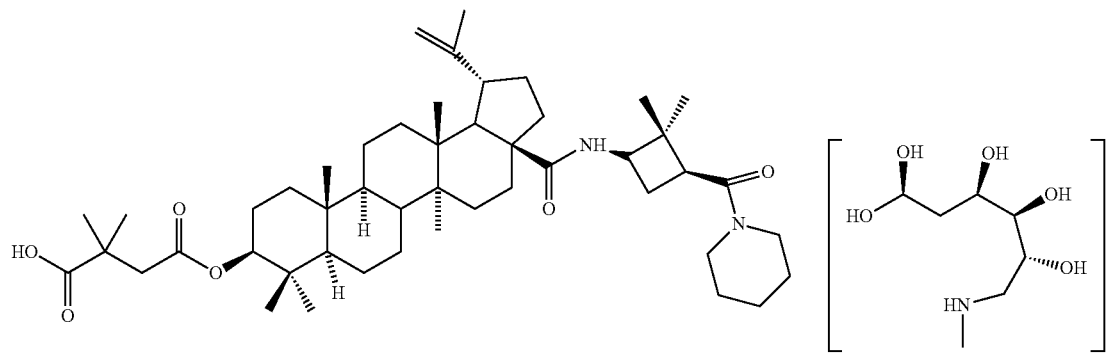

500 mg of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid was dissolved in 10 ml of methanol then 132 mg of N-methyl glucamine solid in 1 ml of Deionised water was added and the solution was stirred. A clear solution was formed after stirring for 30 minutes and charged with 10 ml methanol. The reaction mixture was heated to 50-60° C. for 30 minutes and cooled to 30-40° C. The methanol mixture was concentrated with a stream of nitrogen gas. A clear solid was obtained which was dissolved in 10 ml of diethyl ether. The solvent was evaporated and the obtained solid was filtered & dried under vacuum for overnight. IR [cm$^{-1}$]: 3400, 2945, 1723, 1628, 1561, 1558, 1550, 1459, 1446, 1368, 1253, 1041, 1023, 881; $^1$H NMR (300 MHz, CD$_3$OD): 0.78-1.04 (m, 32H), 1.14-1.90 (m, 36H), 2.01-2.25 (m, 2H), 2.48-2.68 (m, 7H), 2.99-3.83 (m, 14H), 4.02-4.04 (m, 2H), 4.57 (m, 1H), 4.69 (s, 1H), 4.7 (s, 1H), 7.4 (d, 1H).

Example 12

Preparation of N-octyl glucamine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid

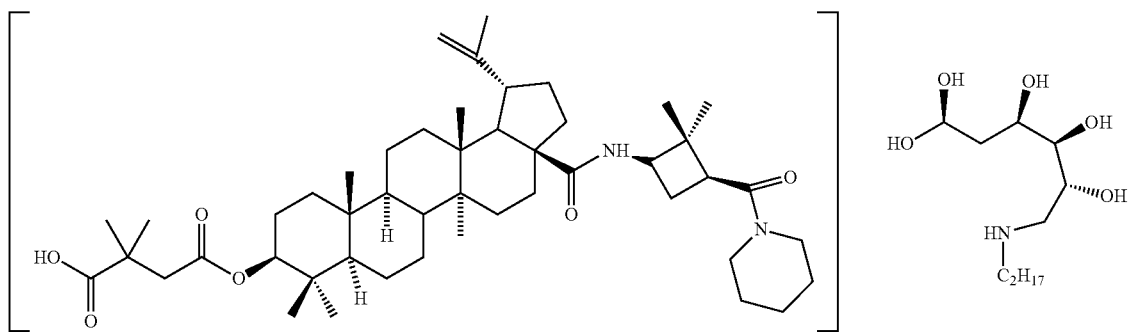

500 mg of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid was dissolved in 10 ml of methanol then 170.4 mg of N-octyl Glucamine solid in 1 ml of Deionised water was added and the solution was stirred. A clear solution was formed after stirring for 30 minutes and charged with 10 ml methanol. The reaction mixture was heated to 50-60° C. for 30 minutes and cooled to 30-40° C. The methanol mixture was concentrated with a stream of nitrogen gas. A clear solid was obtained which was charged and dissolved in 10 ml of diethyl ether. The solvent was evaporated and the obtained solid was filtered & dried under vacuum for overnight. IR [cm$^{-1}$]: 3410, 2943, 2863, 1724, 1620, 1459, 1365, 1230, 1131, 1022, 882, 772, 543.

Example 13

Preparation of piperazine salt of 4-((1R,3aR,5aR, 5bR,9S,11aR)-3a-((1R,3S)-2,2-dimethyl-3-(piperidine-1-carbonyl)cyclobutylcarbamoyl)-5a,5b,8,8, 11a-pentamethyl-1-(prop-1-en-2-yl)icosahydro-1H-cyclopenta[a]chrysen-9-yloxy)-2,2-dimethyl-4-oxobutanoic acid

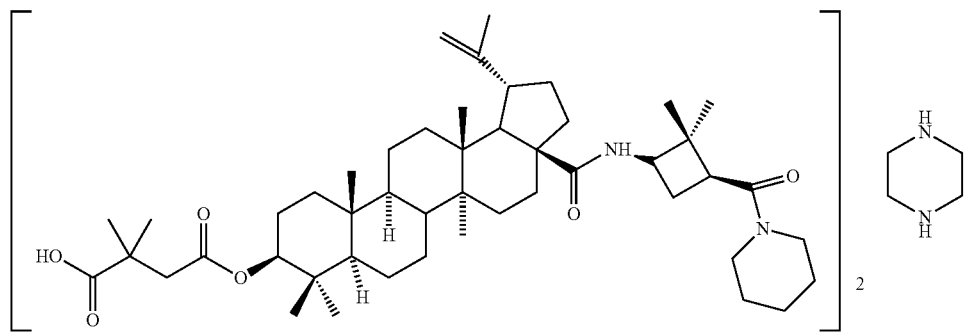

500 mg of 4-((1R,3aR,5aR,5bR,9S,11aR)-3a-((1R,3S)-2, 2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid was dissolved in 10 ml of methanol then 0.27 gm of piperazine solid in 1 ml of Deionised water was added and charged in stirred solution. The clear solution was formed after stirring for 30 minutes and charged with 10 ml methanol. The reaction mixture was heated to 50-60° C. for 30 minutes and cooled to 30-40° C. The methanol mixture was concentrated with a stream of nitrogen gas. A clear solid was obtained which was charged and dissolved in 10 ml of diethyl ether. The solvent was evaporated and the obtained solid was filtered & dried under vacuum for overnight. IR [cm$^{-1}$]: 3424, 2947, 2867, 1717, 1620, 1445, 1370, 1227, 1138, 1022, 980, 882; $^1$H NMR (300 MHz, CD3OD): 0.822-0.95 (m, 17H), 1.26-1.95 (m, 35H), 1.96-2.03 (m, 3H), 2.21-2.60 (m, 6H), 2.88-3.02 (m, 1H), 3.03-3.46 (m, 14H), 3.49-3.74 (m, 5H), 4.09-4.12 (m, 1H), 4.45 (m, 1H), 4.57 (s, 1H), 4.72 (s, 1H), 5.95-5.98 (d, 1H, J=9 Hz).

Example 14

Preparation of phenyl glycine methyl ester salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid

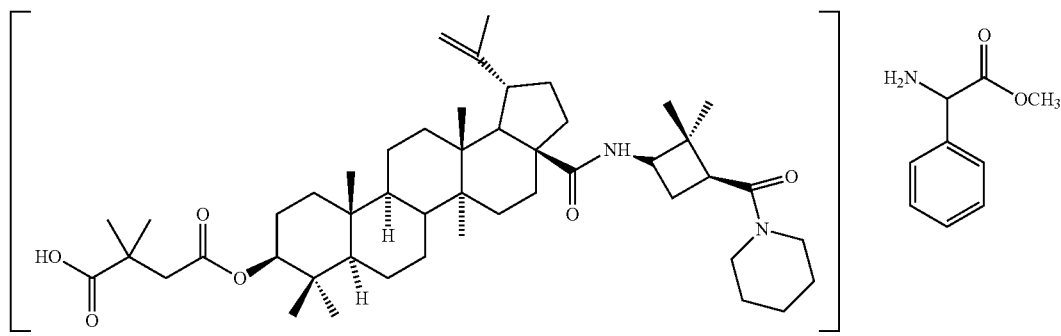

500 mg of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid was dissolved in 10 ml of methanol then 130 mg of (S)-(+) Phenyl Glycine methyl ester hydrochloride solid in 1 ml of Deionised water was added and charged in stirred solution. A clear solution was formed after stirring for 30 minutes and charged with 10 ml methanol. The reaction mixture was heated to 50-60° C. for 30 minutes and cooled to 30-40° C. The methanol mixture was concentrated with a stream of nitrogen gas. A clear solid was obtained which was dissolved in 10 ml of diethyl ether. The solvent was evaporated and the obtained solid was filtered & dried under vacuum for overnight. IR [cm$^1$]: 3401, 2945, 2866, 2628, 1737, 1637, 1604, 1509, 1505, 1473, 1447, 1368, 1350, 1249, 1191, 1143, 1022, 978, 883, 854, 728, 693, 543, 498; H$^1$ NMR in CD3OD: 0.85-1.01 (m, 22H), 1.19-2.99 (m, 45H), 3.0-3.05 (t, 2H), 3.47-3.66 (m, 4H), 3.80 (s, 3H), 4.09-4.12 (q, 1H), 4.44-4.46 (q, 1H), 4.57 (s, 1H), 4.69 (s, 1H), 5.19 (s, 1H), 7.48-7.49 (s, 5H).

Example 15

Preparation of phenyl glycinol salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid

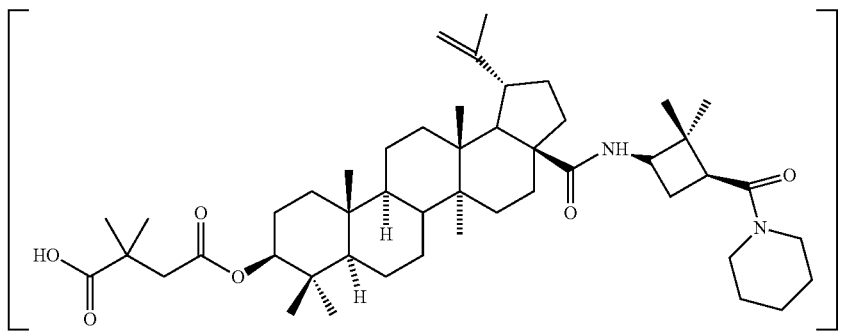

500 mg of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid was dissolved in 10 ml of methanol then 88.4 mg of (S)-Phenyl Glycinol methyl ester hydrochloride solid in 1 ml of Deionised water was added in stirred solution. A clear solution was formed after stirring for 30 minutes and charged with 10 ml methanol. The reaction mixture was heated to 50-60° C. for 30 minutes and cooled to 30-40° C. The methanol mixture was concentrated with a stream of nitrogen gas. A clear solid was obtained which was charged and dissolved in 10 ml of diethyl ether. The solvent was evaporated and the obtained solid was filtered & dried under vacuum for overnight. IR [cm$^{-1}$]: 3405, 3945, 3866, 1725, 1630, 1529, 1471, 1365, 1253, 1227, 1135, 1023, 979, 881, 761, 701, 543; H$^1$ NMR in CD3OD: 0.71-0.96 (m, 19H), 1.12-1.76 (m, 38H), 1.95-1.99 (q, 2H), 2.18-2.6 (m, 5H), 2.86-2.88 (t, 1H), 3.11-3.12 (t, 1H), 3.35-3.77 (m, 12H), 4.10-4.13 (q, 1H), 4.40 (brs, 1H), 4.42-4.58 (t, 1H), 4.58-4.72 (t, 1H), 5.93-5.96 (d, 1H), 7.36-7.37 (s, 5H, J=3 Hz).

Example 16

Preparation of potassium salt of 4-((1R,3aR,5aR, 5bR,9S,11aR)-3a-((1R,3S)-2,2-dimethyl-3-(piperi- dine-1-carbonyl)cyclobutylcarbamoyl)-5a,5b,8,8, 11a-pentamethyl-1-(prop-1-en-2-yl)icosahydro-1H- cyclopenta[a]chrysen-9-yloxy)-2,2-dimethyl-4- oxobutanoic acid

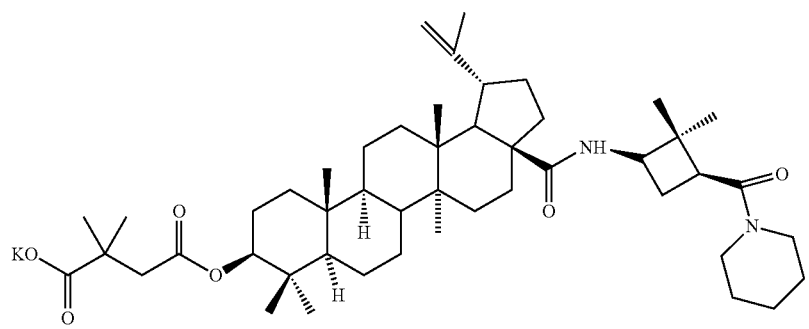

1 gm of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid was dissolved in 20 ml of methanol then 90 mg of solid potassium hydroxide in 1.5 ml of Deionised water was added in stirred solution. Clear solution was formed after stirring for 30 minutes. The reaction mixture was heated to 50-60° C. for 30 minutes and cooled to 30-40° C. The methanol mixture was concentrated with a stream of nitrogen gas. A clear solid was obtained which was dissolved in 15 ml of diethyl ether. The solvent was evaporated and the obtained solid was filtered & dried under vacuum for overnight. IR [cm$^{-1}$]: 3411, 2945, 2867, 1719, 1634, 1631, 1459, 1445, 1404, 1368, 1252, 1230, 1022, 882; $^1$H NMR (300 MHz, CDCl$_3$): δ 6.01 (d, 1H, J=8.4 Hz), 4.72 (s, 1H), 4.58 (s, 1H), 4.53-4.43 (m, 1H), 4.16-4.08 (m, 1H), 3.71-3.62 (m, 2H), 3.54-3.35 (m, 3H), 3.18-3.06 (m, 1H), 2.93-2.87 (m, 1H), 2.66 (d, 1H, J=15.9 Hz), 2.56 (d, 1H, J=15.9 Hz), 2.50-2.27 (m, 2H), 1.99-1.88 (m, 2H), 1.80-1.00 (m, 46H), 0.94, 0.92, 0.83 (s, 12H).

Example 17

Preparation of sodium salt of 4-((1R,3aR,5aR,5bR, 9S,11aR)-3a-((1R,3S)-2,2-dimethyl-3-(piperidine-1- carbonyl)cyclobutylcarbamoyl)-5a,5b,8,8,11a-pen- tamethyl-1-(prop-1-en-2-yl)icosahydro-1H- cyclopenta[a]chrysen-9-yloxy)-2,2-dimethyl-4- oxobutanoic acid

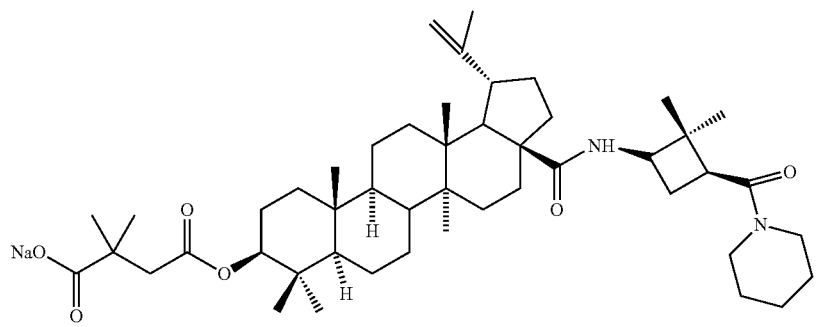

1 gm of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid was dissolved in 20 ml of methanol then 54 mg of solid sodium hydroxide in 1.5 ml of Deionised water was added in stirred solution. Clear solution was formed after stirring for 30 minutes. The reaction mixture was heated to 50-60° C. for 30 minutes and cooled to 30-40° C. The methanol mixture was concentrated with a stream of nitrogen gas. A clear solid was obtained which was dissolved in 15 ml of diethyl ether. The solvent was evaporated and the obtained solid was filtered & dried under vacuum for overnight. IR [cm$^{-1}$]: 3432, 2948, 2866, 1719, 1619, 1569, 1473, 1446, 1369, 1252, 1232, 1022, 980, 883, 544; $^1$H NMR (300 MHz, CDCl$_3$): δ 6.01 (d, 1H, J=8.4 Hz), 4.72 (s, 1H), 4.58 (s, 1H), 4.53-4.43 (m, 1H), 4.16-4.08 (m, 1H), 3.71-3.62 (m, 2H), 3.54-3.35 (m, 3H), 3.18-3.06 (m, 1H), 2.93-2.87 (m, 1H), 2.66 (d, 1H, J=15.9 Hz), 2.56 (d, 1H, J=15.9 Hz), 2.50-2.27 (m, 2H), 1.99-1.88 (m, 2H), 1.80-1.00 (m, 46H), 0.94, 0.92, 0.83 (s, 12H).

Example 18

Preparation of Tris(hydroxymethyl)aminomethane salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid

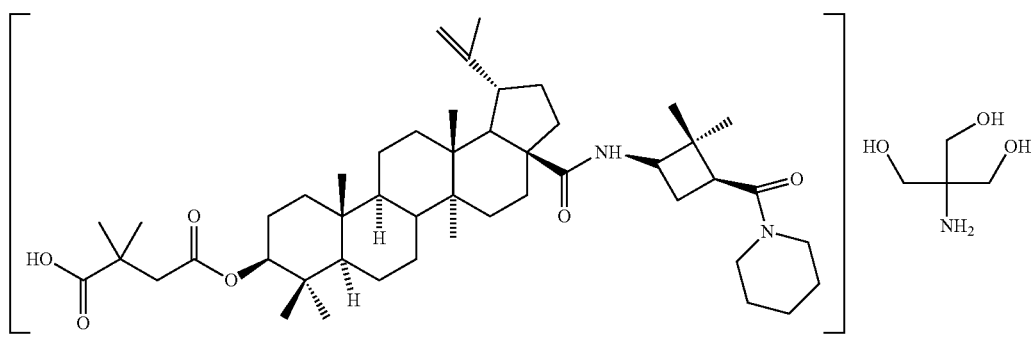

500 mg of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid was dissolved in 10 ml of methanol then 78.19 mg of Tris(hydroxymethyl)aminomethane solid in 1 ml of Deionised water was added and charged in stirred solution. Clear solution was formed after stirring for 30 minutes. The reaction mixture was heated to 50-60° C. for 30 minutes and cooled to 30-40° C. The methanol mixture was concentrated with a stream of nitrogen gas. A clear solid was obtained which was dissolved in 15 ml of diethyl ether. The solvent was evaporated and the obtained solid was filtered & dried under vacuum for overnight. IR [cm$^{-1}$]: 3387, 2954, 2867, 1714, 1631, 1595, 1541, 1463, 1400, 1360, 1254, 1213, 1128, 1026, 880, 544; H$^1$ NMR in CD3OD: 0.8-0.95 (m, 21H), 1.25-1.67 (m, 39H), 1.95-1.98 (t, 1H), 2.21-2.6 (m, 7H), 2.86-2.91 (t, 1H), 3.09-3.70 (m, 13H), 4.10-4.12 (q, 1H), 4.43-4.45 (t, 1H), 4.57 (s, 1H), 4.72 (s, 1H), 5.96-5.99 (d, 1H, J=9 Hz).

Example 19

Preparation of sodium salt of 4-((1R,3aS,5aS,7aR,9S,11aR,11bS,13aR)-3a-((1S,3S)-2,2-dimethyl-3-(pyrrolidine-1-carbonyl)cyclobutylcarbamoyl)-5a,8,8,11a,13a-pentamethyl-1-(prop-1-en-2-yl)icosahydro-1H-cyclopenta[a]chrysen-9-yloxy)-2,2-dimethyl-4-oxobutanoic acid

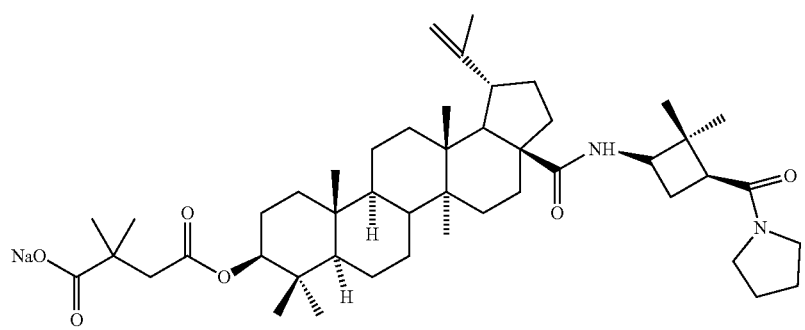

500 mg of 4-((1R,3aS,5aS,7aR,9S,11aR,11bS,13aR)-3a-((1S,3S)-2,2-dimethyl-3-(pyrrolidine-1-carbonyl)cyclobutylcarbamoyl)-5a,8,8,11a,13a-pentamethyl-1-(prop-1-en-2-yl)icosahydro-1H-cyclopenta[a]chrysen-9-yloxy)-2,2-dimethyl-4-oxobutanoic acid was dissolved in 12 ml of methanol then 26 mg of solid NaOH in 1 ml of Deionised water was added and charged in stirred solution. Clear solution was formed after stirring for 30 minutes. The reaction mixture was heated to 50-60° C. for 30 minutes and cooled to 30-40° C. The methanol mixture was concentrated with a stream of nitrogen gas. A clear solid was obtained which was charged in 10 ml of diethyl ether. The solvent was evaporated and the obtained solid was filtered & dried under vacuum for overnight. $^1$H NMR (300 MHZ, CDCl$_3$): δ 6.42 (1H, d, J=8.1 Hz), 4.72 (1H, s), 4.5787 (1H, s), 4.51 (1H, m), 4.1 (1H, m), 3.42-3.5 (3H, m), 3.3-3.4 (1H, m), 3.08-3.15 (1H, m), 2.8 (1H, m), 2.2-2.7 (7H, m), 1.8-2.0 (11H, m), 1.2-1.78 (24H, m), 0.95 (6H, m), 0.8 (10H, m).

Example 20

Preparation of potassium salt of 4-((1R,3aS,5aS,7aR,9S,11aR,11b S,13aR)-3a-((1S,3S)-2,2-dimethyl-3-(pyrrolidine-1-carbonyl)cyclobutylcarbamoyl)-5a,8,8,11a,13a-pentamethyl-1-(prop-1-en-2-yl)icosahydro-1H-cyclopenta[a]chrysen-9-yloxy)-2,2-dimethyl-4-oxobutanoic acid

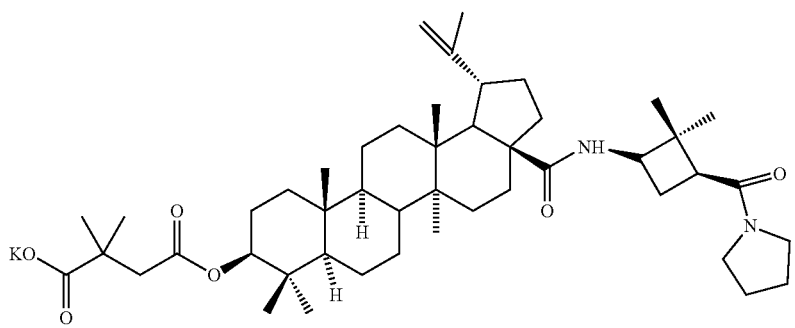

500 mg of 4-((1R,3aS,5aS,7aR,9S,11aR,11bS,13aR)-3a-((1S,3S)-2,2-dimethyl-3-(pyrrolidine-1-carbonyl)cyclobutylcarbamoyl)-5a,8,8,11a,13a-pentamethyl-1-(prop-1-en-2-yl)icosahydro-1H-cyclopenta[a]chrysen-9-yloxy)-2,2-dimethyl-4-oxobutanoic acid was dissolved in 12 ml of methanol then 36 mg of solid KOH in 1 ml of Deionised water was added in stirred solution. Clear solution was formed after stirring for 30 minutes. The reaction mixture was heated to 50-60° C. for 30 minutes and cooled to 30-40° C. The methanol mixture was concentrated with a stream of nitrogen gas. A clear solid was obtained which was dissolved in 10 ml of diethyl ether. The solvent was evaporated and the obtained solid was filtered & dried under vacuum for overnight. IR [cm⁻¹]: 3410, 2950, 2871, 1719, 1625, 1575, 1451, 1400, 1365, 1225, 1132, 979, 880; $^1$H NMR (300 MHZ, CDCl$_3$): δ 6.42 (1H, d, J=8.1 Hz), 4.72 (1H, s), 4.5787 (1H, s), 4.51 (1H, m), 4.1 (1H, m), 3.42-3.5 (3H, m), 3.3-3.4 (1H, m), 3.08-3.15 (1H, m), 2.8 (1H, m), 2.2-2.7 (7H, m), 1.8-2.0 (11H, m), 1.2-1.78 (24H, m), 0.95 (6H, m), 0.8 (10H, m).

Example 21

Preparation of N-methyl glucamine salt of 4-((1R,3aS,5aS,7aR,9S,11aR,11bS,13aR)-3a-((1S,3S)-2,2-dimethyl-3-(pyrrolidine-1-carbonyl)cyclobutylcarbamoyl)-5a,8,8,11a,13a-pentamethyl-1-(prop-1-en-2-yl)icosahydro-1H-cyclopenta[a]chrysen-9-yloxy)-2,2-dimethyl-4-oxobutanoic acid

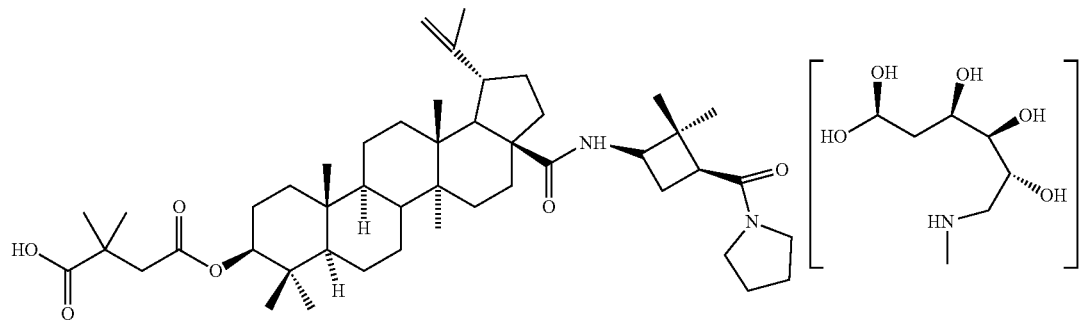

500 mg of 4-((1R,3aS,5aS,7aR,9S,11aR,11bS,13aR)-3a-((1S,3S)-2,2-dimethyl-3-(pyrrolidine-1-carbonyl)cyclobutylcarbamoyl)-5a,8,8,11a,13a-pentamethyl-1-(prop-1-en-2-yl)icosahydro-1H-cyclopenta[a]chrysen-9-yloxy)-2,2-dimethyl-4-oxobutanoic acid was dissolved in 12 ml of methanol then 0.12 mg of solid N-methyl glucamine in 1 ml of Deionised water was added in stirred solution. Clear solution was formed after stirring for 30 minutes. The reaction mixture was heated to 50-60° C. for 30 minutes and cooled to 30-40° C. The methanol mixture was concentrated with a stream of nitrogen gas. A clear solid was obtained which dissolved in 10 ml of diethyl ether. The solvent was evaporated and the obtained solid is filtered & dried under vacuum for overnight.

Example 22

Preparation of arginine salt of (1R,5bS,9S,11aR)-9-((1R,3S)-3-carboxy-2,2-dimethylcyclobutanecarbonyloxy)-5b,8,8,11a-tetramethyl-1-(prop-1-en-2-yl)icosahydro-1H-cyclopenta[a]chrysene-3a-carboxylic acid

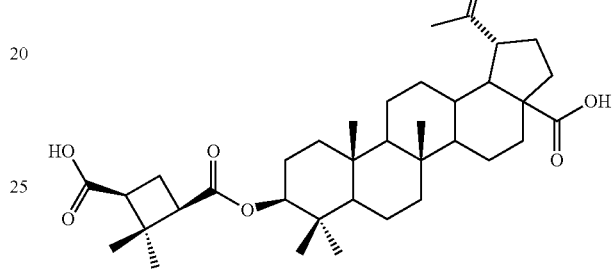

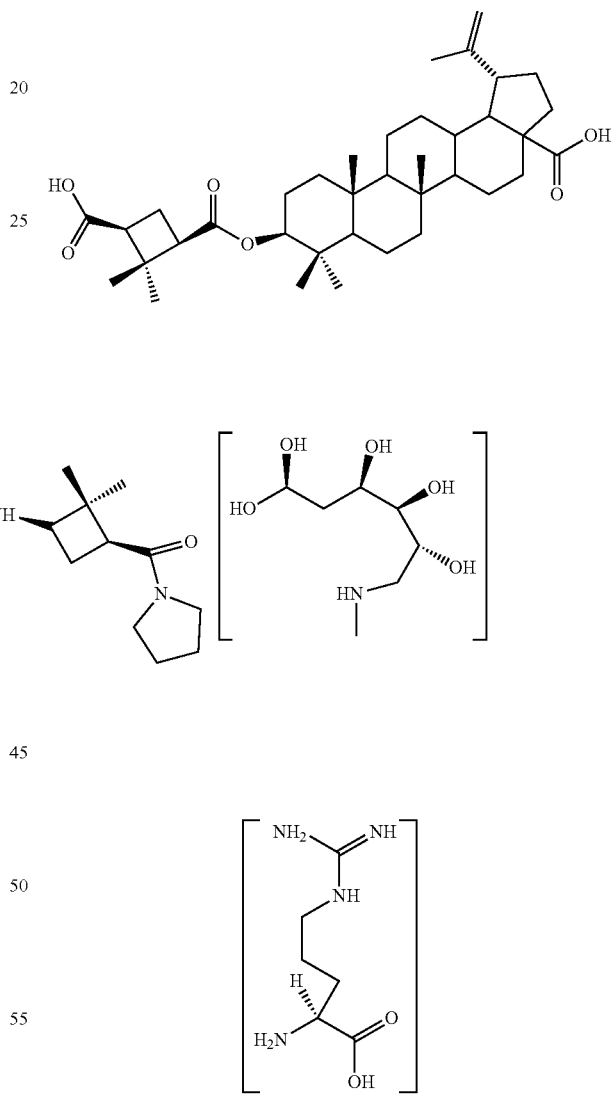

500 mg of (1R,5bS,9S,11aR)-9-((1R,3S)-3-carboxy-2,2-dimethylcyclobutanecarbonyloxy)-5b,8,8,11a-tetramethyl-1-(prop-1-en-2-yl)icosahydro-1H-cyclopenta[a]chrysene-3a-carboxylic acid was dissolved in 15 ml of Ethanol then 0.285 mg of arginine in 1 ml of Deionised water was added and charged in stirred solution. A clear solution was formed after stirring for 30 minutes. The reaction mixture was heated to 50-60° C. for 30 minutes and cooled to 30-40° C. The ethanol mixture was concentrated with a stream of nitrogen gas. A clear solid was obtained which was charged and dissolved in 10 ml of diethyl ether. The solvent was evaporated and the obtained solid is filtered & dried under vacuum for overnight. IR[cm$^{-1}$]: 3399, 2948, 2868, 1639, 1547, 1459, 1393, 1369, 1194, 1019, 880; H$^1$ NMR in CD3OD: 0.94-0.98 (m, 22H), 1.34-1.95 (m, 31H), 2.18-2.27 (m, 1H), 2.32-2.52 (m, 2H), 2.60-2.73 (m, 2H), 3.01-3.49 (m, 9H), 4.36-4.38 (m, 1H), 4.48 (s, 1H), 4.68 (s, 1H).

Example 23

Preparation of choline hydroxide salt of (1R,5bS,9S, 11aR)-9-((1R,3S)-3-carboxy-2,2-dimethylcyclobutanecarbonyloxy)-5b,8,8,11a-tetramethyl-1-(prop-1-en-2-yl)icosahydro-1H-cyclopenta[a]chrysene-3a-carboxylic acid

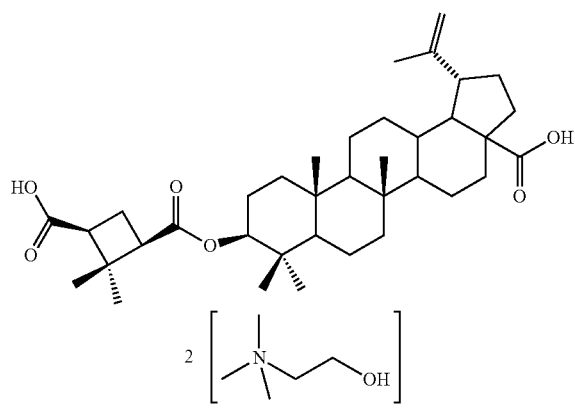

500 mg of (1R,5bS,9S,11aR)-9-((1R,3S)-3-carboxy-2,2-dimethylcyclobutanecarbonyloxy)-5b,8,8,11a-tetramethyl-1-(prop-1-en-2-yl)icosahydro-1H-cyclopenta[a]chrysene-3a-carboxylic acid was dissolved in 15 ml of Ethanol then 0.43 ml of liquid choline hydroxide in 1 ml of Deionised water was added and charged in stirred solution. Clear solution was formed after stirring for 30 minutes. The reaction mixture was heated to 50-60° C. for 30 minutes and cooled to 30-40° C. The ethanol mixture was concentrated with a stream of nitrogen gas. A clear solid was obtained which was charged and dissolved in 10 ml of diethyl ether. The solvent was evaporated and the obtained solid was filtered & dried under vacuum for overnight. IR[cm$^{-1}$]: 3264, 2946, 2866, 1722, 1646, 1562, 1478, 1390, 1368, 1276, 1189, 1089, 957, 870; H$^1$ NMR in CD3OD: 0.86-0.99 (m, 22H), 1.00-1.89 (m, 20H), 1.90-1.93 (m, 2H), 2.43-2.47 (m, 1H), 2.59-2.62 (m, 1H), 2.66-2.70 (m, 2H), 3.13-3.48 (m, 20H), 3.50-3.59 (m, 4H), 3.97-3.99 (m, 5H), 4.37-4.40 (m, 1H), 4.43 (s, 1H), 4.53 (s, 1H).

Example 24

Preparation of diethanolamine salt of (1R,5bS,9S, 11aR)-9-((1R,3S)-3-carboxy-2,2-dimethylcyclobutanecarbonyloxy)-5b,8,8,11a-tetramethyl-1-(prop-1-en-2-yl)icosahydro-1H-cyclopenta[a]chrysene-3a-carboxylic acid

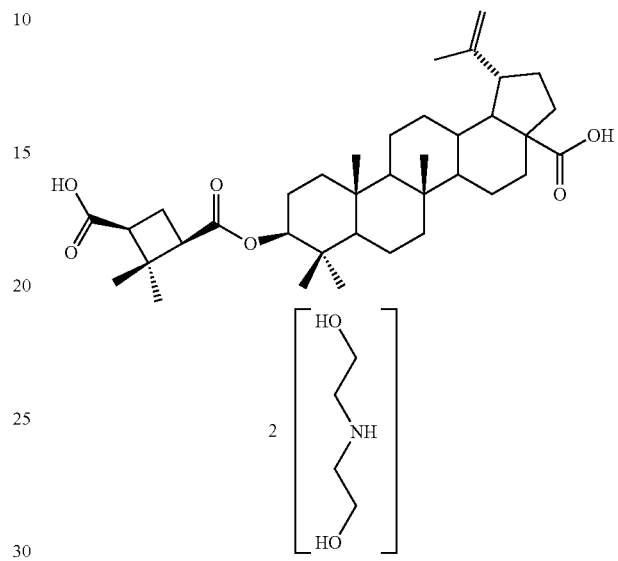

500 mg of (1R,5bS,9S,11aR)-9-((1R,3S)-3-carboxy-2,2-dimethylcyclobutanecarbonyloxy)-5b,8,8,11a-tetramethyl-1-(prop-1-en-2-yl)icosahydro-1H-cyclopenta[a]chrysene-3a-carboxylic acid was dissolved in 20 ml of methanol then 0.15 ml of Diethanolamine in 1 ml of Deionised water was added and charged in stirred solution. Clear solution was formed after stirring for 30 minutes. The reaction mixture was heated to 50-60° C. for 30 minutes and cooled to 30-40° C. The ethanol mixture was concentrated with a stream of nitrogen gas. A clear solid was obtained which was charged and dissolved in 10 ml of diethyl ether. The solvent was evaporated and the obtained solid was filtered & dried under vacuum for overnight. IR[cm$^{-1}$]: 3304, 2944, 2866, 1724, 1550, 1459, 1373, 1139, 1071, 965, 875; H$^1$ NMR in CD3OD: 086-1.30 (m, 22H), 1.33-1.71 (22H), 1.85-191 (m, 4H), 2.19-2.23 (m, 1H), 2.37-2.44 (m, 2H), 2.48-2.69 (m, 2H), 2.84-3.03 (m, 10H), 3.62-3.80 (m, 12H), 4.38 (m, 1H), 4.53 (s, 1H), 4.66 (s, 1H).

Example 25

Preparation of bis-N-methyl glucamine salt of (1R, 5bS,9S,11aR)-9-((1R,3S)-3-carboxy-2,2-dimethylcyclobutanecarbonyloxy)-5b,8,8,11a-tetramethyl-1-(prop-1-en-2-yl)icosahydro-1H-cyclopenta[a]chrysene-3a-carboxylic acid

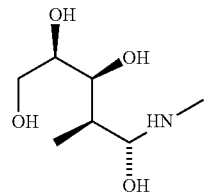

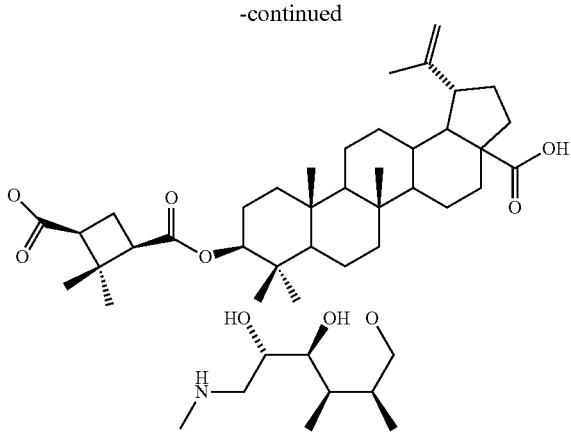

500 mg of (1R,5bS,9S,11aR)-9-((1R,3S)-3-carboxy-2,2-dimethylcyclobutanecarbonyloxy)-5b,8,8,11a-tetramethyl-1-(prop-1-en-2-yl)icosahydro-1H-cyclopenta[a]chrysene-3a-carboxylic acid was dissolved in 30 ml of methanol then 320 mg of solid N-methyl glucamine in 1 ml of Deionised water was added and charged in stirred solution. A clear solution was formed after stirring for 30 minutes. The reaction mixture was heated to 50-60° C. for 30 minutes and cooled to 30-40° C. The methanol mixture was concentrated with a stream of nitrogen gas. A clear solid was obtained which was charged and dissolved in 10 ml of diethyl ether. The solvent was evaporated and the obtained solid was filtered & dried under vacuum for overnight.

Example 26

Preparation of dipotassium salt of (1R,5bS,9S,11aR)-9-((1R,3S)-3-carboxy-2,2-dimethylcyclobutanecarbonyloxy)-5b,8,8,11a-tetramethyl-1-(prop-1-en-2-yl)icosahydro-1H-cyclopenta[a]chrysene-3a-carboxylic acid

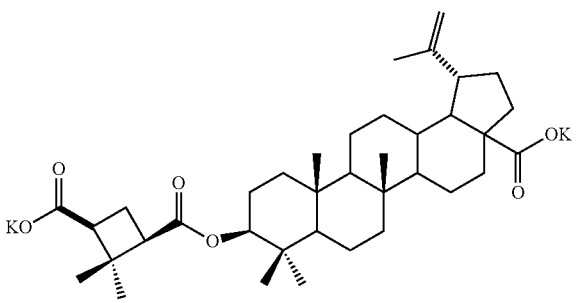

400 mg of (1R,5bS,9S,11aR)-9-((1R,3S)-3-carboxy-2,2-dimethylcyclobutanecarbonyloxy)-5b,8,8,11a-tetramethyl-1-(prop-1-en-2-yl)icosahydro-1H-cyclopenta[a]chrysene-3a-carboxylic acid was dissolved in 12 ml of methanol then 90 mg of KOH in 1 ml of Deionised water was added and charged in stirred solution. Clear solution was formed after stirring for 30 minutes. The reaction mixture was heated to 50-60° C. for 30 minutes and cooled to 30-40° C. The methanol mixture was concentrated with a stream of nitrogen gas. A clear solid was obtained which was charged and dissolved in 10 ml of diethyl ether. The solvent was evaporated and the obtained solid was filtered & dried under vacuum for overnight. IR [cm$^{-1}$]: 3412, 2948, 2868, 1712, 1554, 1455, 1390, 1371, 1197, 881; $^1$H NMR (300 MHZ, CDCl$_3$): δ 4.74 (s, 1H), 4.61 (s, 1H), 4.47-4.43 (m, 1H), 3.03-2.97 (m, 1H), 2.87-2.74 (m, 2H), 2.63-2.51 (m, 1H), 2.31-2.24 (m, 2H), 2.19-1.90 (m, 3H), 1.69 (s, 3H), 1.78-1.68 (m, 5H), 1.52-1.41 (m, 12H), 1.29-1.02 (m, 9H), 0.97 (s, 3H), 0.93 (s, 3H), 0.85 (s, 9H);

Example 27

Preparation of disodium salt of (1R,5bS,9S,11aR)-9-((1R,3S)-3-carboxy-2,2-dimethylcyclobutanecarbonyloxy)-5b,8,8,11a-tetramethyl-1-(prop-1-en-2-yl)icosahydro-1H-cyclopenta[a]chrysene-3a-carboxylic acid

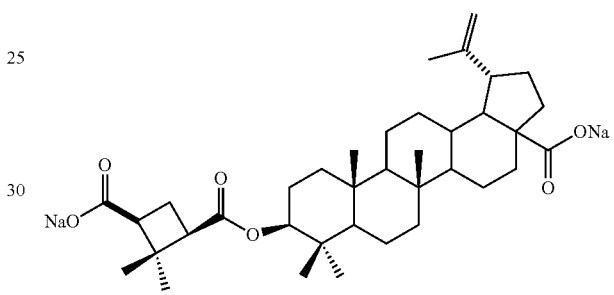

400 mg of (1R,5bS,9S,11aR)-9-((1R,3S)-3-carboxy-2,2-dimethylcyclobutanecarbonyloxy)-5b,8,8,11a-tetramethyl-1-(prop-1-en-2-yl)icosahydro-1H-cyclopenta[a]chrysene-3a-carboxylic acid was dissolved in 10 ml of methanol then 60 mg of NaOH in 1 ml of Deionised water was added and charged in stirred solution. Clear solution was formed after stirring for 30 minutes. The reaction mixture was heated to 50-60° C. for 30 minutes and cooled to 30-40° C. The methanol mixture was concentrated with a stream of nitrogen gas. A clear solid was obtained which was charged and dissolved in 10 ml of diethyl ether. The solvent was evaporated and the obtained solid is filtered & dried under vacuum for overnight. $^1$H NMR (300 MHZ, CDCl$_3$): δ 4.74 (s, 1H), 4.61 (s, 1H), 4.47-4.43 (m, 1H), 3.03-2.97 (m, 1H), 2.87-2.74 (m, 2H), 2.63-2.51 (m, 1H), 2.31-2.24 (m, 2H), 2.19-1.90 (m, 3H), 1.69 (s, 3H), 1.78-1.68 (m, 5H), 1.52-1.41 (m, 12H), 1.29-1.02 (m, 9H), 0.97 (s, 3H), 0.93 (s, 3H), 0.85 (s, 9H).

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described above.

All publications and patent applications cited in this application are herein incorporated by reference to the same extent as if each individual publication or patent application was specifically and individually indicated to be incorporated herein by reference.

The invention claimed is:
1. A salt of a compound of formula (I):

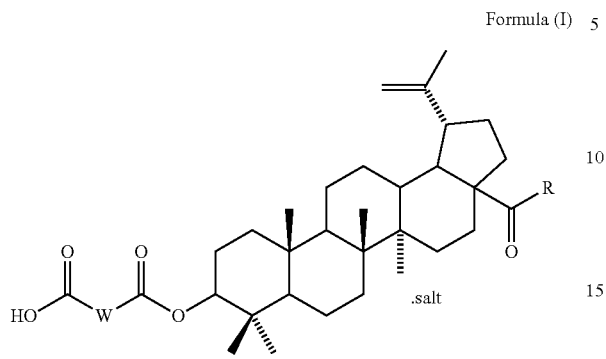

Formula (I)

Wherein,
R is

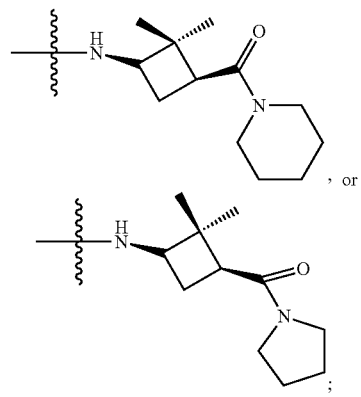

W is

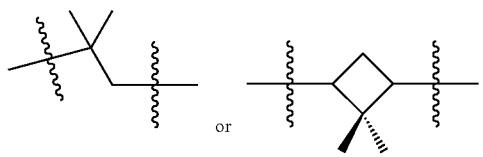

Salt is an arginine, amino guanidine, choline, dicyclohexylamine, diethanolamine, dimethyl piperazine, lithium, lysine, magnesium, N-methyl glucamine, N-octyl glucamine, piperazine, phenyl glycine methyl ester, phenyl glycinol, potassium, sodium, Trizma base primary standard buffer, or calcium, stereoisomers, enantiomers, diastereomers, racemates, or mixtures thereof.

2. A salt of a compound selected from the group consisting of

Arginine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid, Amino guanidine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid, Calcium salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid, Choline salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid, Dicyclohexylamine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid, Diethanolamine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid, 2,6-dimethyl piperazine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid, Lithium salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid, Lysine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid, Magnesium salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid, N-methyl Glucamine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid, N-octyl Glucamine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid, piperazine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid, Phenyl glycine methyl ester salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid, Phenyl glycinol salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid, Potassium salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid, Sodium salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid, Tris(hydroxymethyl)amino methane salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid, Sodium salt of 4-((1R,3aS,5aS,7aR,9S,11aR,11bS,13aR)-3a-((1S,3S)-2,2-dimethyl-3-(pyrrolidine-1-carbonyl)cyclobutylcarbamoyl)-5a,8,8,11a,13a-pentamethyl-1-(prop-1-en-2-yl)icosahydro-1H-cyclopenta[a]chrysen-9-yloxy)-2,2-dimethyl-4-oxobutanoic acid, Potassium salt of 4-((1R,3aS,5aS,7aR,9S,11aR,11bS,13aR)-3a-((1S,3S)-2,2-dimethyl-3-(pyrrolidine-1-carbonyl)cyclobutylcarbamoyl)-5a,8,8,11a,13a-pentamethyl-1-(prop-1-en-2-yl)icosahydro-1H-cyclopenta[a]chrysen-9-yloxy)-2,2-dimethyl-4-oxobutanoic acid, N-methyl Glucamine salt of 4-((1R,3aS,5aS,7aR,9S,11aR,11bS,13aR)-3a-((1S,3S)-2,2-dimethyl-3-(pyrrolidine-1-carbonyl)cyclobutylcarbamoyl)-5a,8,8,11a,13a-pentamethyl-1-(prop-1-en-2-yl)icosahydro-1H-cyclopenta[a]chrysen-9-yloxy)-2,2-dimethyl-4-oxobutanoic acid, Arginine salt of (1R,5bS,9S,11aR)-9-((1R,3S)-3-carboxy-2,2-dimethylcyclobutanecarbonyloxy)-5b,8,8,11a-tetramethyl-1-(prop-1-en-2-yl)icosahydro-1H-cyclopenta[a]chrysene-3a-carboxylic acid, Choline hydroxide salt of (1R,5bS,9S,11aR)-9-((1R,3S)-3-carboxy-2,2-dimethylcyclobutanecarbonyloxy)-5b,8,8,11a-tetramethyl-1-(prop-1-en-2-yl)icosahydro-1H-cyclopenta[a]chrysene-3a-carboxylic acid, Diethanolamine salt of (1R,5bS,9S,11aR)-9-((1R,3S)-3-carboxy-2,2-dimethylcyclobutanecarbonyloxy)-5b,8,8,11a-tetramethyl-1-(prop-1-en-2-yl)icosahydro-1H-cyclopenta[a]chrysene-3a-carboxylic acid, Bis-N-methyl glucamine salt of (1R,5bS,9S,11aR)-9-((1R,3S)-3-carboxy-2,2-dimethylcyclobutanecarbonyloxy)-5b,8,8,11a-tetramethyl-1-(prop-1-en-2-yl)icosahydro-1H-cyclopenta[a]chrysene-3a-carboxylic acid, Dipotassium salt of (1R,5bS,9S,11aR)-9-((1R,3S)-3-carboxy-2,2-dimethylcyclobutanecarbonyloxy)-5b,8,8,11a-tetramethyl-1-(prop-1-en-2-yl)icosahydro-1H-cyclopenta[a]chrysene-3a-carboxylic acid, and Disodium salt of (1R,5bS,9S,11aR)-9-((1R,3S)-3-carboxy-2,2-dimethylcyclobutanecarbonyloxy)-5b,8,8,11a-tetramethyl-1-(prop-1-en-2-yl)icosahydro-1H-cyclopenta[a]chrysene-3a-carboxylic acid.

Figure 8:
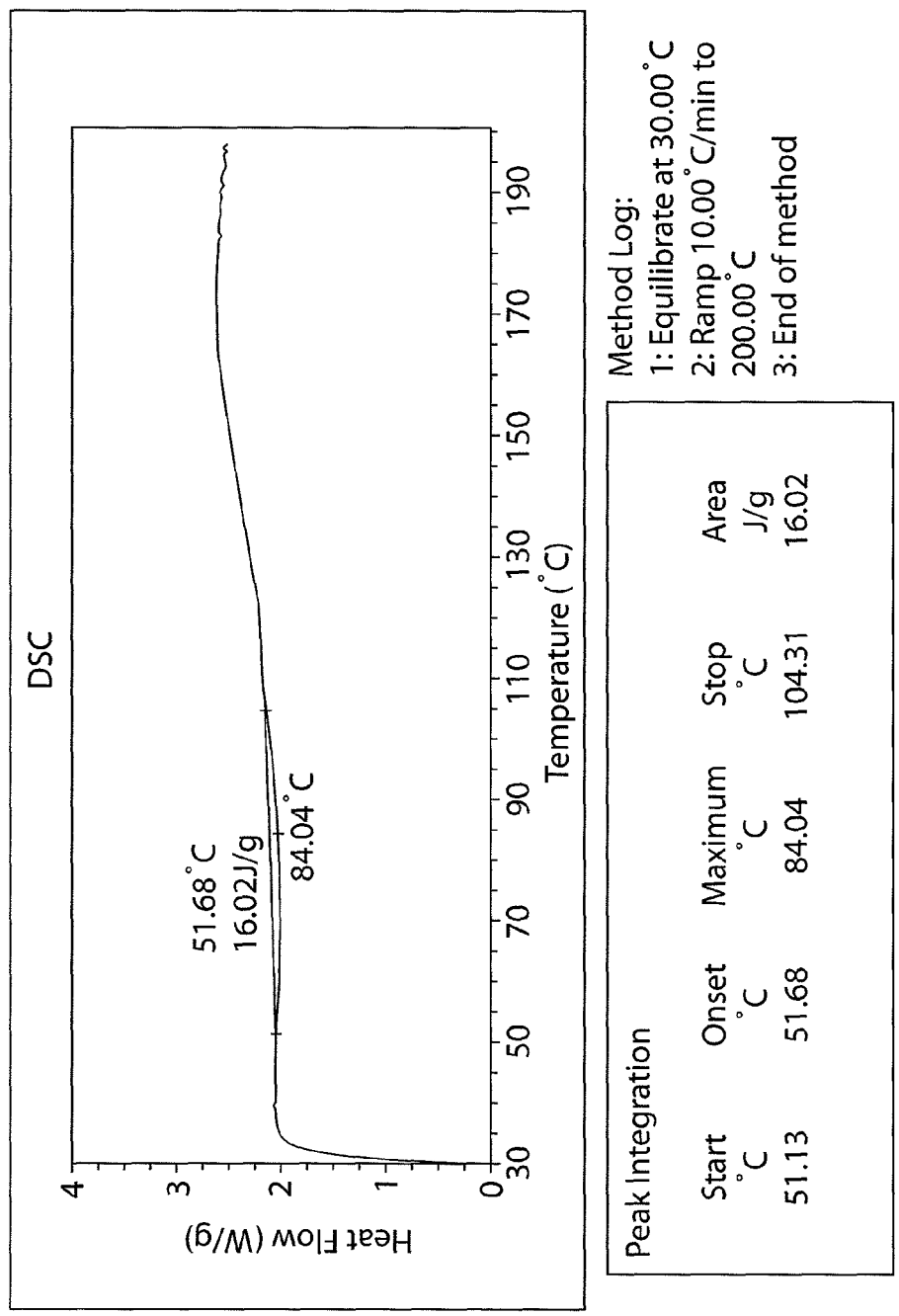
FIG. 8: DSC of Arginine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid.

3. A salt of a compound according to claim 1, wherein the Arginine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid is characterized by an x-ray powder diffraction pattern substantially in accordance with that shown in FIG. 1 and a differential scanning calorimetry thermogram substantially in accordance with that shown in FIG. 8.

Figure 2A:
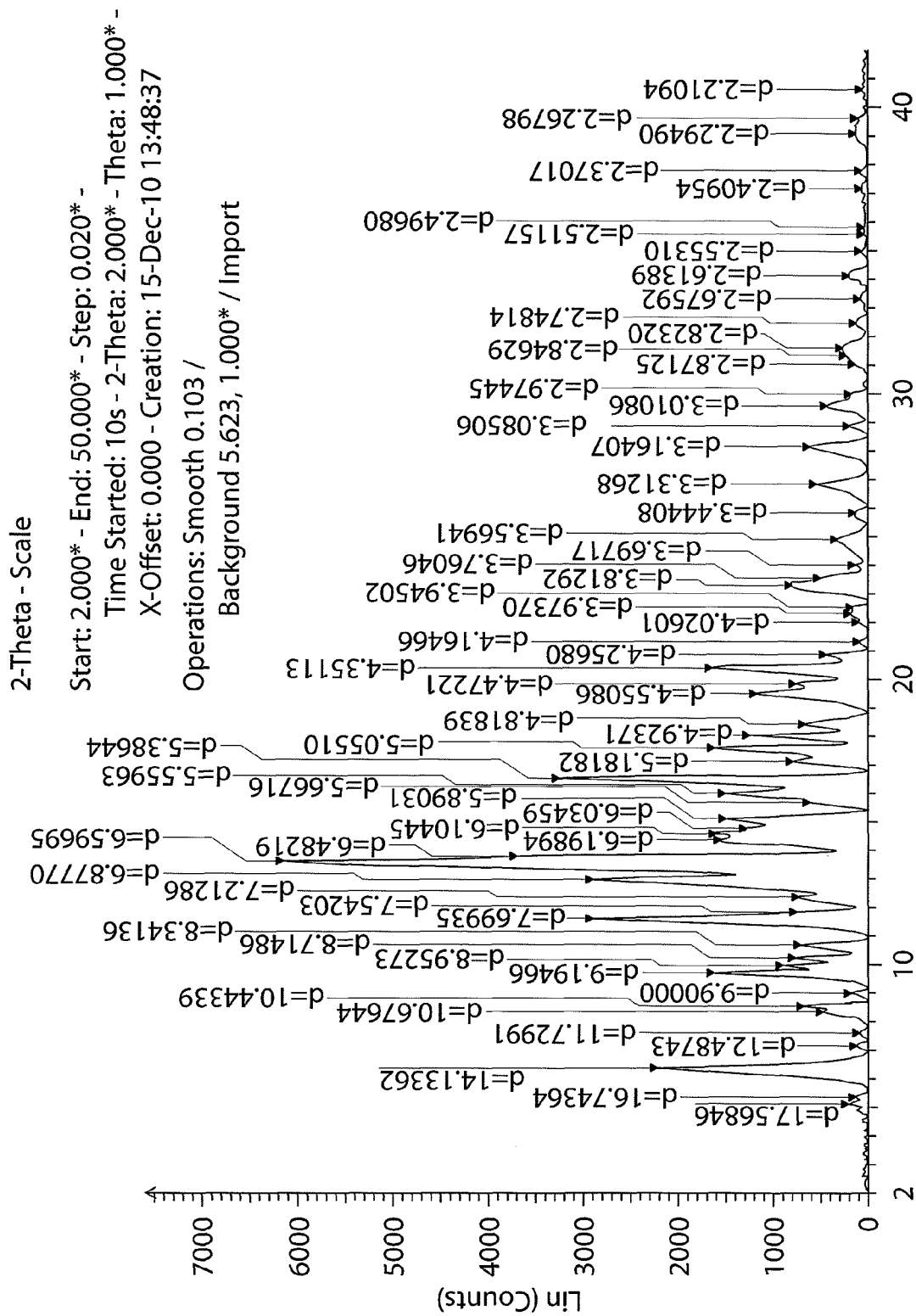
(FIG. 2A) XRPD of Amino guanidine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid.
Figure 9:
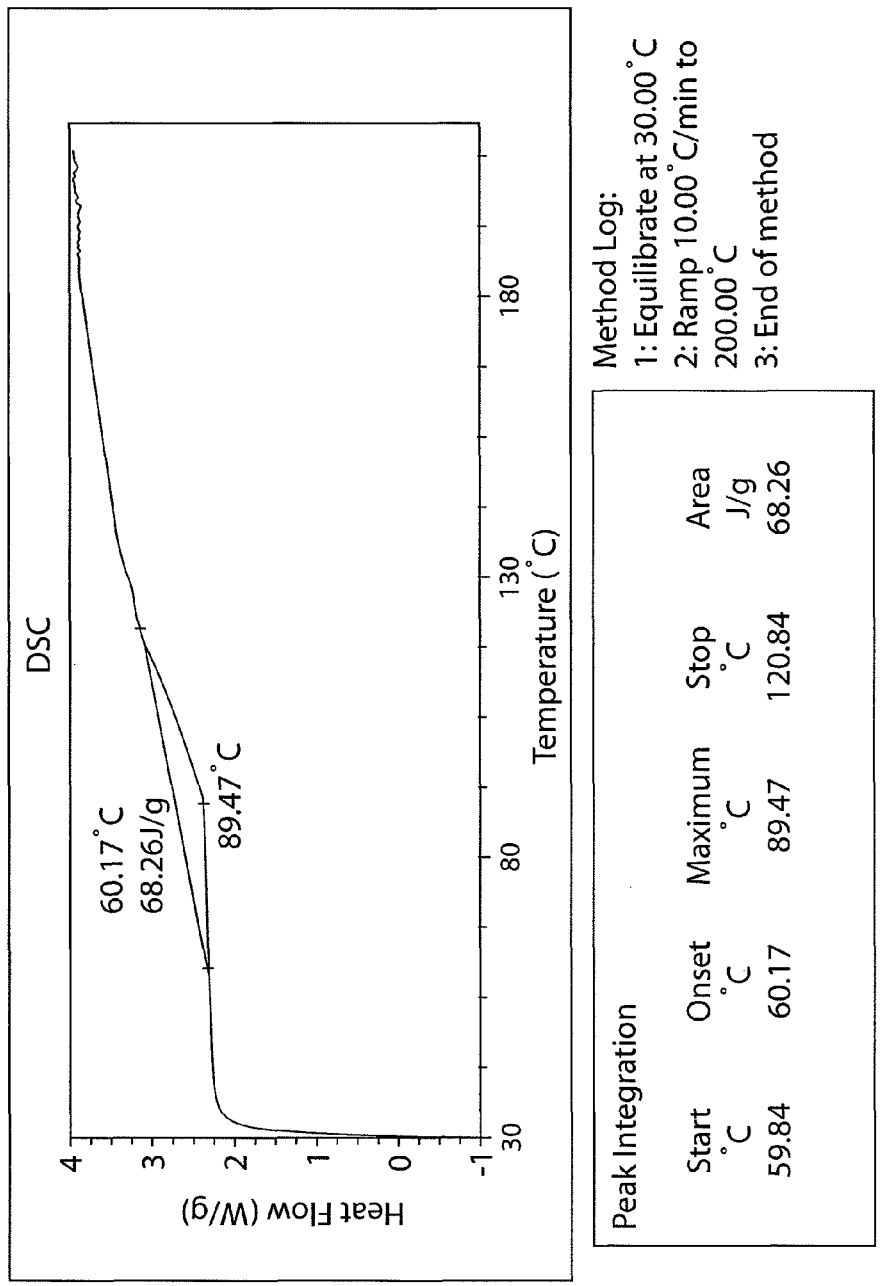
FIG. 9: DSC of Amino guanidine salt of 44(1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid.

4. A salt of a compound according to claim 1, wherein the Amino guanidine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid is characterized by an x-ray powder diffraction pattern substantially in accordance with that shown in FIG. 2 and a differential scanning calorimetry thermogram substantially in accordance with that shown in FIG. 9.

Figure 3A:
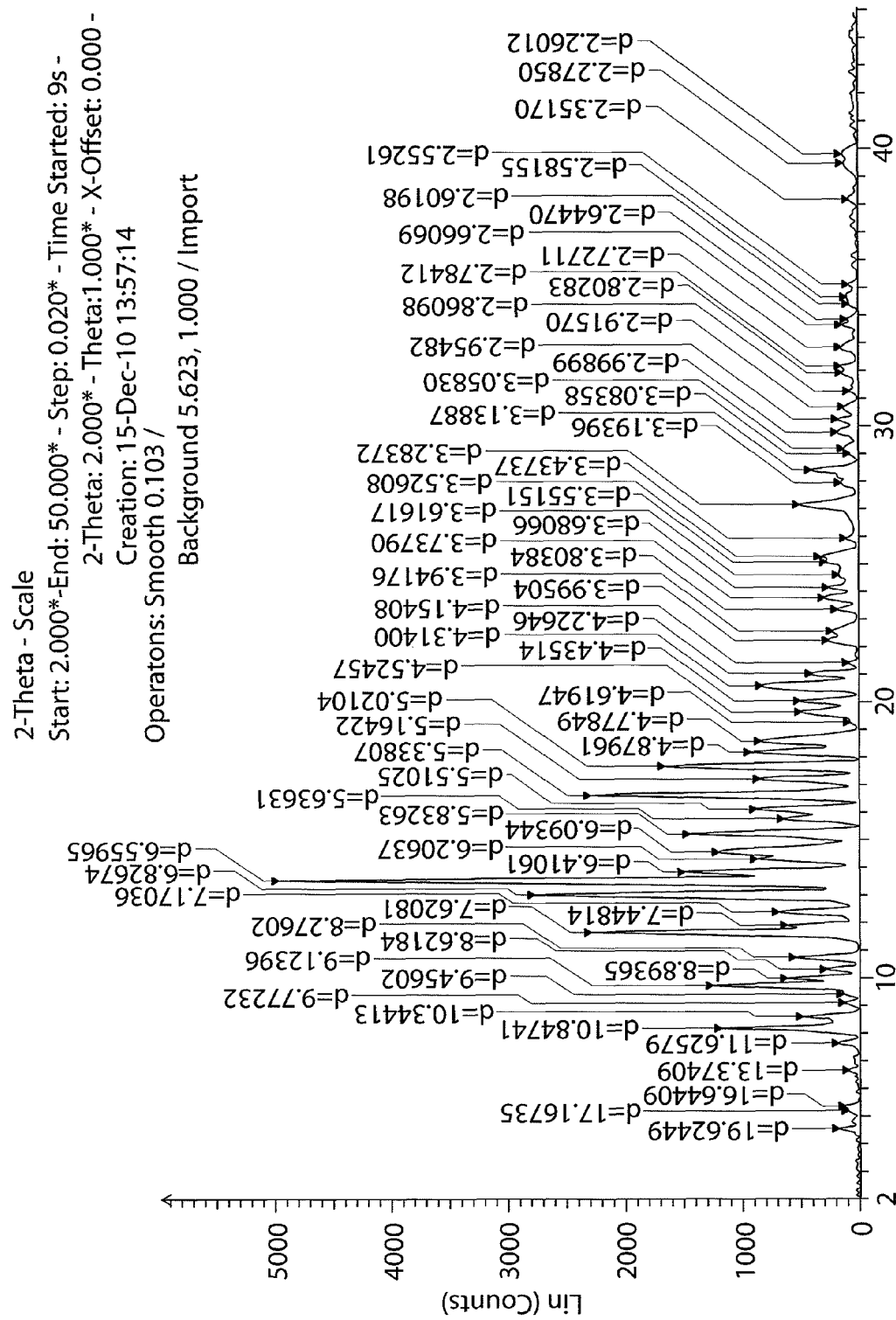
(FIG. 3A) XRPD of Calcium salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid.
Figure 10:
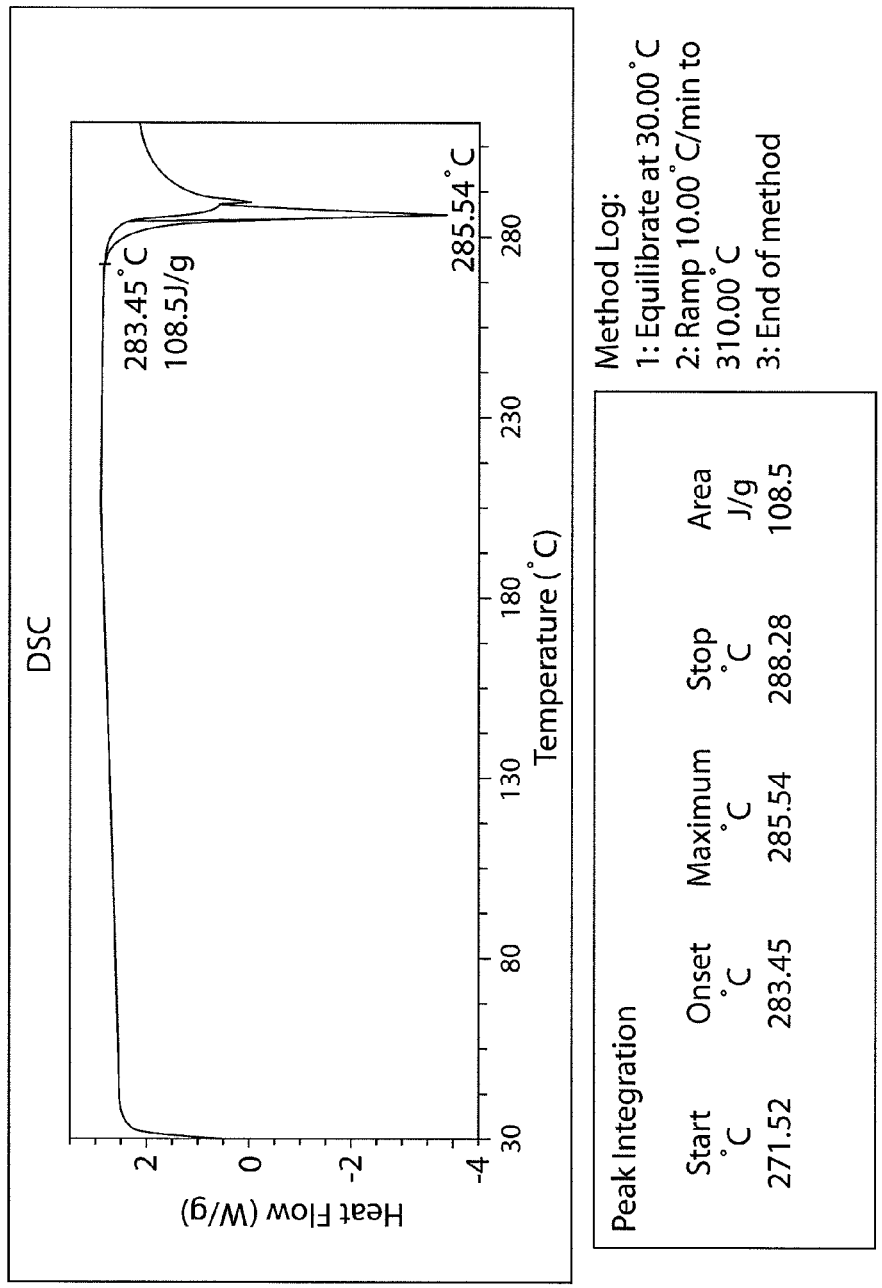
FIG. 10: DSC of Calcium salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid.

5. A salt of a compound according to claim 1, wherein the Calcium salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid is characterized by an x-ray powder diffraction pattern substantially in accordance with that shown in FIG. 3 and a differential scanning calorimetry thermogram substantially in accordance with that shown in FIG. 10.

Figure 4A:
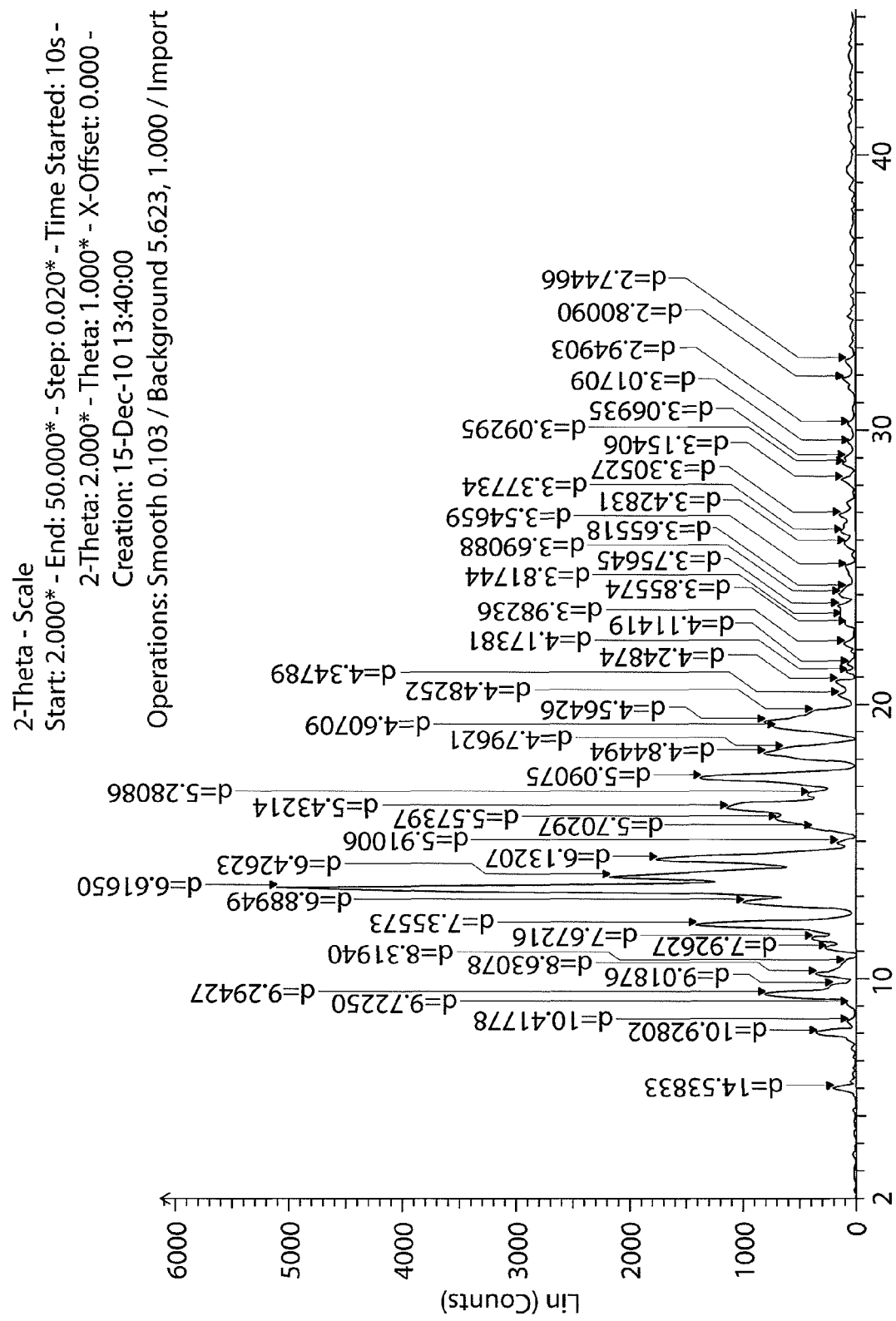
(FIG. 4A) XRPD of Choline salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid.
Figure 11:
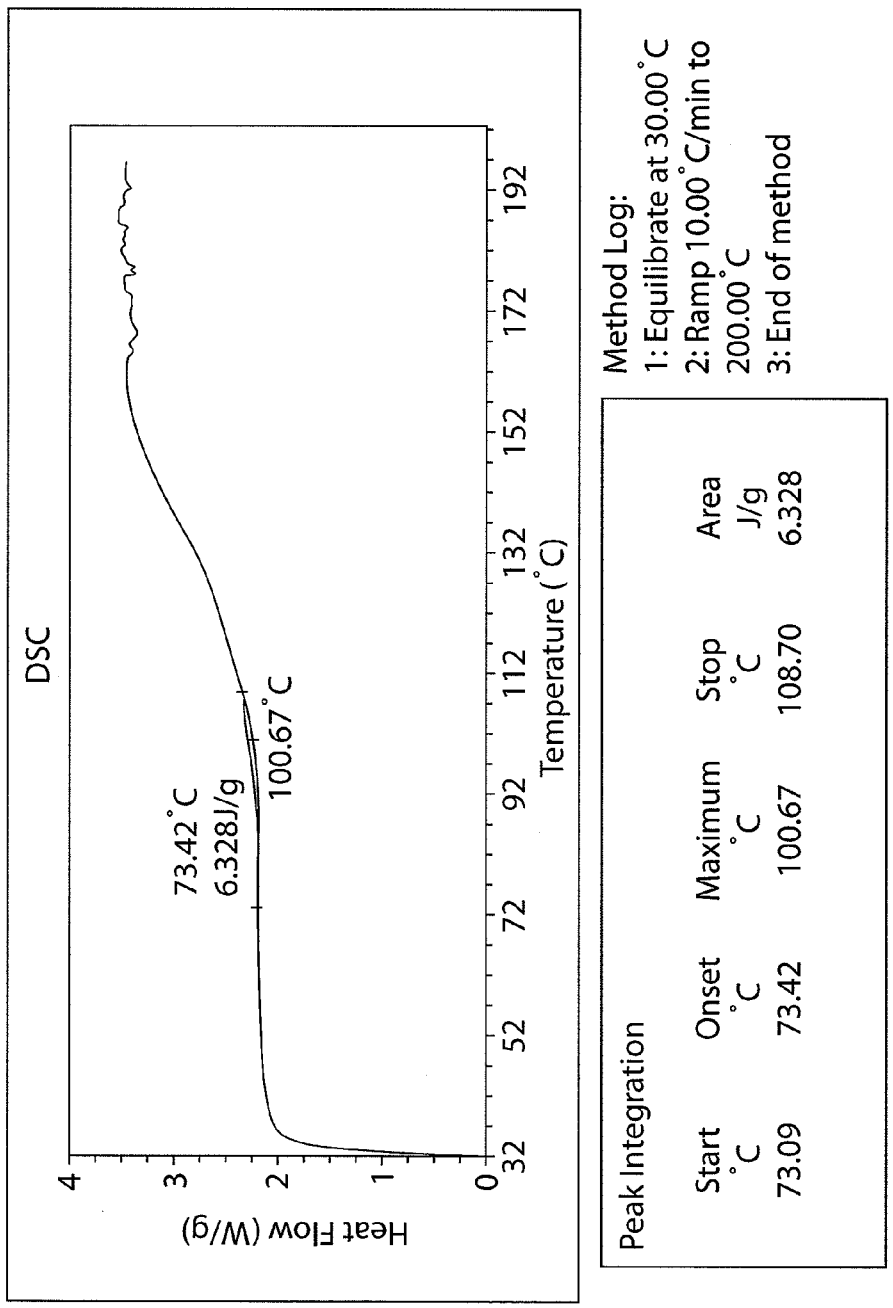
FIG. 11: DSC of choline salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid.

6. A salt of a compound according to claim 1, wherein the Choline salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)-icosahydro-1H-cyclopenta[a]chrysen-9-yloxy)-2,2-dimethyl-4-oxobutanoic acid is characterized by an x-ray powder diffraction pattern substantially in accordance with that shown in FIG. 4 and a differential scanning calorimetry thermogram substantially in accordance with that shown in FIG. 11.

Figure 12:
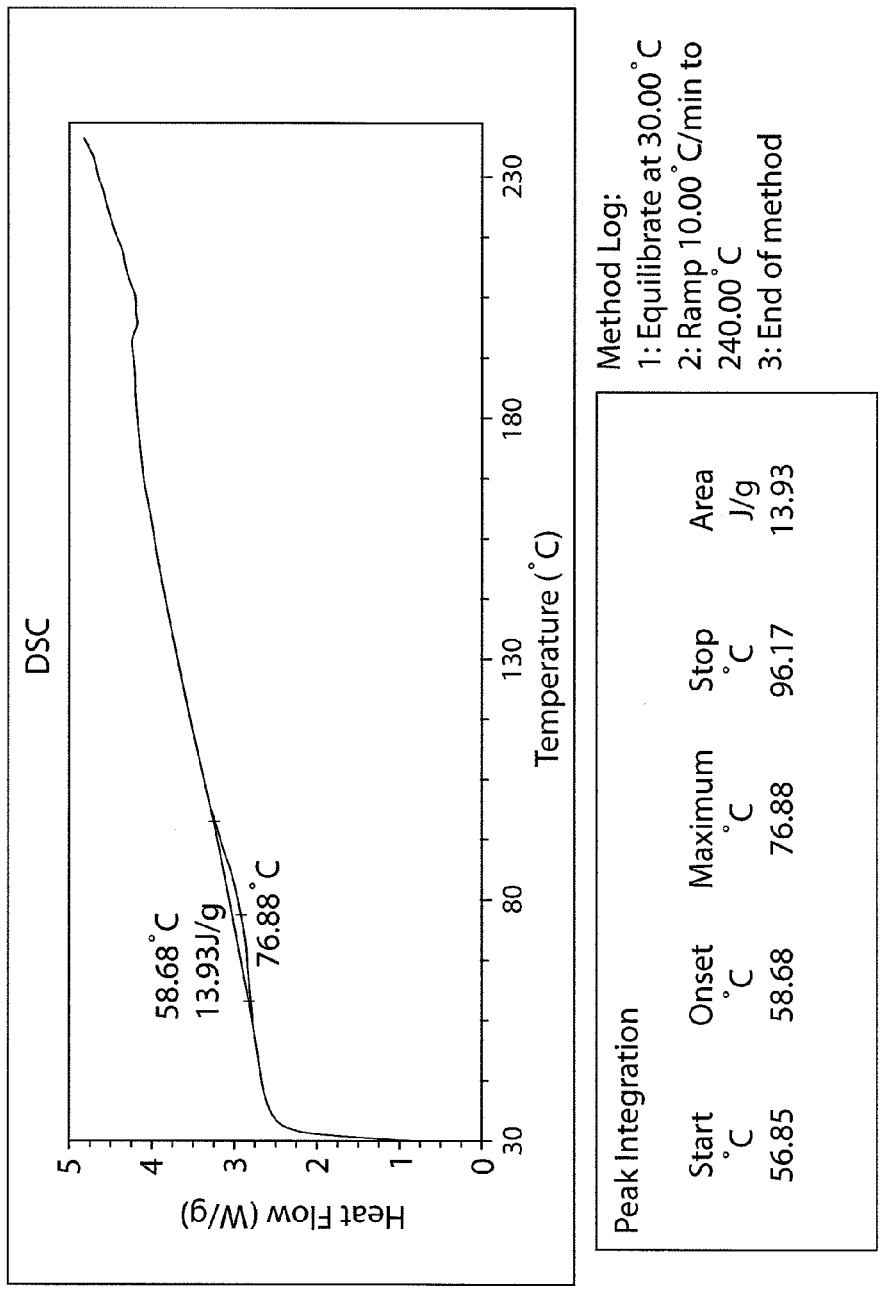
FIG. 12: DSC of Dicyclohexylamine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid.

7. A salt of a compound according to claim 1, wherein the Dicyclohexylamine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid is characterized by a differential scanning calorimetry thermogram substantially in accordance with that shown in FIG. 12.

Figure 13:
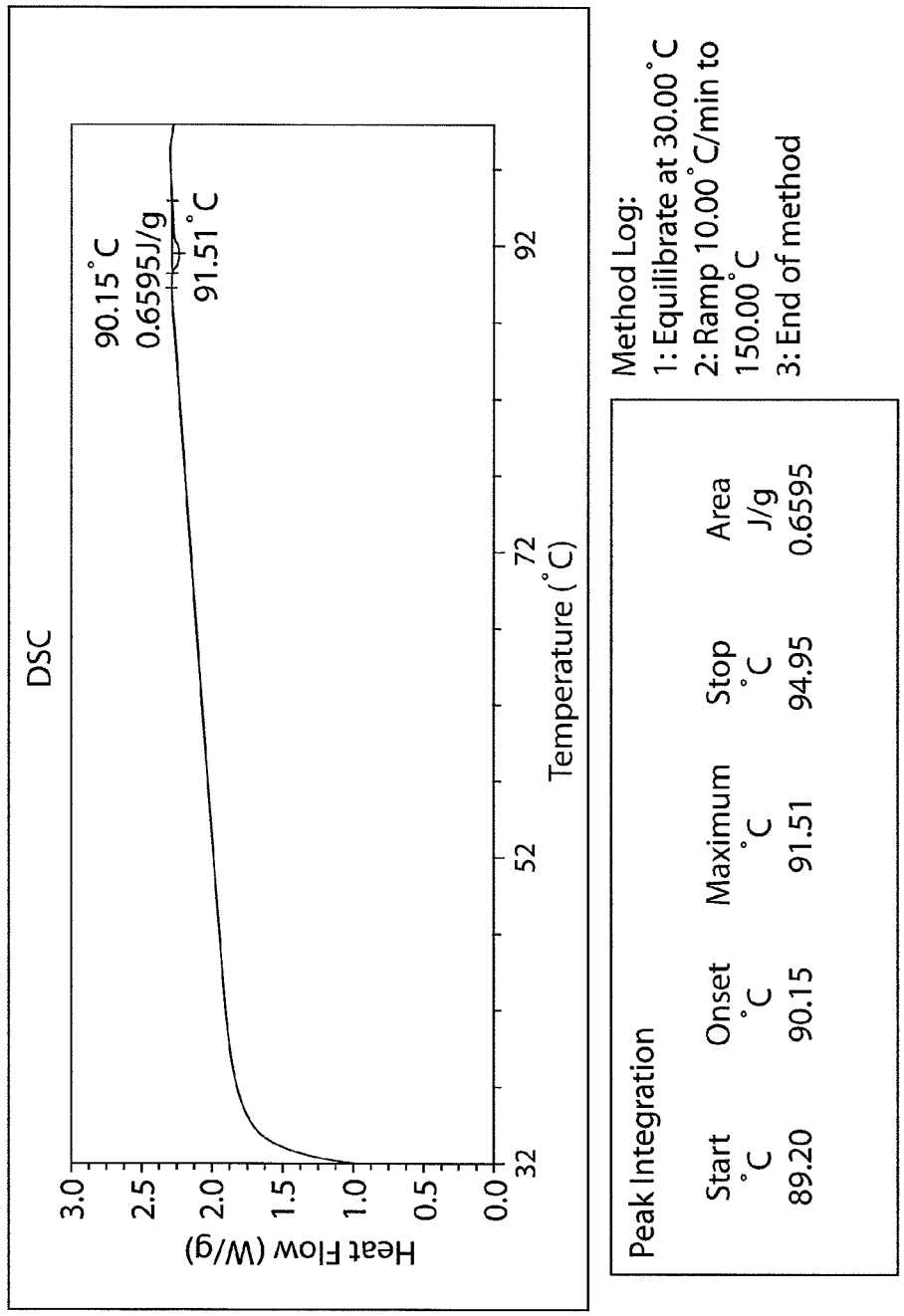
FIG. 13: DSC of Diethanolamine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid.

8. A salt of a compound according to claim 1, wherein the Diethanolamine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid is characterized by a differential scanning calorimetry thermogram substantially in accordance with that shown in FIG. 13.

Figure 14:
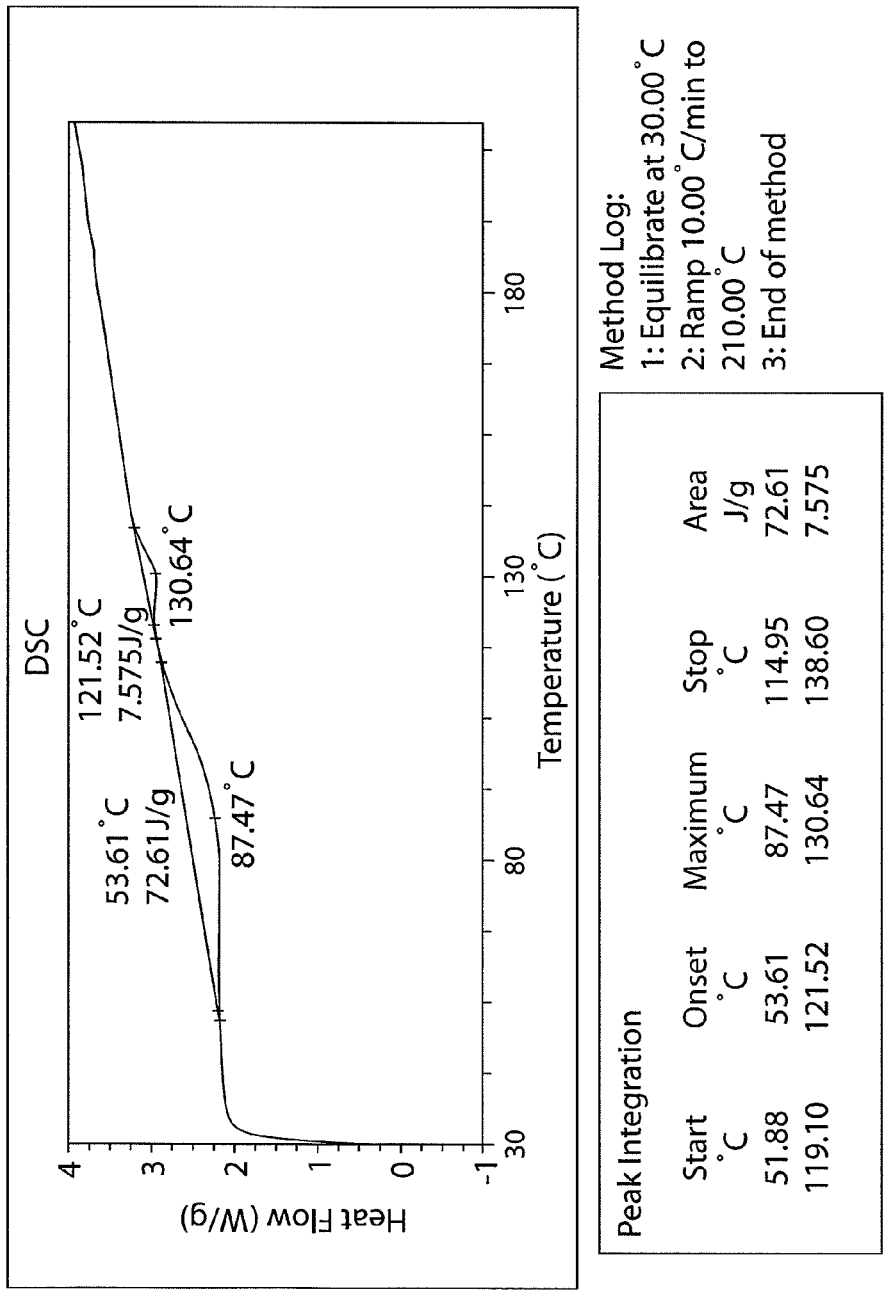
FIG. 14: DSC of 2,6-Dimethyl piperazine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid.

9. A salt of a compound according to claim 1, wherein the 2,6-dimethyl piperazine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid is characterized by a differential scanning calorimetry thermogram substantially in accordance with that shown in FIG. 14.

Figure 15:
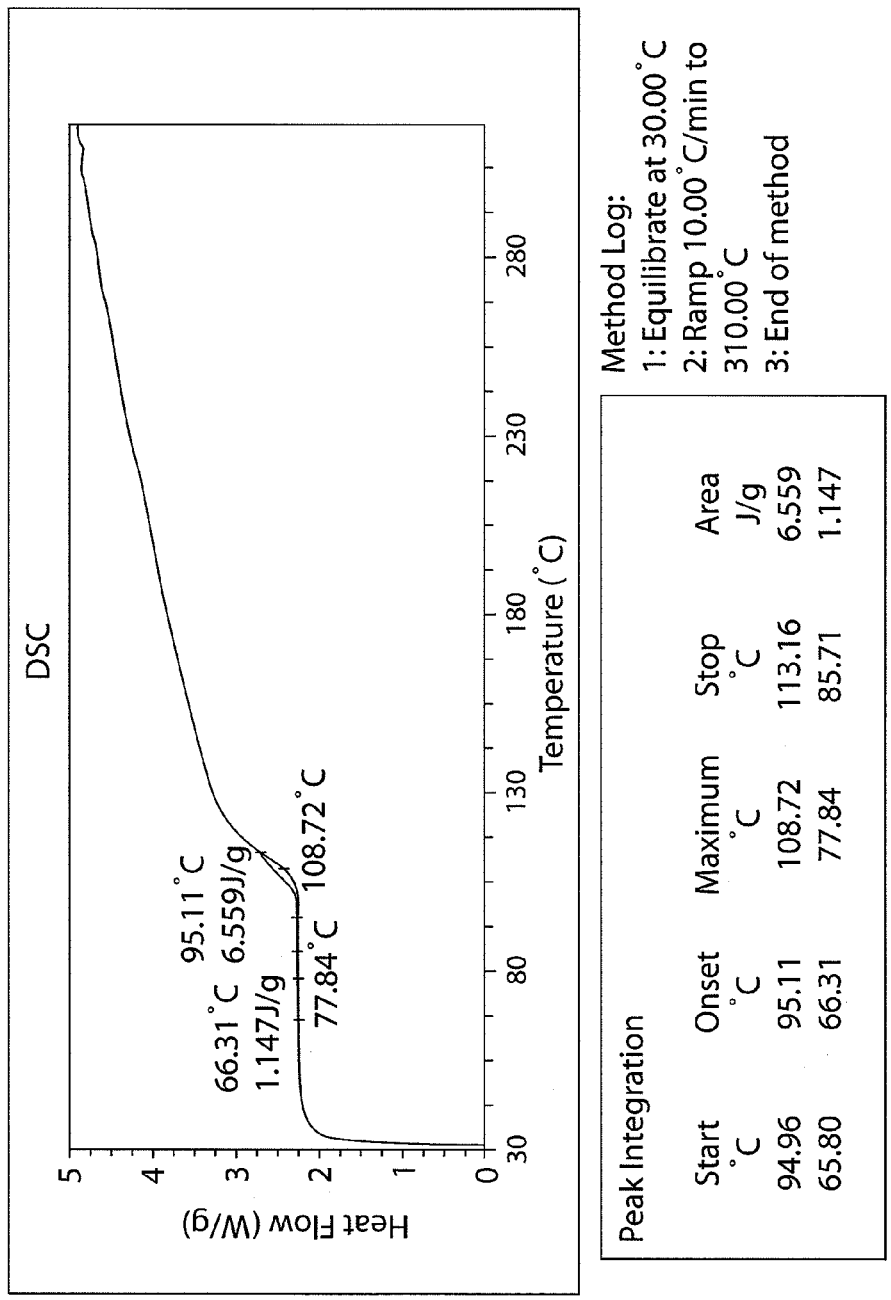
FIG. 15: DSC of Lithium salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid.

10. A salt of a compound according to claim 1, wherein the Lithium salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid is characterized by a differential scanning calorimetry thermogram substantially in accordance with that shown in FIG. 15.

Figure 16:
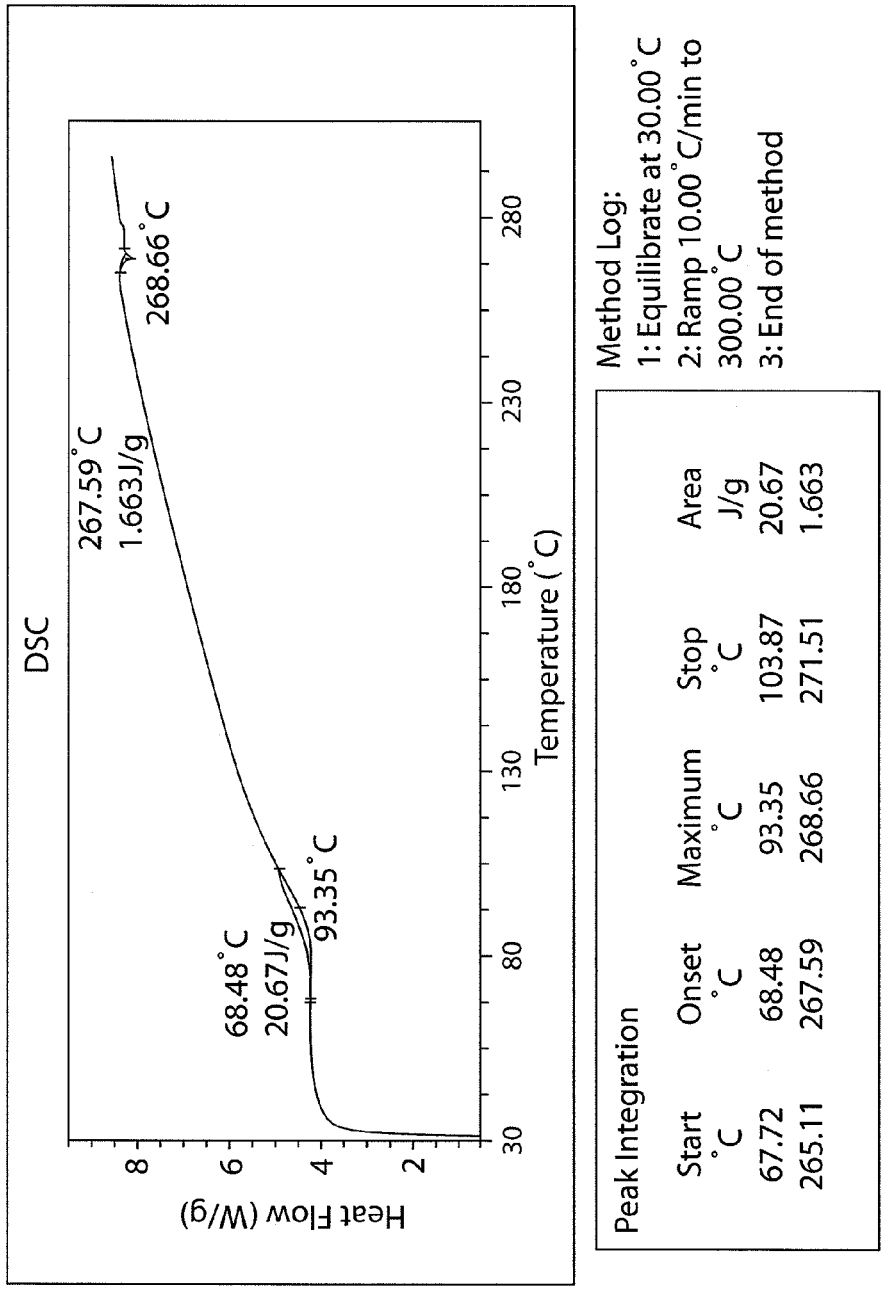
FIG. 16: DSC of Magnesium salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid.

11. A salt of a compound according to claim 1, wherein the Magnesium salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid is characterized by a differential scanning calorimetry thermogram substantially in accordance with that shown in FIG. 16.

Figure 5A:
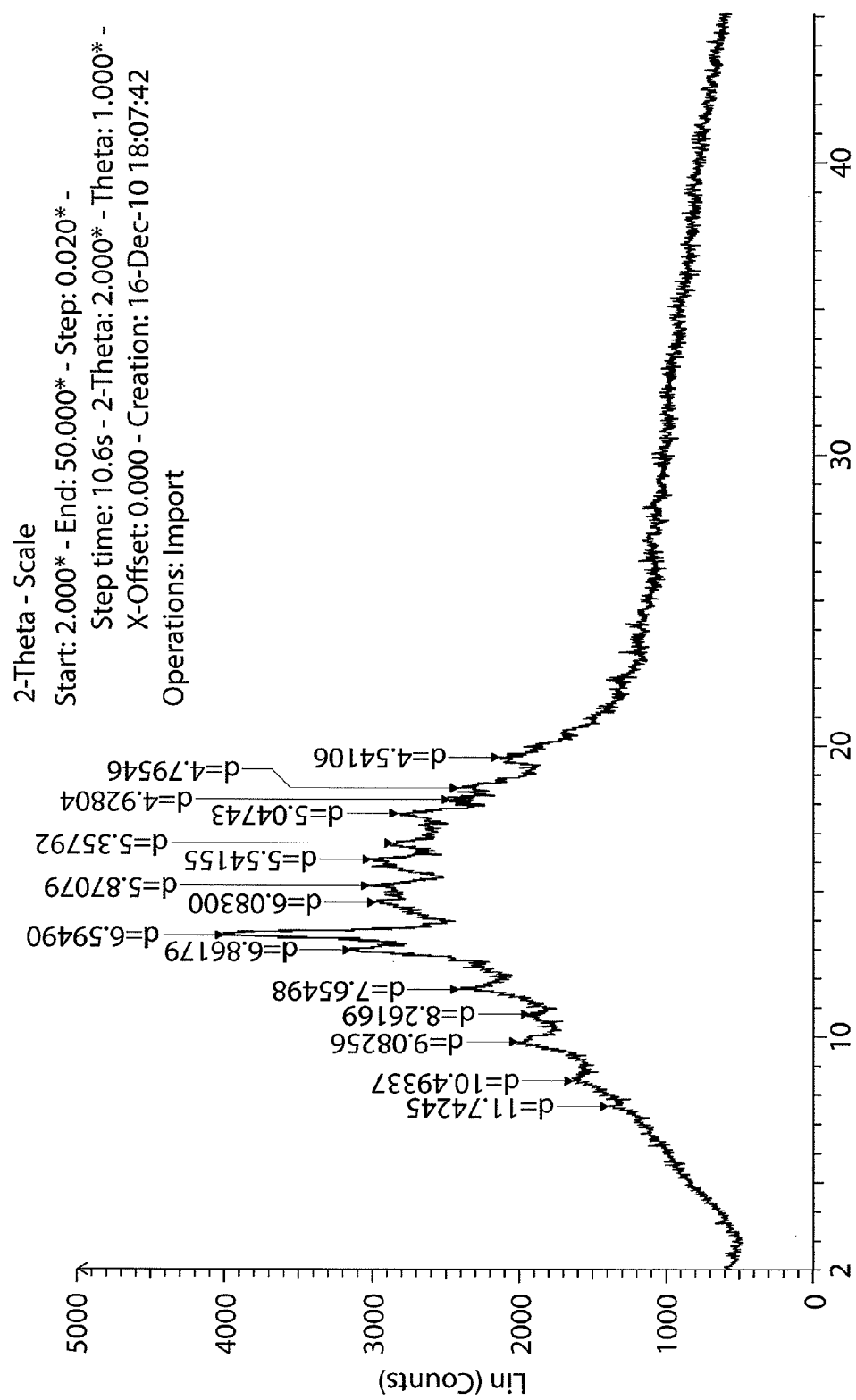
(FIG. 5A) XRPD of N-methyl glucamine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid.
Figure 17:
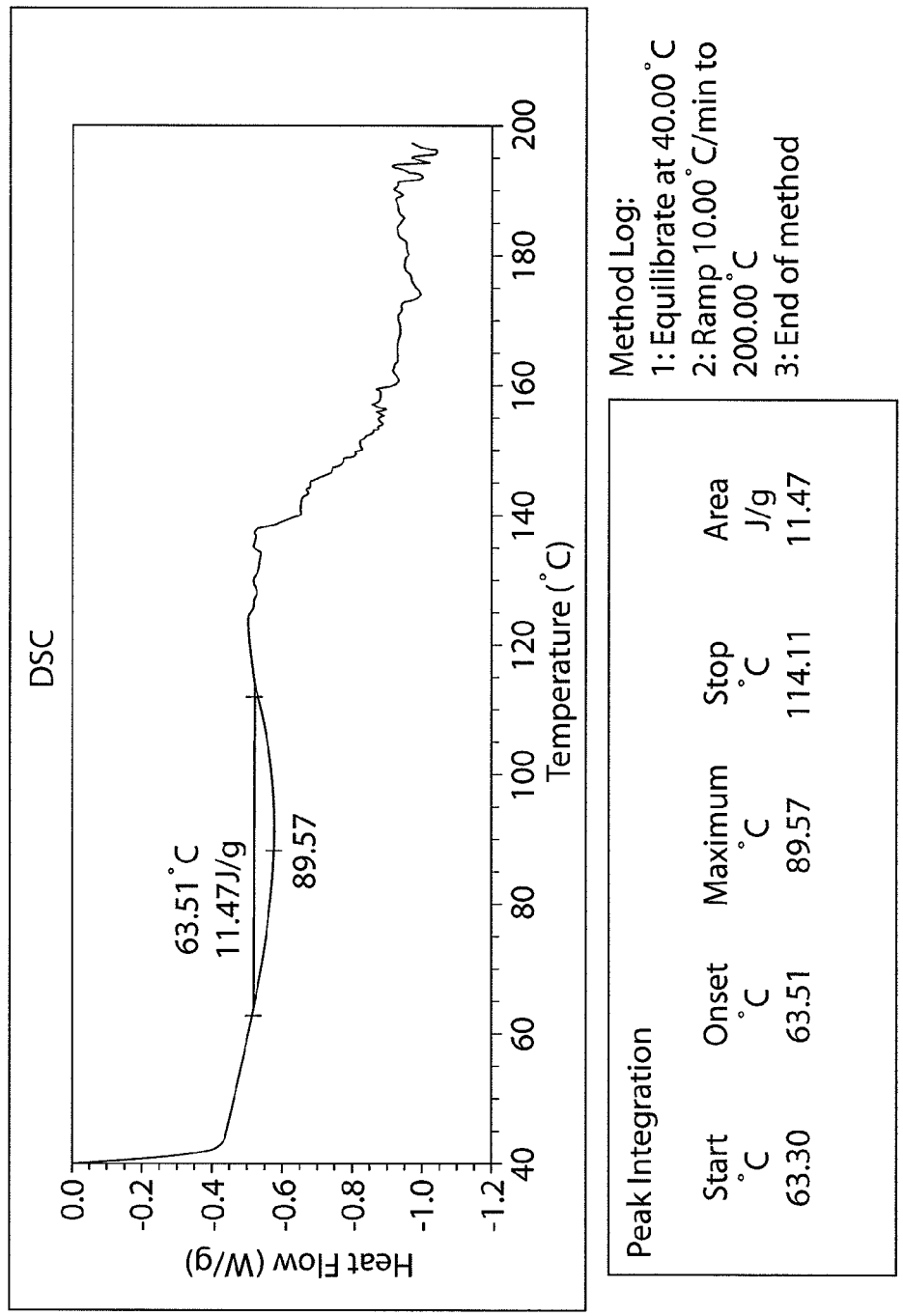
FIG. 17: DSC of N-methyl glucamine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid.

12. A salt of a compound according to claim 1, wherein the N-methyl Glucamine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid is characterized by an x-ray powder diffraction pattern substantially in accordance with that shown in FIG. 5 and a differential scanning calorimetry thermogram substantially in accordance with that shown in FIG. 17.

Figure 18:
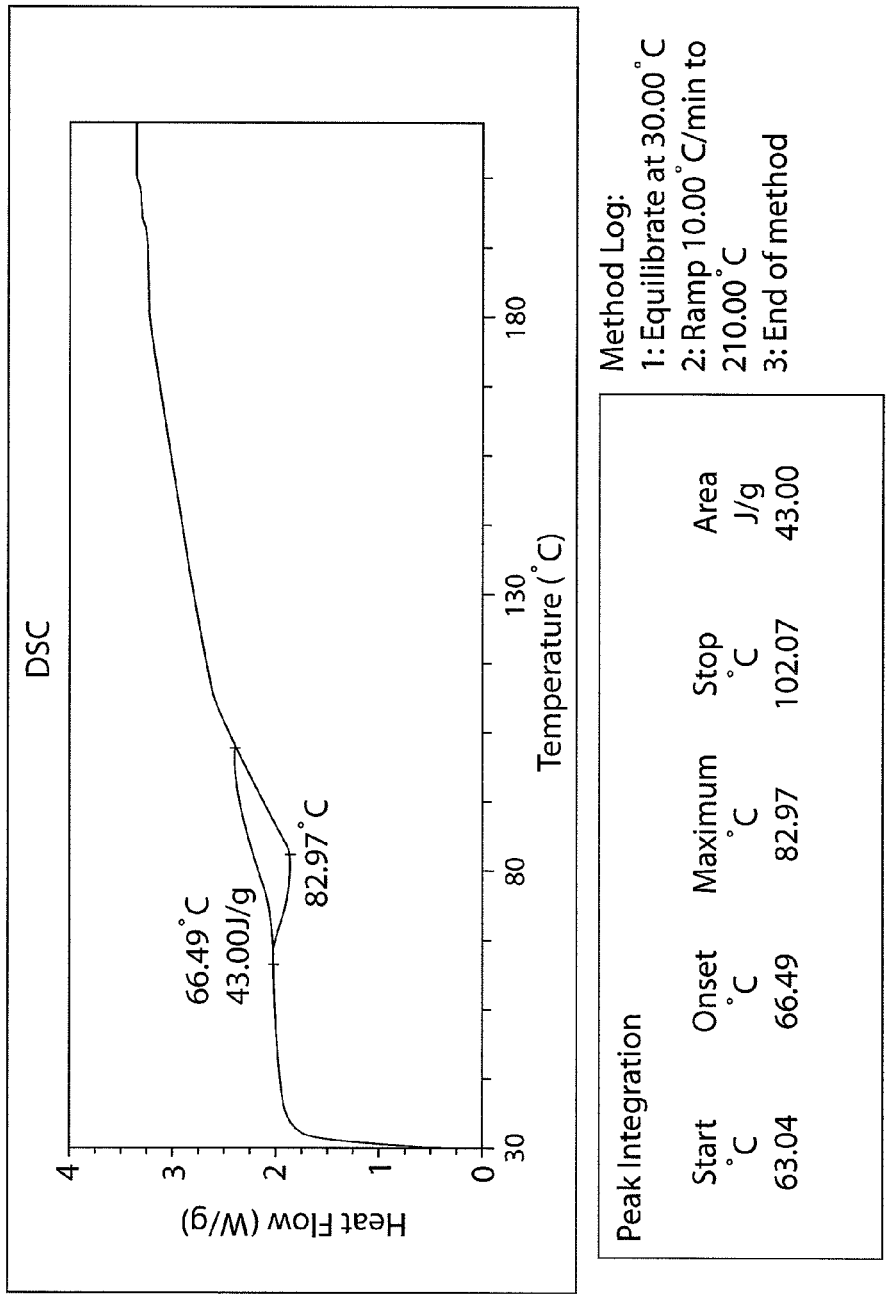
FIG. 18: DSC of N-octyl D-Glucamine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid.

13. A salt of a compound according to claim 1, wherein the N-octyl Glucamine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid is characterized by a differential scanning calorimetry thermogram substantially in accordance with that shown in FIG. 18.

Figure 6A:
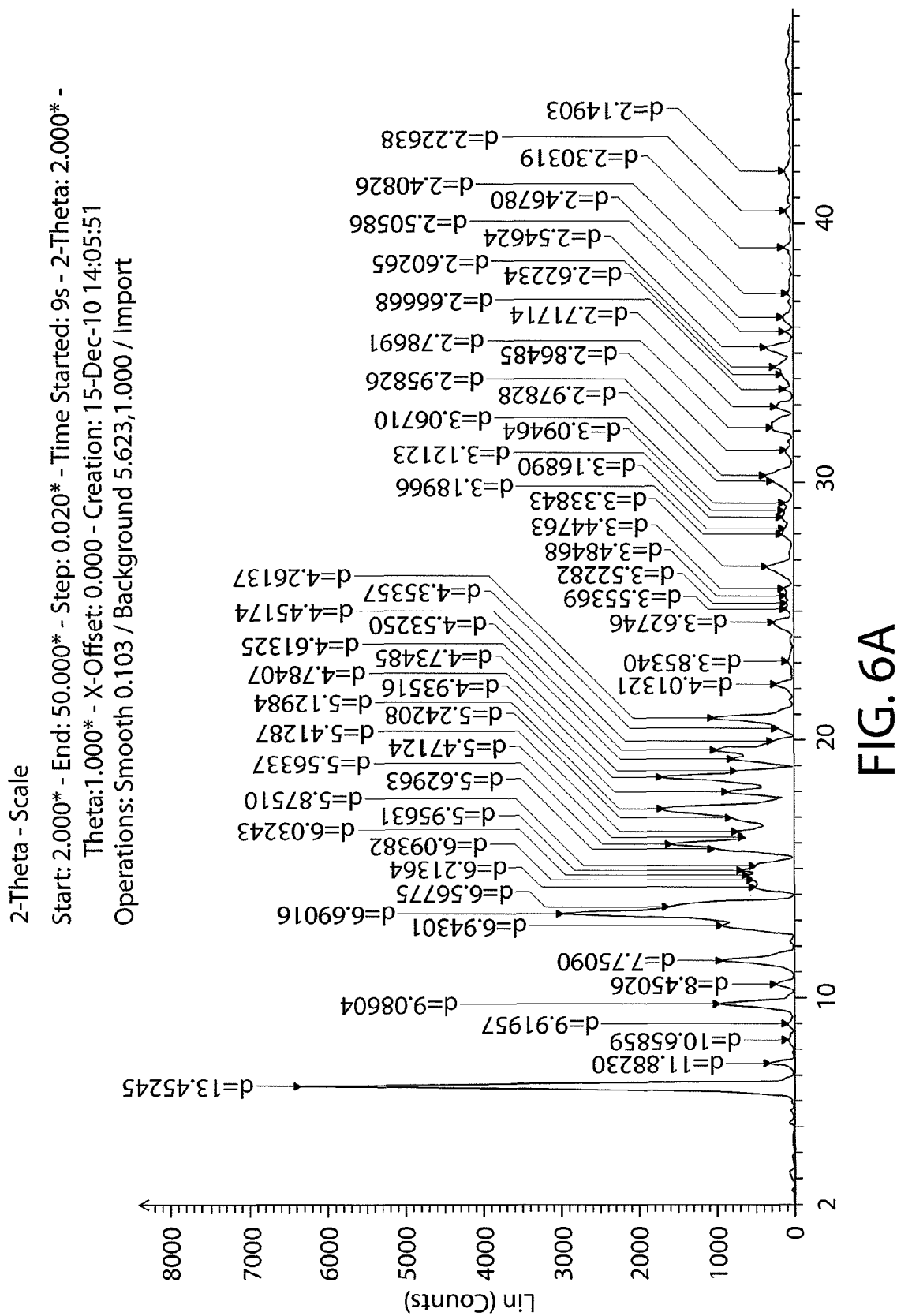
(FIG. 6A) XRPD of piperazine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid.
Figure 19:
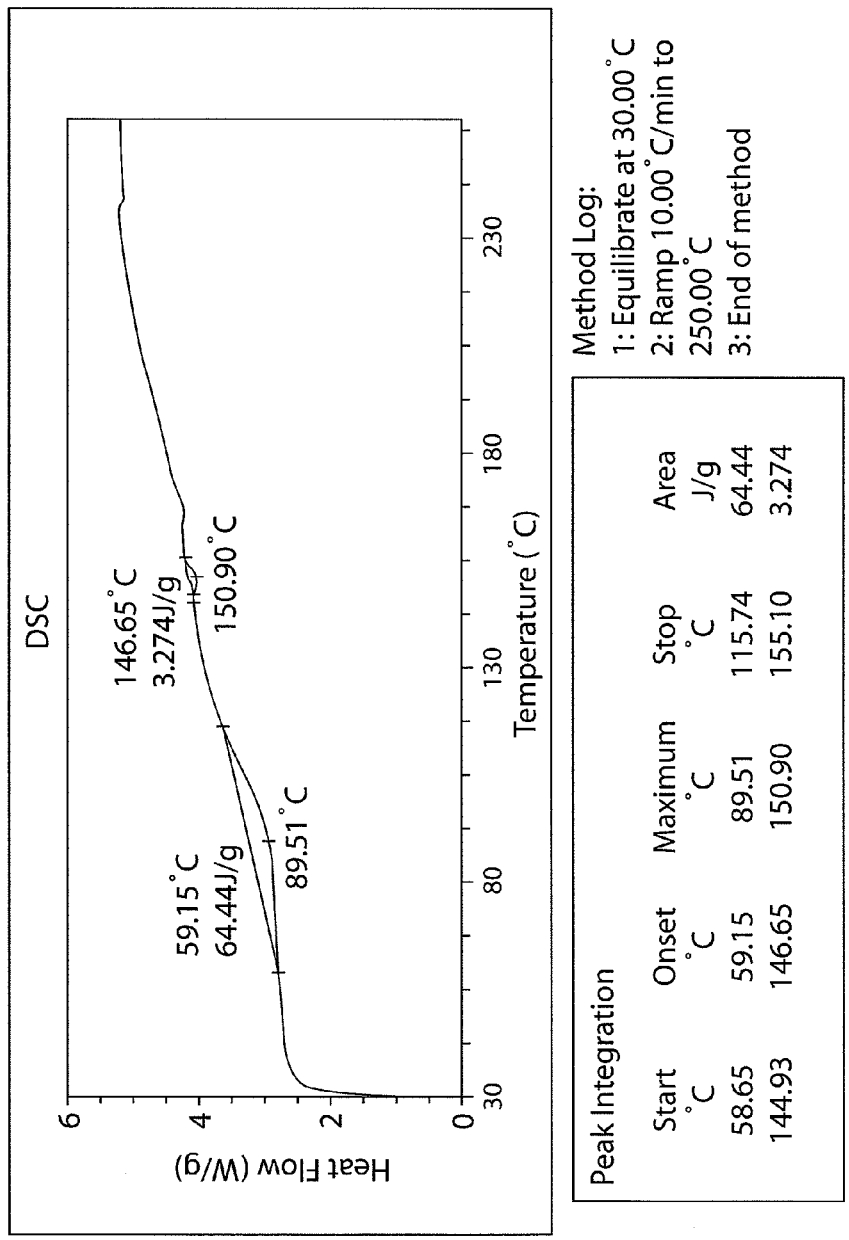
FIG. 19: DSC of Piperazine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid.

14. A salt of a compound according to claim 1, wherein the piperazine salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid is characterized by an x-ray powder diffraction pattern substantially in accordance with that shown in FIG. 6 and a differential scanning calorimetry thermogram substantially in accordance with that shown in FIG. 19.

Figure 21:
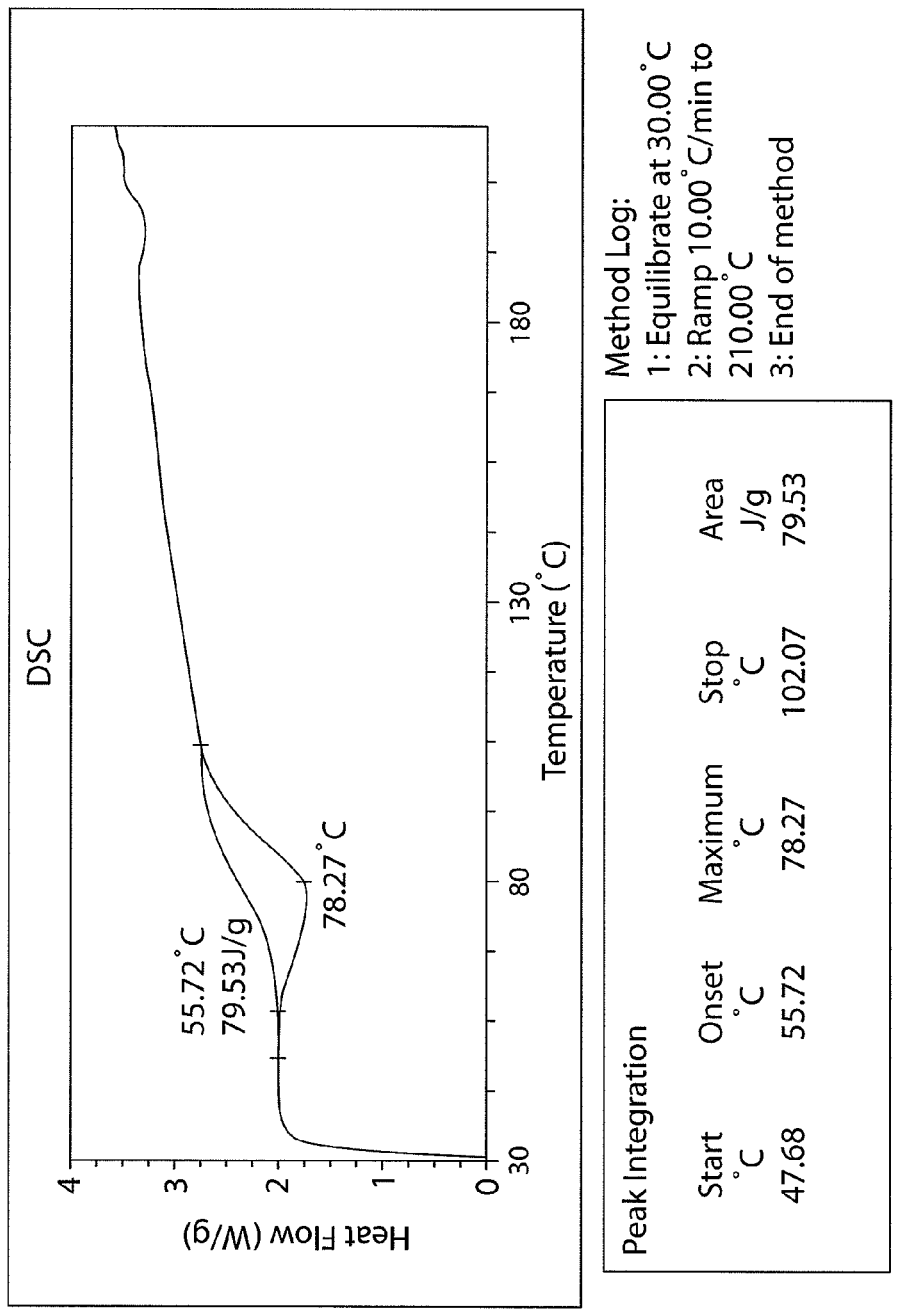
FIG. 21: DSC of Phenyl Glycine methyl ester of 4-((1R, 3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid.

15. A salt of a compound according to claim 1, wherein the Phenyl glycine methyl ester salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid is characterized by a differential scanning calorimetry thermogram substantially in accordance with that shown in FIG. 21.

Figure 20:
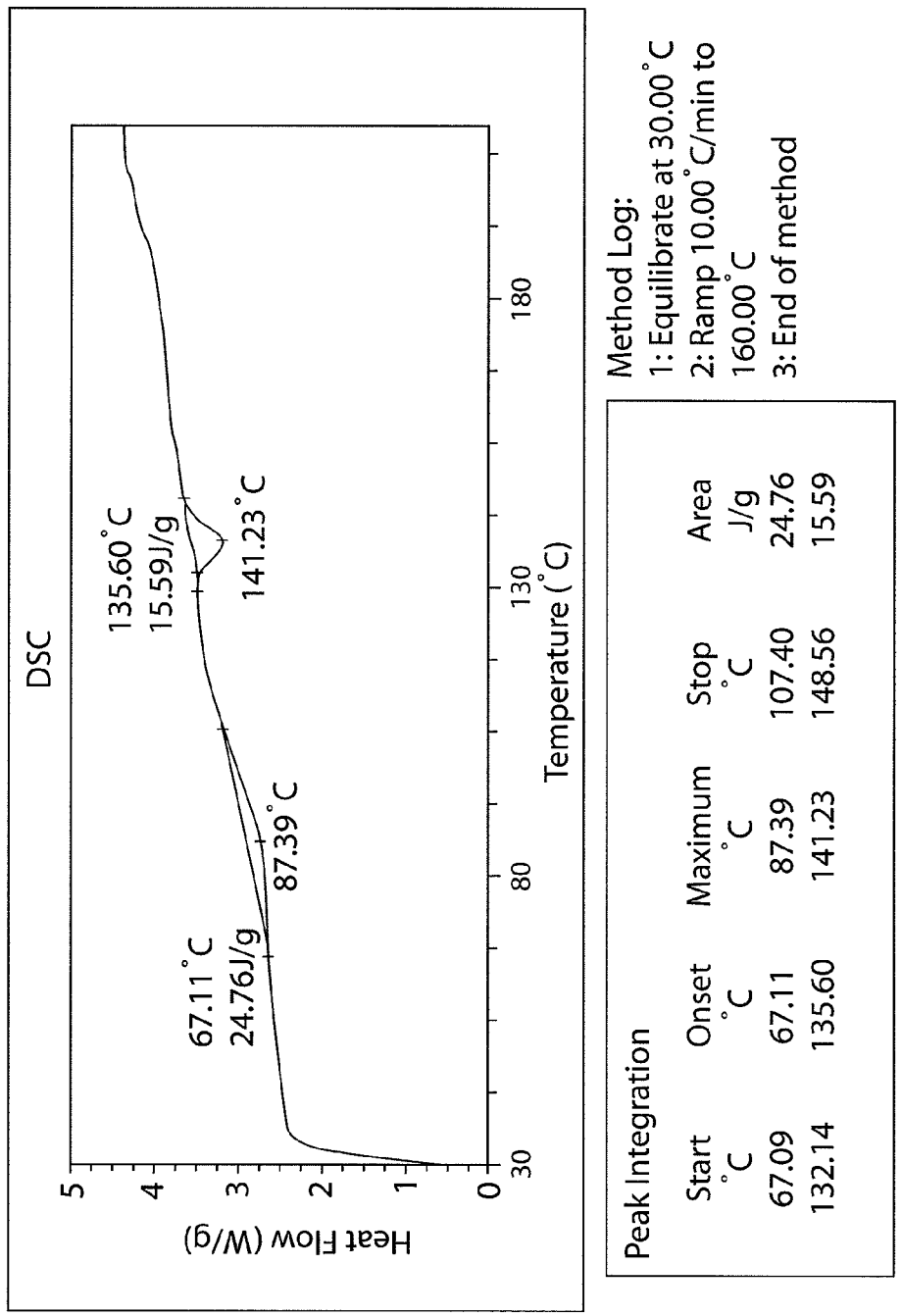
FIG. 20: DSC of S-phenyl glycinol salt of 4-((1R,3aR,5aR, 5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid.

16. A salt of a compound according to claim 1, wherein the Phenyl glycinol salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid is characterized by a differential scanning calorimetry thermogram substantially in accordance with that shown in FIG. 20.

Figure 22:
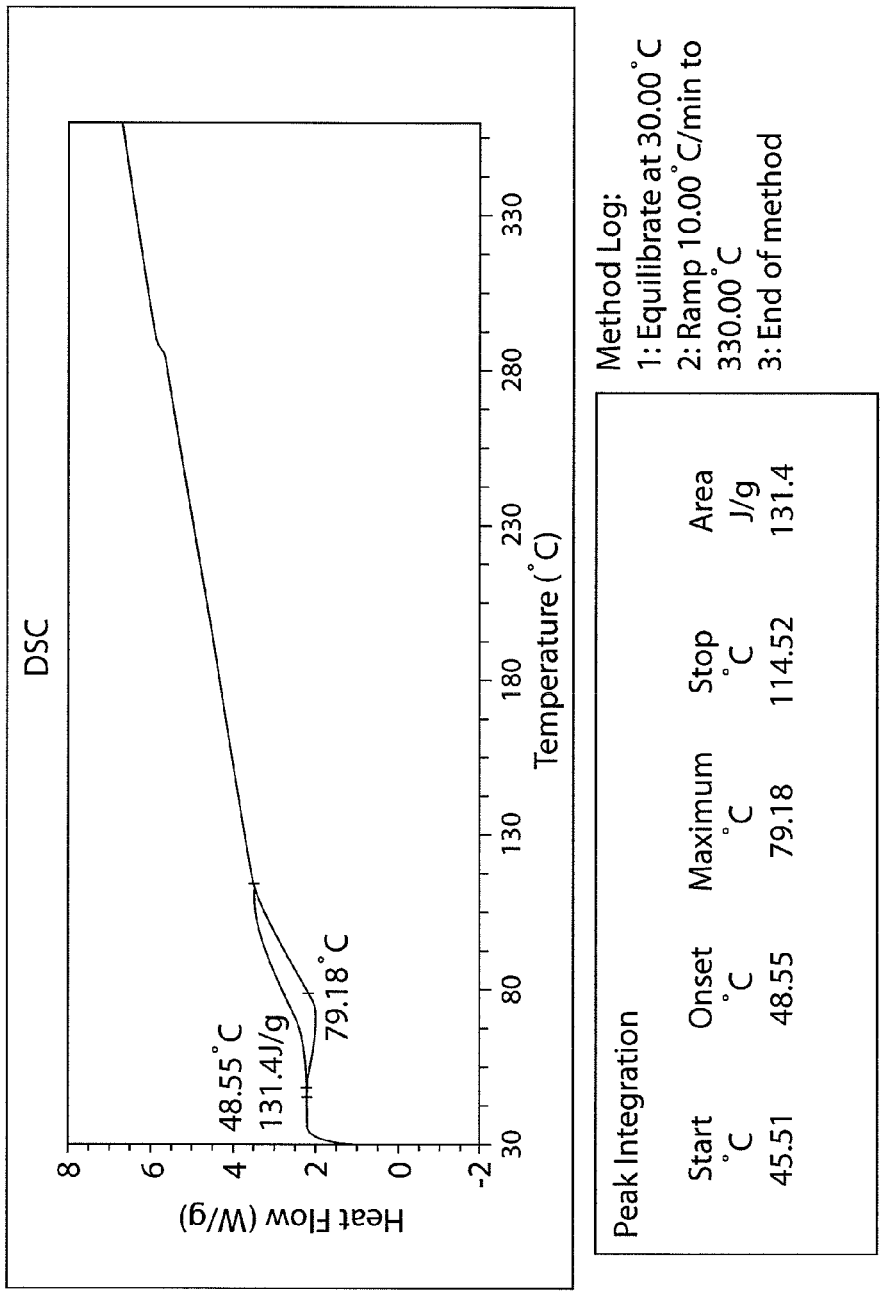
FIG. 22: DSC of Potassium salt of 4-((1R,3aR,5aR,5bR, 9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid.

17. A salt of a compound according to claim 1, wherein the Potassium salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid is characterized by a differential scanning calorimetry thermogram substantially in accordance with that shown in FIG. 22.

Figure 7A:
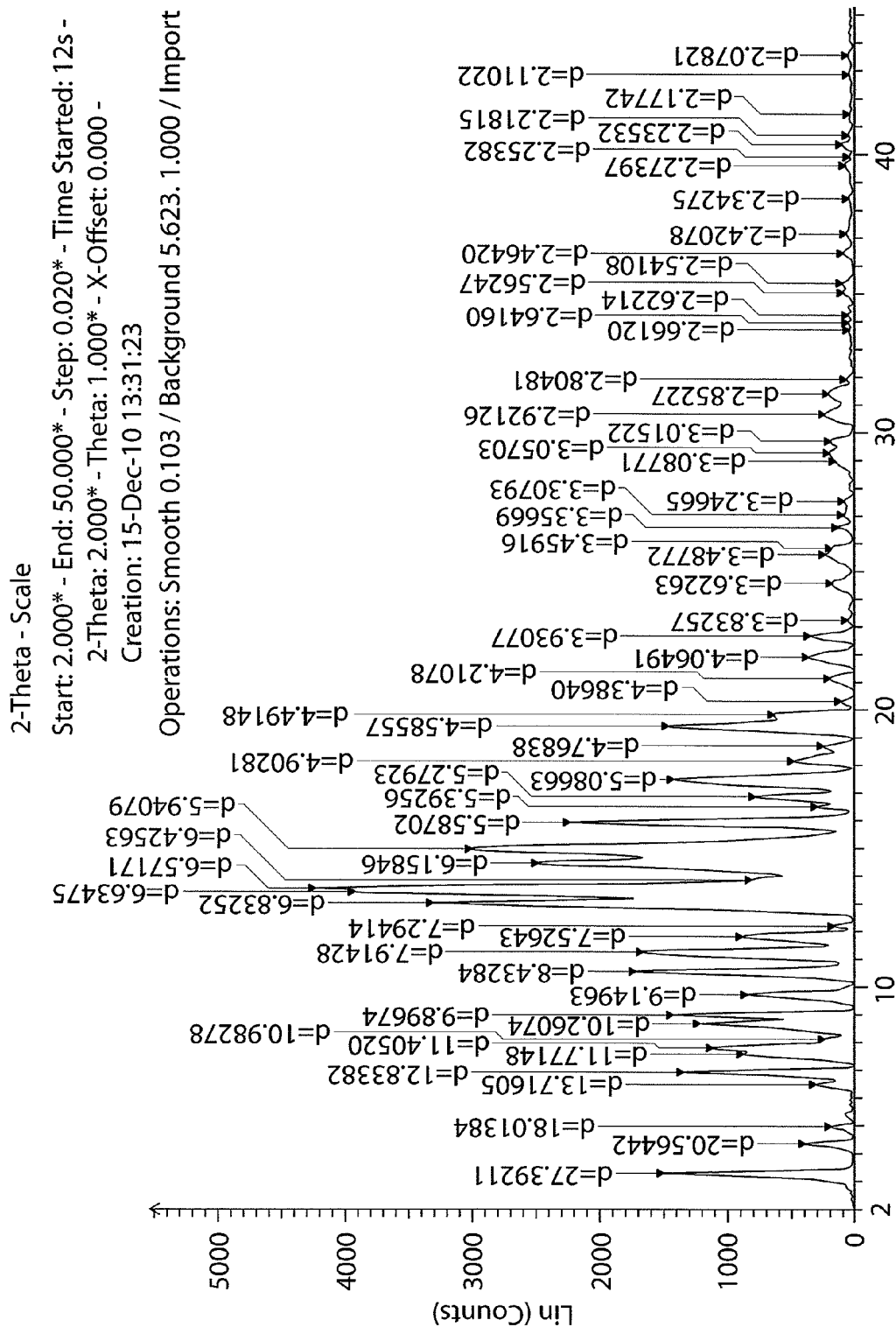
(FIG. 7A) XRPD of Sodium salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid.
Figure 23:
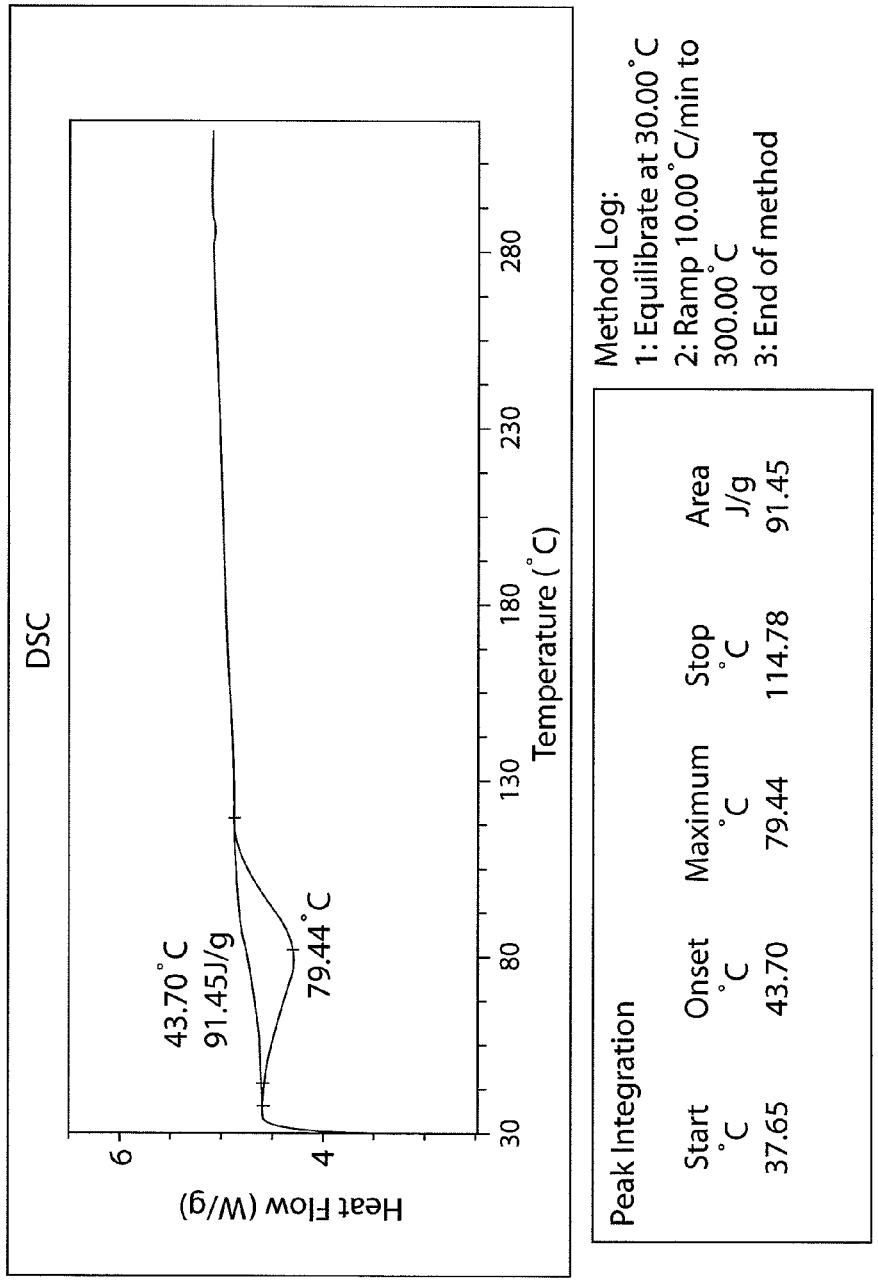
FIG. 23: DSC of Sodium salt of 4-((1R,3aR,5aR,5bR,9S, 11aR)-3a-((1R,3S)-2,2-dimethyl-3-(piperidine-1-carbonyl) cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid.

18. A salt of a compound according to claim 1, wherein the Sodium salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid is characterized by an x-ray powder diffraction pattern substantially in accordance with that shown in FIG. 7 and a differential scanning calorimetry thermogram substantially in accordance with that shown in FIG. 23.

Figure 24:
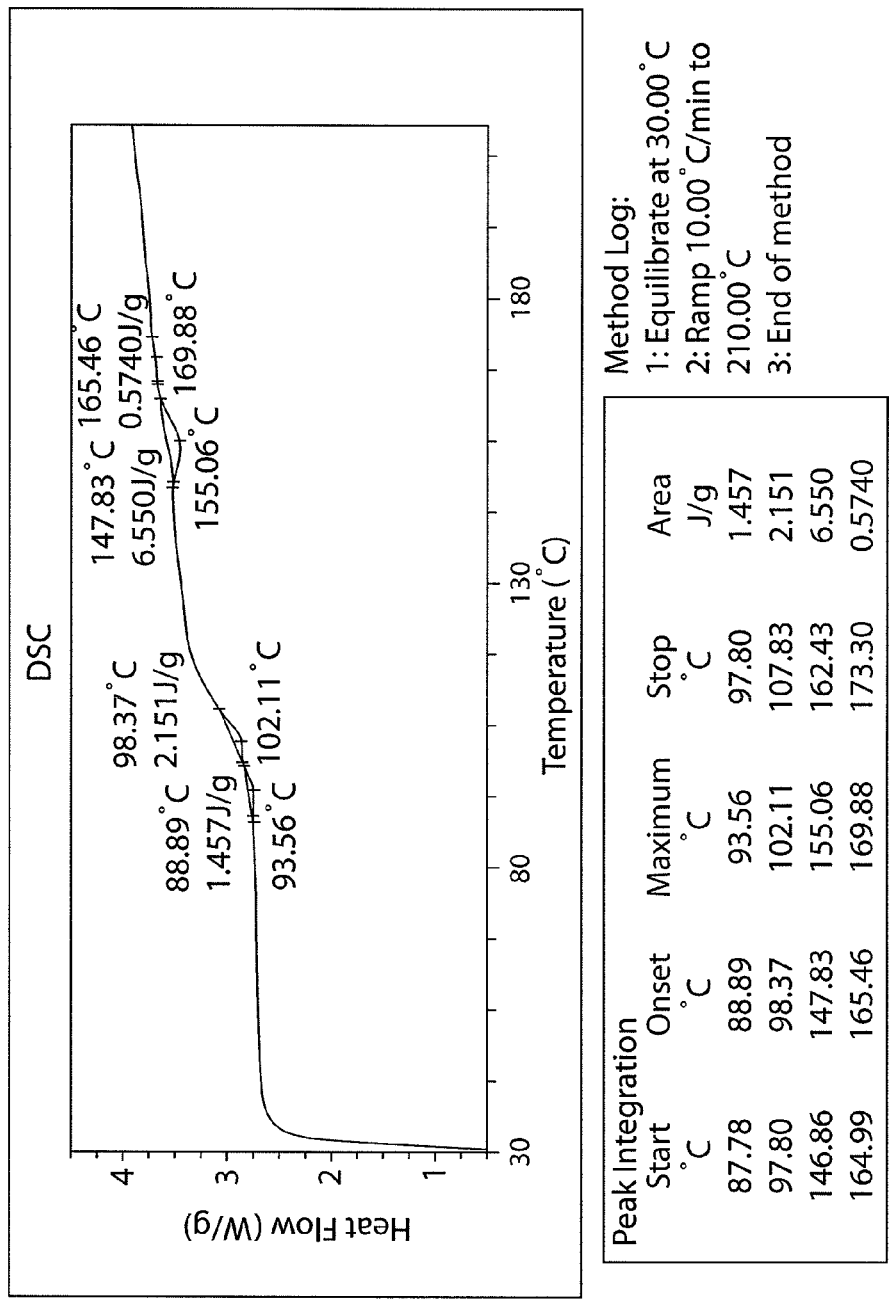
FIG. 24: DSC of Tris(hydroxymethyl) amino methane salt of 4-((1R,3aR,5aR,5bR,9S,11aR)-3a-((1R,3S)-2,2-dimethyl-3-(piperidine-1-carbonyl)cyclobutylcarbamoyl)-5a, 5b,8,8,11a-pentamethyl-1-(prop-1-en-2-yl)icosahydro-1H-cyclopenta[a]chrysen-9-yloxy)-2,2-dimethyl-4-oxobutanoic acid.

19. A salt of a compound according to claim 1, wherein the Tris(hydroxymethyl)amino methane salt of 4-((1R,3aR,5aR,5bR,9S,11aR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid is characterized by a differential scanning calorimetry thermogram substantially in accordance with that shown in FIG. 24.

20. A pharmaceutical composition comprising a salt compound according to any one of claims 1-19 and a pharmaceutically acceptable excipient.

21. The pharmaceutical composition according to claim 20, wherein the pharmaceutically acceptable excipient is a carrier or diluent.

22. A method for ameliorating HIV infection in a subject in need thereof comprising administering to the subject a therapeutically effective amount of a salt compound according to any one of claims 1-19.

23. A method for ameliorating HIV infection in a subject in need thereof comprising administering to the subject a pharmaceutical composition according to claim 20.

24. A salt of a compound of formula (I):

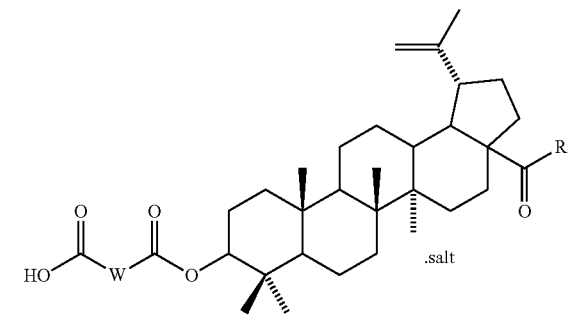

Formula (I)

Wherein,
R is OH,

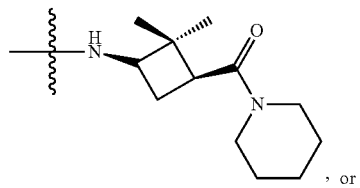

, or

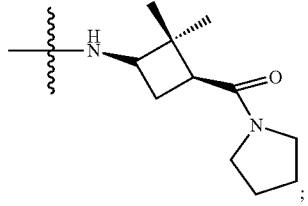

;

W is

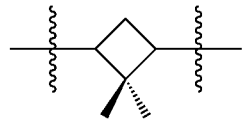

Salt is an arginine, amino guanidine, choline, dicyclohexylamine, diethanolamine, dimethyl piperazine, lithium, lysine, magnesium, N-octyl glucamine, piperazine, phenyl glycine methyl ester, phenyl glycinol, Trizma base primary standard buffer, or calcium, stereoisomers, enantiomers, diastereomers, racemates, or mixtures thereof.

* * * * *